(12) United States Patent
Mori et al.

(10) Patent No.: US 6,991,908 B1
(45) Date of Patent: Jan. 31, 2006

(54) ANTIOBESTIC AGENTS METHODS FOR SCREENING ANTIOBESTIC AGENTS AND KITS COMPRISING SAME

(75) Inventors: Masaaki Mori, Ibaraki (JP); Yukio Shimomura, Ibaraki (JP); Shiro Takekawa, Ibaraki (JP); Tsukasa Sugo, Ibaraki (JP); Yoshihiro Ishibashi, Ibaraki (JP); Chieko Kitada, Osaka (JP); Nobuhiro Suzuki, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/869,540

(22) PCT Filed: Dec. 27, 1999

(86) PCT No.: PCT/JP99/07337

§ 371 (c)(1),
(2), (4) Date: Jun. 27, 2001

(87) PCT Pub. No.: WO96/18651

PCT Pub. Date: Jun. 20, 1996

(30) Foreign Application Priority Data

Dec. 28, 1998 (JP) .......................... 10-374454
Apr. 28, 1999 (JP) .......................... 11-122688
Sep. 2, 1999 (JP) .......................... 11-249300

(51) Int. Cl.
*G01N 33/53* (2006.01)

(52) U.S. Cl. .................. 435/7.1; 436/504; 436/808; 530/300; 530/350

(58) Field of Classification Search ................ 435/7.1; 530/300, 350
See application file for complete search history.

(56) References Cited

U.S. PATENT DOCUMENTS 5,849,708 A * 12/1998 Maratos-Flier
6,221,616 B1 * 4/2001 Salon et al.
2002/0038007 A1 * 3/2002 Ames et al.

FOREIGN PATENT DOCUMENTS

EP          A-848060        12/1997
WO          WO 96/18651     12/1995
WO          WO 99/28492     12/1998

OTHER PUBLICATIONS

Bolton et al. The labeling of proteins to high specific radioactivities by conjugation to a 125I–containing acylating agent. 1973. Biochem. J., 133:529–539.*
Shimonura, Y. et al., *B.B.R.C.*, vol. 261 (3), 622–626, 1999.
Kolakowski, L.F., et al., *FEBS Letters*, vol. 398, 253–258, 1996.
Nahon, J.L., et al., *Endocrinology*, vol. 125 (4), 2056–2065, 1989.
Vaughan, J.M., et al., *Endocrinology*, vol. 125 (3), 1660–1665, 1989.
Thompson, Robert C., et al., *DNA and Cell Biology*, vol. 9 (9) 637–645, 1990.
Breton, C., et al., *Mol. Brain Res.*, vol. 18, (4), 297–310, 1993.
Lakaye, B., et al, *Biochemica et Biophysica Acta*, vol. 1401 (2), 216–220, 1998.
Tkahashi, K., et al., *Kagaku to Seibutsu*, vol. 34, No. 7, 444–450, 1996 and translation thereof.
Shimada, M., et al., *Nature*, vol. 396, 670–674, 1998.
Bächner, D., et al., *FEBS Letters*, 00 (1999), 1–3.
Drozdz, R., et al., *Journal of Peptide Science*, vol. 1, 58–65, 1995.
Chambers, J., et al., *Nature*, vol. 400, 261–265, 1999.
Saito, Y., et al., *Nature*, vol. 400, 265–269, 1999.
Lembo, P.M.C., et al., *Nature Cell Biology*, vol. 1, 267–271, 1999.

* cited by examiner

*Primary Examiner*—Lorraine Spector
*Assistant Examiner*—Dong Jiang
(74) *Attorney, Agent, or Firm*—David G. Conlin; John B.

Alexander; Edwards & Angell, LLP

(57) ABSTRACT

The present invention provides a method for screening a compound or its salt that alters the binding property between MCH or its salt and SLC-1 or its salt, characterized by using MCH or its derivative or a salt thereof and SLC-1 or its salt is useful for screening an SLC-1 agonist which can be used not only as an appetite (eating) promoting agent but also as a prophylactic/therapeutic agent for weak pains, atonic bleeding, before and after expulsion, subinvolution of uterus, cesarean section, induced abortion, galactostasis, and the like, and an SLC-1 antagonist which can be used not only as an antiobestic agents (drug), an appetite (eating) modulator, and the like, but also as a prophylactic/therapeutic agent for hyperstimulation, ankylosing uterine contractions, fetal distress, uterine rupture, cervical laceration, preterm delivery, Prader-Wili syndrome and the like.

5 Claims, 10 Drawing Sheets

ANTIOBESTIC AGENTS METHODS FOR SCREENING ANTIOBESTIC AGENTS AND KITS COMPRISING SAME

FIELD OF THE INVENTION

The present invention relates to a method for screening an antiobestic agent, an appetite modulator or the like, characterized by using SLC-1 (FEBS Letters 398 (1996) 253–258, etc.), which is an orphan receptor protein, or its salt and MCH (melanin concentrating hormone (Endocrinology, vol. 125, 1660–1665 (1989), etc.) or its derivative, or a salt thereof.

BACKGROUND ART

Human SLC-1 found in human genome (FEBS Letters 398 (1996) 253–258) and rat SLC-1 found from a rat brain cDNA library (Biochimica et Biophysica Acta, 1401 (1998) 216–220) are collectively referred to as a G protein-coupled receptor or seven transmembrane receptor. They are one of many G protein-coupled receptor proteins called orphan receptors, because their ligands are unknown.

For determining ligands of these orphan G/protein-coupled receptor proteins, there was no other general means but only to predict the ligands from similarity in the primary structures of these G/protein-coupled receptor proteins. However, many orphan G protein-coupled receptor proteins are poor in homology to known receptors. Actually, it was difficult to predict the ligands only from the similarity in their primary structures, except that they are receptor subtypes of known ligands. On the other hand, since many orphan G protein-coupled receptor proteins were found by gene analysis, it is predicted that there will be still many other unknown ligands corresponding to those proteins. To date, however, only few ligands were identified for these organ G protein-coupled receptors. With respect to SLC-1, it has not been reported, either, if its ligand exists.

To survey ligands to the SLC-1 orphan receptor protein and establish a method for screening a compound, etc. characterized by using SLC-1 and its ligands have thus been the problems to be solved.

DISCLOSURE OF THE INVENTION

Using cells expressing SLC-1 encoding cDNA by a suitable means, the present inventors have succeeded in screening a polypeptide recognized by the receptor protein as a ligand, by assaying a specific cell stimulating (signal transduction) activity, etc. as an index and have found that the polypeptide is MCH (melanin concentrating hormone). Furthermore, the present inventors have found that a compound capable of altering the binding property between the activator MCH or its salt and the SLC-1 or its salt described above can be screened.

The present inventors have also, found that the amino acid sequence of human SLC-1 of the present invention is a novel sequence different from the amino acid sequence previously reported (FEBS Letters, 398 (1996) 253–258, WO 96/18651).

That is, the present invention provides the following features.

(1) A method for screening a compound or its salt that alters the binding property between a melanin concentrating hormone (MCH) or its salt and SLC-1 or its salt, which comprises use of the MCH or its derivative, or a salt thereof and SLC-1 or its salt.

(2) A kit for screening a compound or its salt that alters the binding property between MCH or its salt and SLC-1 or its salt, comprising the MCH or its derivative; or a salt thereof and SLC-1 or its salt.

(3) A compound or its salt that alters the binding property between MCH or its salt and SLC-1 or its salt, which is obtainable by using the screening method according to (1) or the screening kit according to (2).

(4) A pharmaceutical composition comprising the compound or its salt according to (3).

(5) A compound or its salt according to (4), which is an antiobestic agent.

(6) A protein containing the amino acid sequence represented by SEQ ID NO:11, or a salt thereof.

(7) A DNA comprising a DNA containing a base sequence encoding the protein according to (6).

(8) A screening method according to (1) or a screening kit according to (2), wherein the MCH is a peptide containing the same or substantially the same amino acid sequence as the amino acid sequence represented by SEQ ID NO:2.

(9) A screening method according to (1) or a screening kit according to (2), wherein the derivative is a peptide containing a partial sequence of the 5th to the 19th from the N terminus of the amino acid sequence represented by SEQ ID NO:2.

(10) A screening method according to (1) or a screening kit according to (2), wherein the derivative is MCH derivatized with a Bolton-Hunter reagent or a peptide derivatized with a Bolton-Hunter reagent and containing a partial sequence of the 5th to the 19th from the N terminus of the amino acid sequence represented by SEQ ID NO:2.

(11) MCH derivatized with a Bolton-Hunter reagent, or a peptide derivatized with a Bolton-Hunter reagent and containing a partial sequence of the 5th to the 19th from the N terminus of the amino acid sequence represented by SEQ ID NO:2 or its salt.

(12) A compound represented by formula:

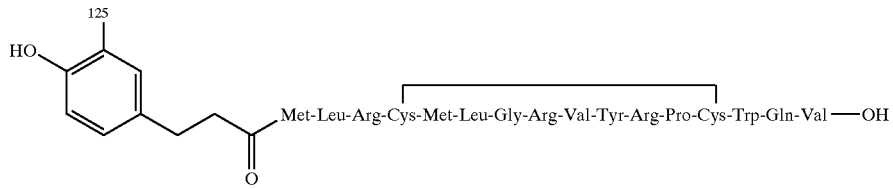

or its salt.

Specifically, the SLC-1 used in the present invention includes the publicly known SLC-1 described above or its salt, as well as the following compounds.

(13) An SLC-1 containing the same or substantially the same amino acid sequence as the amino acid sequence represented by SEQ ID NO:5 or SEQ ID NO:11, or its salt.

(14) An SLC-1 or its salt according to (13), which is a protein containing the amino acid sequence shown by SEQ ID NO:5 or SEQ ID NO:11, of which 1 to 30, preferably 1 to amino acids are deleted, the amino acid sequence shown by SEQ ID NO: 5 or SEQ ID NO:11, to (or in) which 1 to 30, preferably 1 to 10, amino acids are added (or inserted); or the amino acid sequence shown by SEQ ID NO:5 or SEQ ID NO:11, in which 1 to 30, preferably 1 to 10, amino acids are substituted with other amino acids.

Specifically, the MCH in the present invention includes the publicly known MCH described above or its salt, as well as the following compounds.

(15) An MCH containing the same or substantially the same amino acid sequence as the amino acid sequence represented by SEQ ID NO:2, or its derivative, or a salt thereof.

(16) An MCH or its derivative, or a salt thereof according to (15), wherein the protein is a peptide containing the amino acid sequence shown by SEQ ID NO: 2, of which 1 to 10, preferably 1 to 5, amino acids are deleted, the amino acid sequence shown by SEQ ID NO: 2, to (or in) which 1 to 10, preferably 1 to 5, amino acids are added (or inserted); or the amino acid sequence shown by SEQ ID NO: 2, in which 1 to 10, preferably 1 to 5, amino acids are substituted with other amino acids.

BEST MODE OF EMBODIMENT OF THE INVENTION

Figure 1:
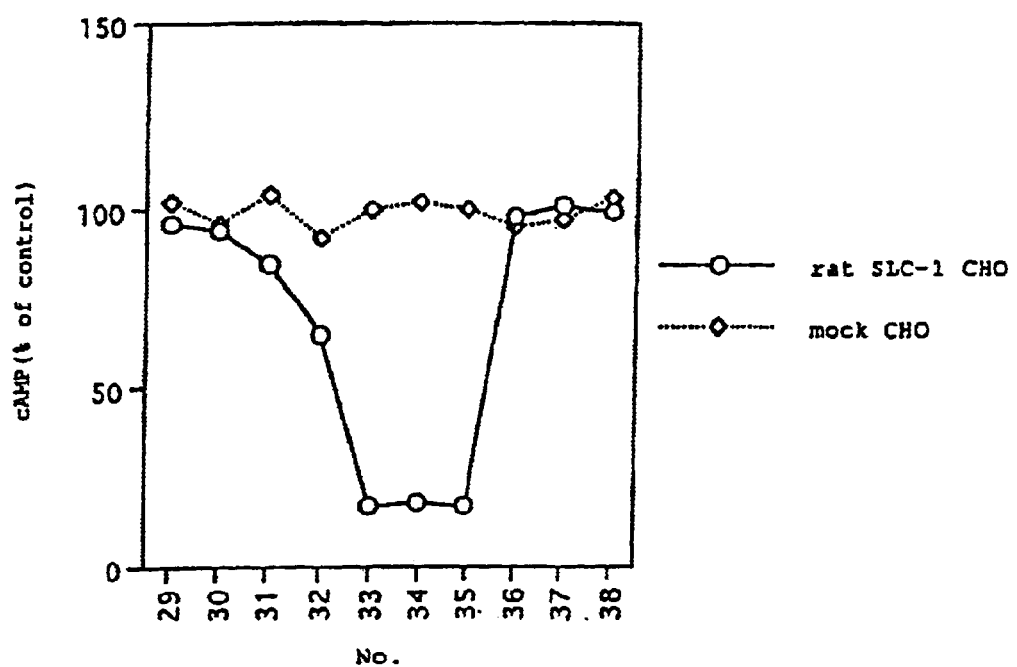
FIG. 1 shows results obtained by assaying a cAMP synthesis inhibitory activity specific to CHO/SLC-1 cells on the HPLC fractions prepared from rat brain.

In the present specification, the term "substantially the same" is used to mean that the activities of polypeptides, etc., e.g. the binding property between a ligand (MCH) and a receptor (SLC-1), physical activities, etc. are substantially the same.

Methods of manufacturing the SLC-1 or its salts (hereinafter sometimes collectively referred to as SLC-1) and the MCH or its derivatives or salts thereof (hereinafter sometimes collectively referred to as MCH), which are employed in the present invention, are described below in further detail.

The SLC-1 and MCH employed in the present invention may be any polypeptide derived from any tissues (e.g., pituitary, pancreas, brain, kidney, liver, genital gland, thyroid gland, gall bladder, spinal cord, adrenal, skin, muscle, lung, digestive tract, blood vessel, heart, etc.) or cells, etc., of human, other warm-blooded animals (e.g., guinea pig, rat, mouse, swine, sheep, bovine, monkey, etc.) and fish, etc., in which SLC-1 may be any polypeptide containing the same or substantially the same amino acid sequence as the amino acid sequence shown by SEQ ID NO:5 or SEQ ID NO:11 and MCH may be any polypeptide containing the same or substantially the same amino acid sequence as the amino acid sequence shown by SEQ ID NO:2. Examples of the SLC-1 of the present invention include, in addition to the polypeptide or the like containing the amino acid sequence shown by SEQ ID NO:5 or SEQ ID NO:11, a polypeptide or the like which has an activity substantially equivalent to the polypeptide containing the amino acid sequence shown by SEQ ID NO:5 or SEQ ID NO:11. Examples of the substantially equivalent activity include a ligand binding activity, a signal transduction activity, and the like. The term substantially equivalent means that the nature of the ligand binding activity, etc. is equivalent. Therefore, differences in degree such as a level of the ligand binding activity and quantitative factors such as a molecular weight of the polypeptide may be present and allowable. Examples of the MCH of the present invention include, in addition to the polypeptide containing the amino acid sequence shown by SEQ ID NO:2, a polypeptide which has an activity substantially equivalent to the polypeptide containing the amino acid sequence shown by SEQ ID NO:2. Examples of the substantially equivalent activity include a receptor binding activity, and the like. The term substantially equivalent is used to mean that the nature of the receptor binding activity, etc. is equivalent. Therefore, differences in degree such as a level of the receptor binding activity and quantitative factors such as a molecular weight of the polypeptide may be present and allowable.

In the present specification, the SLC-1 and MCH are represented in accordance with the conventional way of describing peptides, that is, the N-terminus (amino terminus) at the left hand and the C-terminus (carboxyl terminus) at the right hand. For example, in a polypeptides containing the amino acid sequence shown by SEQ ID NO:2, SEQ ID NO: 5 or SEQ ID NO: 11, the C-terminus is usually in the form of a carboxyl group (—COOH) or a carboxylate (—COO) but may also be in the form of an amide (—CONH$_2$) or an ester (—COOR). Examples of the ester group shown by R include a C$_{1-6}$ alkyl group such as methyl, ethyl, n-propyl, isopropyl, n-butyl, etc.; a C$_{3-8}$ cycloalkyl group such as cyclopentyl, cyclohexyl, etc.; a C$_{5-12}$ aryl group such as phenyl, α-naphthyl, etc.; a phenyl-C$_{1-2}$ alkyl group, e.g., benzyl, phenethyl, benzhydryl, etc.; a C$_{7-14}$ aralkyl such as an α-naphthyl-C$_{1-2}$ alkyl group, e.g., α-naphthylmethyl, etc.; and the like. In addition, pivaloyloxymethyl or the like which is widely used as an ester for oral administration may be used as well.

The SLC-1 and MCH of the present invention may be used in the form of salts with physiologically acceptable bases (e.g., alkali metals) or acids (e.g., inorganic acids or organic acids), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The SLC-1 and MCH used in the present invention may be manufactured by modified methods of publicly known methods (e.g., those described in FEBS Letters, 398 (1996) 253–258, WO 96/18651), that is, methods used to purify polypeptides from tissues or cells of human or other warm-blooded animal. Alternatively, the SLC-1 and MCH may also be manufactured by modifications of the methods for synthesis of proteins (peptides), which will be described hereinafter. Furthermore, the SLC-1 and MCH may be manufactured by culturing a transformant containing a DNA encoding the protein (peptide), which will also be later described.

Where the SLC-1 and MCH are manufactured from the tissues or cells of human, other warm-blooded animal, fish, etc., the tissues or cells of human, other warm-blooded animal or fish, etc. are homogenized. The homogenate is then extracted with an acid, an organic solvent or the like. The extract is purified and separated by means of salting-out, dialysis, gel filtration, or a combination of chromatography techniques such as reverse phase chromatography, ion exchange chromatography, affinity chromatography, etc.

As described above, the SLC-1 and MCH used in the present invention can be manufactured by publicly known methods for synthesis of proteins (peptides) or by cleaving proteins (peptides) containing the SLC-1 and/or MCH with an appropriate peptidase. For synthesis of proteins (peptides), for example, either solid phase synthesis or liquid phase synthesis may be used. That is, a partial peptide or amino acids capable of constructing the SLC-1 and/or MCH are condensed with the remaining part. When the product contains protecting groups, the desired protein (peptide) can be obtained by removing the protecting groups. The publicly known methods for condensation and those for removal of protecting groups include the methods described in 1)-5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: Seikagaku Jikken Koza (Biochemical Experiment) 1, *Tanpakushitsu no Kagaku* (Chemistry of Proteins) IV, 205 (1977)

5) Haruaki Yajima ed.: *Zoku Iyakuhin no Kaihatsu* (A sequel to Development of Pharmaceuticals), Vol. 14, Peptide Synthesis, published by Hirokawa Shoten.

After completion of the reaction, the protein (peptide) may be purified and isolated by a combination of conventional purification methods such as solvent extraction, distillation, column chromatography, liquid chromatography, recrystallization, etc. When the protein (peptide) obtained by the above methods is in a free form, the protein (peptide) can be converted into an appropriate salt by a publicly known method; when the protein (peptide) is obtained in a salt form, it can be converted into a free form by a publicly known method.

To synthesize the amides of SLC-1 and MCH, commercially available resins that are suitably used for amide formation may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin, in accordance with the order of the sequence of the objective peptide, by various condensation methods publicly known in the art. At the end of the reaction, the protein (peptide) is excised from the resin and at the same time, the various protecting groups are removed. Then, an intramolecular disulfide bond-forming reaction is carried out, if necessary, in a highly diluted solution to obtain the objective protein (peptide).

For condensation of the protected amino acids described above, a variety of activating reagents that can be used for proteins (peptides) synthesis may be used. In particular, carbodiimides are preferably employed. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt, etc.) are added directly to the resin, or the protected amino acids are previously activated into the corresponding symmetric acid anhydrides, HOBt esters or HOOBt esters, followed by adding the thus activated protected amino acids to the resin. Solvents suitably used to activate the protected amino acids or condense with the resin may be appropriately selected from solvents that are known to be usable for condensation reactions of proteins (peptides). Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; tertiary amines such as pyridine, etc.; ethers such as dioxane, tetrahydrofuran, etc.; nitriles such as acetonitrile, propionitrile, etc.; esters such as methyl acetate, ethyl acetate, etc.; and suitable mixtures of these solvents. The reaction temperature is appropriately chosen from the range known to be applicable to peptide bond-forming reactions and is usually selected within the range of approximately −20° C. to 50° C. The activated amino acid derivatives are used generally in an excess of 1.5 to 4 times. The condensation is tested using the ninhydrin reaction; when the test indicates that the condensation is insufficient, the condensation can be completed by repeating the condensation reaction without removal of the protecting groups. When the condensation is still insufficient even after repeating the reaction, unreacted amino acids are acetylated with acetic anhydride or acetylimidazole to cancel any possible adverse effect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc. Examples of the protecting group R for a carboxyl group include, in addition to those examples for the $C_{1-6}$ alkyl group, the $C_{3-8}$ cycloalkyl group and the $C_{7-14}$ aralkyl group described hereinabove, 2-adamantyl, 4-nitrobenzyl, 4-methoxybenzyl, 4-chlorobenzyl, phenacyl and benzyloxycarbonylhydrazide, t-butoxycarbonylhydrazide, tritylhydrazide, and the like.

The hydroxyl group of serine and threonine can be protected through, for example, esterification or etherification. Examples of groups appropriately used for the esterification include a lower alkanoyl group such as acetyl, etc., an aroyl group such as benzoyl group, and a group derived from carbon such as benzyloxycarbonyl group and ethoxycarbonyl group. Examples of groups appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting materials include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino groups in the starting material, the corresponding phosphoric amides are employed.

To eliminate (split off) the protecting groups, there are used catalytic hydrogenation in a hydrogen gas flow in the presence of a catalyst such as Pd-black or Pd-carbon;
a treatment with an acid, for example, anhydrous hydrogen fluoride, methanesulfonic acid, trifluoromethanesulfonic acid, trifluoroacetic acid, a mixture thereof, etc.; a treatment with a base, for example, diisopropylethylamine, triethylamine, piperidine, piperazine, etc.; reduction with sodium in liquid ammonia; and the like. Elimination of the protecting groups by the acid treatment described above is carried out generally at a temperature of approximately $-20°$ C. to $40°$ C. In the acid treatment, addition of a cation scavenger such as anisole, phenol, thioanisole, m-cresol, p-cresol, dimethyl sulfide, 1,4-butanedithiol, 1,2-ethanedithiol or the like is effective. Also, 2,4-dinitrophenyl group used for protecting the imidazole protecting group of histidine is removed by a treatment with thiophenol. Formyl group used for protecting the indole protecting group of tryptophan is eliminated by the aforesaid acid treatment in the presence of 1,2-ethanedithiol or 1,4-butanedithiol, as well as by a treatment with an alkali such as a dilute sodium hydroxide solution, dilute ammonia, etc.

Publicly known groups and means can be appropriately selected for protection of a functional group which should not participate in the reaction of the starting material and its protecting group as well as removal of the protecting group, activation of a functional group which participates in the reaction, and the like.

In another method for obtaining the amides of SLC-1 and MCH, the α-carboxyl group of the carboxyl terminal amino acid is first amidated; the peptide chain is then extended toward the amino group side to have a desired chain length. Then, only the protecting group of the N-terminal α-amino group of the resultant peptide is removed to obtain a protein. Likewise, another peptide (or amino acid) is manufactured by removing only the protecting group of the C-terminal carboxyl group. The two peptides are condensed with each other in a solvent mixture as described above. The details of the condensation reaction are the same as described above. After the protected peptide obtained by the condensation is purified, all the protecting groups are removed by the methods described above to give the desired crude protein (peptide). After purifying the crude protein (peptide) by various known means for purification, the main fraction is lyophilized to give the amide of the desired protein (peptide).

To prepare the esters of SLC-1 and MCH, the α-carboxyl group of the carboxy terminal amino acid is condensed with a desired alcohol to prepare the amino acid ester, which is then treated in a manner similar to the preparation of the amides of protein(peptide) to give the esters of the desired protein(peptide).

The MCH derivative used in the present invention may be any peptide of ① a partial peptide of MCH, ② a peptide wherein the constituent amino acids of MCH are deleted, other amino acids are added to the constituent amino acids or the constituent amino acids are substituted with other amino acids, or ③ MCH, the partial peptide described in ① or the peptide described in ②, which is labeled, etc., so long as it is capable of binding to SLC-1.

Specific examples of the partial peptide of MCH include a peptide containing a partial sequence of the 5th to the 19th from the N terminus of the amino acid sequence represented by SEQ ID NO: 2, or its amides or esters, or salts thereof. More specifically, the partial peptides are a peptide containing the amino acid sequence shown by SEQ ID NO:19, SEQ ID NO:20, SEQ ID NO:21, SEQ ID NO:22, SEQ ID NO:23 or SEQ ID NO:24, or its amides or esters, or salts thereof.

When the screening later described is carried out using the SLC-1, a peptide particularly preferably containing the amino acid sequence shown by SEQ ID NO:21, its amides or esters, or salts thereof are preferably used.

Examples of the peptides wherein the constituent amino acids of MCH are deleted, other amino acids are added to the constituent amino acids or the constituent amino acids are replaced by other amino acids include those shown by SEQ ID NO:2, wherein at least 1 or 2 (preferably about 1 to about 10, more preferably, several (1 or 2)) amino acids are deleted; at least 1 or 2 (preferably about 1 to about 10, more preferably about 1 to about 5 and most preferably several (1 or 2)) amino acids are added to the amino acid sequence; or, at least 1 or 2 (preferably about 1 to about 10, more preferably about 1 to about 5 and most preferably several (1 or 2)) amino acids are replaced by other amino acids; and the like.

Substantially the same substitution of an amino acid in the amino acid sequences can be selected from, e.g., other amino acids of the class to which the amino acid belongs. Examples of non-polar (hydrophobic) amino acids include alanine, leucine, isoleucine, valine, proline, phenylalanine, tryptophan, methionine and the like. Examples of polar (neutral) amino acids are glycine, serine, threonine, cysteine, tyrosine, asparagine, glutamine, and the like. Examples of positively charged (basic) amino acids are arginine, lysine, histidine, and the like. Examples of negatively charged (acidic) amino acids include aspartic acid, glutamic acid, and the like.

However, the location at which other amino acids are deleted or substituted as described above is preferably at the position other than Cys in the constituent amino acids of MCH.

As the labeled forms of MCH, the peptide described in ① or the peptide described in ②, there are isotope-labeled forms, fluorescence-labeled forms (fluorescent labeling with, e.g., fluorescein), biotinylated forms, enzyme-labeled forms, etc., by publicly known methods.

Specifically, MCH labeled with [³H], [¹²⁵I], [¹⁴C], [³⁵S], etc. by publicly known methods can be utilized. In particular, labeled forms of MCH or its derivatives, which are prepared by a publicly known method using a Bolton-Hunter reagent, may be utilized as well.

Specific examples of the labeled form of the MCH or its derivatives include the following compounds:

(1)
[¹²⁵I]-[N-(3-(4-Hydroxy-3-iodophenyl)propionyl)-Asp¹]-MC H

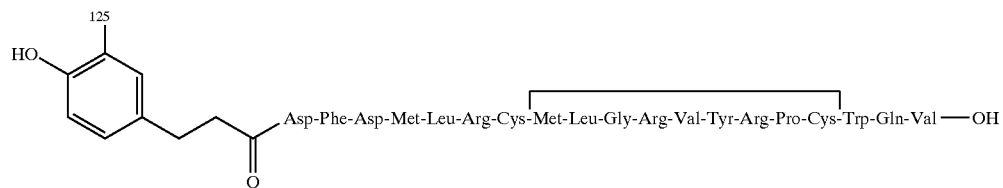

(2)
[¹²⁵I]-[N-(3-(4-Hydroxy-3-iodophenyl)propionyl)-Phe²]-MC H(2-19)

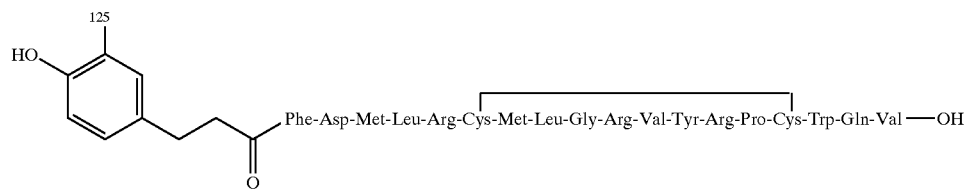

(3)
[¹²⁵I]-[N-(3-(4-Hydroxy-3-iodophenyl)propionyl)-Asp³]-MC H (3-19)

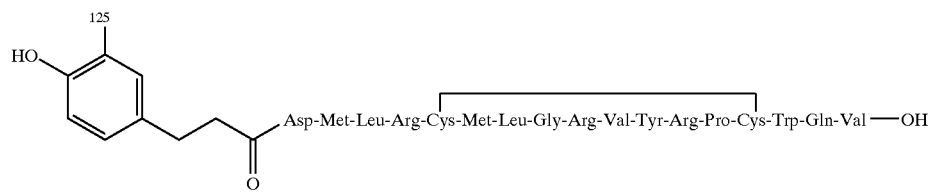

(4)
[¹²⁵I]-[N-(3-(4-Hydroxy-3-iodophenyl)propionyl)-Met⁴]-MC H(4-19)

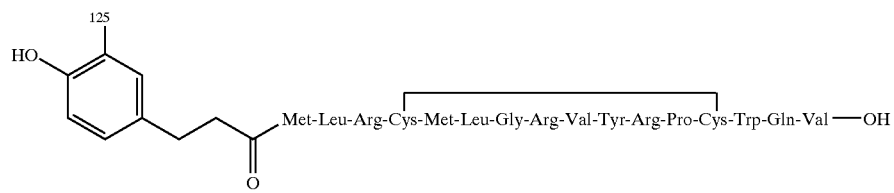

(5)
[¹²⁵I]-[N-(3-(4-Hydroxy-3-iodophenyl)propionyl)-Leu⁵]-MC H(5-19)

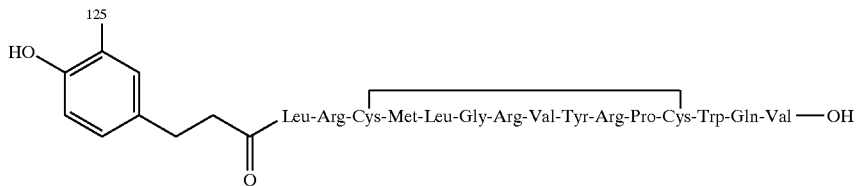

(6)
[$^{125}$I]-[N-(3-(4-Hydroxy-3-iodophenyl)propionyl)-Arg$^6$]-MCH(6-19)

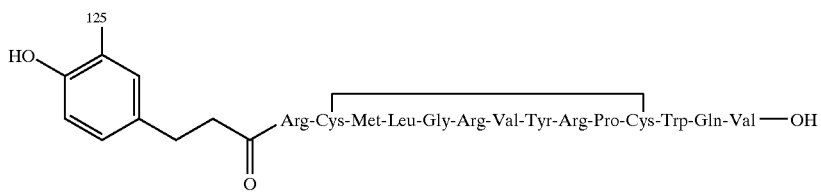

(7)
[125I]-[N-(3-(4-Hydroxy-3-iodophenyl)propionyl)-Cys$^7$]-MCH(7-19)

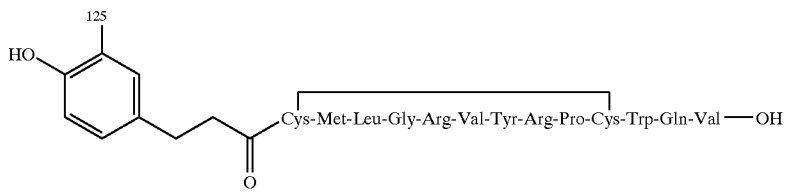

and the like.

Among them, [$^{125}$I]-[N-(3-(4-hydroxy-3-iodophenyl)propionyl)-Met$^4$]-MCH(4-19) is particularly preferably employed.

As the salts of MCH or its derivatives, examples are the same as those given for the salts of SLC-1 and MCH described above.

The DNA encoding the SLC-1 used in the present invention may be any DNA so long as it contains a DNA containing a DNA having a base sequence encoding a protein containing the same or substantially the same amino acid sequence as represented by SEQ ID NO:5 or SEQ ID NO:11. The DNA encoding the MCH used in the present invention may be any DNA so long as it contains a DNA containing a DNA having a base sequence encoding a peptide containing the same or substantially the same amino acid sequence as represented by SEQ ID NO:2. Also, the DNA may be any one of genomic DNA, a genomic DNA library, cDNA derived from the cells or tissues described above, a cDNA library derived from the cells or tissues described above and synthetic DNA. The vector used for the library may be any of bacteriophage, plasmid, cosmid, phagemid, etc. In addition, the DNA can be directly amplified by reverse transcriptase polymerase chain reaction (hereinafter abbreviated as RT-PCR technology) using an RNA fraction prepared from the cells or tissues described above.

More specifically, there are employed (1) a DNA that is hybridizable under stringent conditions to the sequence possessed by a DNA containing a DNA having a base sequence encoding a protein or peptide containing the same or substantially the same amino acid sequence as the amino acid sequence represented by SEQ ID NO:2, SEQ ID NO:5 or SEQ ID NO:11, (2) a DNA that is not hybridizable due to degeneracy of genetic code to the sequence possessed by a DNA containing a DNA having a base sequence encoding a protein or peptide containing the same or substantially the same amino acid sequence as the amino acid sequence represented by SEQ ID NO:2, SEQ ID NO: 5 or SEQ ID NO:11 and to the sequence defined in (1) above but encoding a protein or peptide having the same amino acid sequence, etc. The hybridization can be carried out by publicly known methods or by modified known methods. The stringent conditions described above are, for example, conditions of 42° C., 50% formamide, 4×SSPE (1×SSPE= 150 mM NaCl, 10 mM NaH$_2$PO$_4$⁻H$_2$O, 1 mM EDTA, pH 7.4), 5× Denhardt's solution and 0.1% SDS.

The DNA encoding the SLC-1 or MCH used in the present invention can also be manufactured by the following genetic engineering techniques.

As a means for cloning of the DNA that fully encodes the SLC-1 or MCH of the present invention, the objective DNA may be selected by either amplification of the DNA from the DNA library, etc. supra by publicly known PCR using a synthetic DNA primer containing a partial base sequence of the SLC-1 or MCH of the present invention or, hybridization of the DNA inserted into an appropriate vector, e.g., with a labeled DNA fragment having a part or entire region of the base sequence encoding SLC-1 or MCH, or a labeled synthetic DNA. The hybridization can be carried out, for example, according to the method described in Molecular Cloning (2nd ed.; J. Sambrook et al., Cold Spring Harbor Lab. Press, 1989). When a commercially available library is used, the hybridization may be performed in accordance with the protocol described in the attached instructions.

The cloned DNA encoding the SLC-1 or MCH used in the present invention can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added to the DNA, using an appropriate synthetic DNA adapter.

The expression vector of the SLC-1 or MCH used in the present invention can be manufactured, for example, by (a) excising the objective DNA fragment from the DNA encoding the SLC-1 or MCH used in the present invention and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. The promoter used may be any promoter so long as it matches well with a host to be used for gene expression.

When animal cells are used as a host for transformation, there may be utilized SV40-derived promoter, retrovirus promoter, metallothionein promoter, heat shock promoter, cytomegalovirus promoter, SRα promoter, etc. Where the host is bacteria of the genus *Escherichia*, preferred examples include Trp promoter, T7 promoter, lac promoter, recA promoter, λPL promoter, 1pp promoter, etc. When bacteria of the genus *Bacillus* are used as the host, preferred examples are SPO1 promoter, SPO2 promoter, penP promoter, etc. When yeast is used as the host, preferred examples are PHO5 promoter, PGK promoter, GAP promoter, ADH1 promoter, GAL promoter, etc. When insect cells are used as the host, preferred examples include polyhedrin prompter, P10 promoter, etc.

In addition to the aforesaid examples, the expression vector that may further optionally contain an enhancer, a splicing signal, a polyA addition signal, a selection marker, SV40 replication origin (hereinafter sometimes abbreviated as SV40ori), etc. can be employed. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo; G418 resistance), etc. In particular, when DHFR gene is used as the selection marker using CHO (dhfr), selection may also be effected in a thymidine free medium.

If necessary and desired, a signal sequence that matches with a host is added to the N-terminal side of the polypeptide or its partial peptide. Examples of the signal sequence that can be utilized are pho A signal sequence, OmpA signal sequence, etc. when the host is bacteria of the genus *Escherichia*; α-amylase signal sequence, subtilisin signal sequence, etc. when the host is bacteria of the genus *Bacillus*; mating factor α (MFα) signal sequence, invertase signal sequence, etc. when the host is yeast; and insulin signal sequence, α-interferon signal sequence, antibody molecule signal sequence, etc. when the host is animal cells, respectively.

Using the vector containing the thus constructed DNA encoding the SLC-1 or MCH, transformants can be manufactured.

As the host, there may be employed, for example, bacteria belonging to the genus *Escherichia*, bacteria belonging to the genus *Bacillus*, yeast, insects or insect cells, animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)). HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207–21 (Journal of Biochemistry, 95, 87 (1984)), etc.

Examples of yeast include *Saccharomyces cerevisiae* AH22, AH22R, NA87-11A, DKD-5D, 20B-12, etc.

As the insect, for example, a larva of *Bombyx mori* can be used (Maeda et al., Nature, 315, 592 (1985)).

Examples of insect cells that are used include *Spodoptera frugiperda* cells (Sf cell), MG1 cells derived from mid-intestine of *Trichoplusia ni*, High Fives cells derived from egg of *Trichoplusia ni*, cells derived from Mamestra brassicae, cells derived from Estigmena acrea, etc. for AcNPV virus; and for BmNPV virus, *Bombyx mori* N cells (BmN cell), etc. Examples of the Sf cells which can be used are Sf9 cells (ATCC CRL1711), Sf21 cells [both cells are described in Vaughn, J. L. et al., In vitro, 13, 213–217 (1977)], etc.

Examples of animal cells include monkey COS-7 cells, Vero cells, Chinese hamster CHO cells, DHFR gene deficient Chinese hamster CHO cells (dhfr CHO cells), mouse L cells, mouse 3T3 cells, mouse myeloma cells, human HEK293 cells, human FL cells, 293 cells, C127 cells, BALB3T3 cells, Sp-2/O cells, etc.

Bacteria belonging to the genus *Escherichia* can be transformed, for example, by the method described in Proc. Natl. Acad. Sci. U.S.A., 69, 2110 (1972) or Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Proc. Natl. Acad. Sci. U.S.A., 75, 1929 (1978).

Insect cells or insects can be transformed, for example, according to the method described in Bio/Technology, 6, 47–55(1988), etc.

Animal cells can be transformed, for example, according to the method described in Virology, 52, 456 (1973).

Methods for introducing the expression vectors into the cells include, for example, the lipofection method [Felgner, P. L. et al., Proceedings of the National Academy of Sciences of the United States of America, 84, 7413 (1987)], the calcium phosphate method [Graham, F. L. and van der Eb, A. J., Virology, 52, 456–467 (1973)], the electroporation method [Nuemann, E. et al., EMBO J., 1, 841–845 (1982)], etc.

As described above, transformants transformed with the expression vector containing a DNA encoding the SLC-1 or MCH used in the present invention are obtained.

For stably expressing the SLC-1 or MCH used in the present invention with animal cells, there is applicable a method for selecting the cells by clone selection in which the expression vectors transfected to animal cells are incorporated into chromosomes. Specifically, the transformants are selected using as an index the selection marker described above. Further by repeating the clone selection on the animal cells thus obtained using the selection marker, the stable animal cell line capable of highly expressing the SLC-1 or MCH used in the present invention can be obtained. Furthermore, when the dhfr gene is used as the selection marker, cultivation can be performed by gradually increasing a level of MTX to select resistant cells so that the DNA encoding the SLC-1 or MCH used in the present invention can be amplified in the cells together with the dhfr gene to obtain the animal cell line of higher expression.

The transformant described above is cultivated under conditions in which the DNA encoding the SLC-1 or MCH used in the present invention can be expressed, to produce and accumulate the polypeptide of the present invention. Thus, the SLC-1 or MCH used in the present invention can be manufactured.

Where the host is a bacterium belonging to the genus *Escherichia* or the genus *Bacillus*, the transformant can be appropriately cultivated in a liquid medium which contains materials required for growth of the transformant, such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrates, corn steep liquor, peptone, casein, meat extract, soybean cake, potato extract, etc. Examples of the inorganics are calcium chloride, sodium dihydrogenphosphate, magnesium chloride, etc. In addition, yeast, vitamins, growth promoting factors, etc. may also be added to the medium. Preferably, pH of the medium is adjusted to about 5 to about 8.

A preferred example of the medium for cultivation of the bacteria belonging to the genus *Escherichia* is M9 medium supplemented with glucose and a asamino acid (Miller, Journal of Experiments in Molecular Genetics, 431-433, Cold Spring Harbor Laboratory, New York, 1972). If necessary and desired, a chemical such as 3β-indolylacrylic acid can be added to the medium thereby to activate the promoter efficiently.

Where the host is a bacterium belonging to the genus *Escherichia*, the transformant is usually cultivated at about 15 to about 43° C. for about 3 hours to about 24 hours. If necessary and desired, the culture may be aerated or agitated.

Where the host is a bacterium belonging to the genus *Bacillus*, the transformant is cultivated generally at about 30° C. to about 40° C. for about 6 hours to about 24 hours. If necessary and desired, the culture can be aerated or agitated.

Examples of media for cultivating the transformant whose host is a yeast include Burkholder's minimal medium [Bostian, K. L. et al., Proc. Natl. Acad. Sci. U.S.A., 77, 4505 (1980)) or in SD medium containing 0.5% casamino acid [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Examples of media for cultivating the transformant whose host is an insect cell include Grace's Insect Medium (Grace, T. C. C., Nature, 195, 788 (1962)) supplemented with 10% inactivated bovine serum, etc. as appropriate additives. Preferably, pH of the medium is adjusted to about 6.2 to about 6.4. Normally, the transformant is cultivated at about 27° C. for about 3 days to about 5 days and, if necessary and desired, the culture can be aerated or agitated.

Examples of media for cultivating the transformant whose host is an animal cell include MEM medium containing about 5% to about 20% fetal bovine serum [Science, 122, 501 (1952)), DMEM medium (Virology, 8, 396 (1959)], RPMI 1640 medium (The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

Especially when CHO(dhfr) cells and the dhfr gene are employed as the selection markers, it is preferred to use substantially thymidine-free DMEM supplemented with dialyzed bovine fetal serum.

The SLC-1 or MCH used in the present invention can be separated and purified from the culture described above by the following procedures.

For extracting the SLC-1 or MCH used in the present invention from the cultured bacteria or cells, publicly known methods can be used suitably, including a method in which transformants or cells are collected after cultivation, then suspended in an appropriate buffer and disrupted using ultrasonication, a treatment with lysozyme and/or freeze-thaw cycling, followed by centrifugation, filtration, etc. Thus, the crude extract of the SLC-1 or MCH used in the present invention can be obtained. The buffer used for the procedures may contain a protein denaturant such as urea or guanidine hydrochloride, or a surfactant such as Triton X-100 (trademark, hereinafter sometimes abbreviated as TM), etc.

When the SLC-1 or MCH used in the present invention is secreted in the culture broth, after completion of the cultivation the supernatant can be separated from the transformant or cell to collect the supernatant by a publicly known method.

The SLC-1 or MCH used in the present invention, which is contained in the thus-obtained culture supernatant or the extract, can be purified by appropriately combining the publicly known methods for separation and purification. Such known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charges such as ion exchange chromatography, etc.; a method utilizing specific affinity such as affinity chromatography, etc.; a method utilizing difference in hydrophobicity such as reverse phase high performance liquid chromatography, etc.; a method utilizing difference in isoelectric point such as isoelectric focusing, chromatofocusing, etc.; and the like.

When the SLC-1 or MCH used in the present invention thus obtained is in a free form, it can be converted into the salt by publicly known methods or modifications thereof. On the other hand, when the SLC-1 or MCH is obtained in a salt form, it can be converted into the free form or a different salt form by publicly known methods or modifications thereof.

The SLC-1 or MCH used in the present invention, which is produced by the recombinant, can be treated with an appropriate protein modifying enzyme prior to or after the purification to suitably modify the SLC-1 or MCH or partially delete a protein (peptide) therefrom. Examples of the protein modifying enzyme include trypsin, chymotrypsin, arginyl endopeptidase, protein kinase, glycosidase and the like. Also, for deletion of the N-terminal amino acid, the publicly known Edman method using Edman reagent (phenyl isothiocyanate) can be used.

The existence of the thus formed SLC-1 or MCH used in the present invention can be assayed by enzyme immunoassay using a specific antibody, or the like.

(2) A method for screening a compound or its salt that alters the binding property between the MCH or its salt and the SLC-1 or its salt, characterized by using the MCH or its derivative or a salt thereof and the SLC-1 or its salt, or a kit for screening a compound or its salt that alters the binding property between the MCH or its salt and the SLC-1 or its salt, characterized by using the MCH or its labeled form a salt thereof and the SLC-1 or its salt (hereinafter merely referred to as the screening methods of the present invention and the screening kits of the present invention, respectively) are described below in detail.

By using SLC-1 or its salt, or by constructing a expression system of recombinant SLC-1 and using a binding assay system (ligand/receptor assay system) between the MCH or its derivative or a salt thereof using the expression system, a compound or its salt that alters the binding property between the MCH or its salt and the SLC-1 or its salt (e.g., a peptide, a protein, a non-peptide compound, a synthetic compound, a fermentation product, etc.) can be screened.

Examples of such compounds include compounds showing SLC-1-mediated cell-stimulating activities (e.g., the activities that accelerate or suppress release of arachidonic acid, release of acetylcholine, release of intracellular $Ca^{2+}$, intracellular cAMP production, intracellular cGMP production, inositol phosphate production, changes in cell membrane potential, phosphorylation of intracellular proteins, activation of c-fos, pH reduction, etc.) (namely, SLC-1 agonists), compounds having no such cell-stimulating activities (namely, SLC-1 antagonists) and the like. The term "alters the binding property between the MCH or its salt and the SLC-1 or its salt" includes both cases that the binding property between MCH or its salt and SLC-1 or its salt is inhibited and binding to the ligand is accelerated.

That is, the present invention provides a method for screening a compound or its salt that alters the binding property between MCH or its salt and SLC-1 or its salt described above, which comprises comparing (i) the case that the MCH or its derivative or a salt thereof is brought into contact with the SLC-1 or its salt, and (ii) the case that the MCH or its derivative or a salt thereof and a test compound are brought into contact with the SLC-1 or its salt.

In the screening method of the present invention, the comparison is made by measuring, e.g., the amount of the ligand bound to the SLC-1 or its salt, the cell-stimulating activities, etc., (i) when the MCH or its derivative or a salt thereof is brought into contact with the SLC-1 or its salt, and (ii) when the MCH or its derivative or a salt thereof and a test compound are brought into contact with the SLC-1 or its salt; and comparing (i) and (ii).

More specifically, the screening method of the present invention provides the following features.

(1) A method for screening a compound or its salt that alters the binding property between MCH or its salt and SLC-1 or its salt, which comprises measuring and comparing the binding amounts of the labeled MCH or its derivative or a salt thereof bound to the aforesaid SLC-1 or its salt, when the labeled MCH or its derivative or a salt thereof (when using the aforesaid "labeled MCH, etc. or its salt" as the "MCH derivative or its salt", no further labeling is necessary; hereinafter the same) is brought in contact with the SLC-1 or its salt and when the labeled MCH or its derivative or a salt thereof and a test compound are brought in contact with the SLC-1 or its salt.

(2) A method for screening a compound or its salt that alters the binding property between MCH or its salt and SLC-1 or its salt, which comprises measuring and comparing the binding amounts of the labeled MCH or its derivative or a salt thereof bound to the SLC-1-containing cells or a membrane fraction of the cells, when the labeled MCH or its derivative or a salt thereof is brought in contact with the SLC-1-containing cells or a membrane fraction of the cells and when the labeled MCH or its derivative or a salt thereof and a test compound are brought in contact with the SLC-1 containing cells or a membrane fraction of the cells.

(3) A method for screening a compound or its salt that alters the binding property between MCH or its salt and SLC-1 or its salt, which comprises measuring and comparing the binding amounts of the labeled MCH or its derivative or a salt thereof bound to SLC-1, when the labeled MCH or its derivative or a salt thereof is brought in contact with the SLC-1 expressed on a cell membrane by culturing a transformant containing a DNA encoding SLC-1, and when the labeled MCH or its derivative or a salt thereof and a test compound are brought in contact with the SLC-1 expressed on a cell membrane by culturing a transformant containing a DNA encoding SLC-1.

(4) A method for screening a compound or its salt that alters the binding property between MCH or its salt and SLC-1 or its salt, which comprises measuring and comparing SLC-1-mediated cell stimulating activities (e.g., activities that accelerate or suppress release of arachidonic acid, release of acetylcholine, release of intracellular $Ca^{2+}$, intracellular cAMP production, intracellular cGMP production, inositol phosphate production, change in cell membrane potential, phosphorylation of intracellular proteins, activation of c-fos, pH reduction, etc.), when a compound for activating SLC-1 (e.g., MCH or its derivative or a salt thereof) is brought in contact with a SLC-1-containing cell and when a compound for activating SLC-1 and a test compound are brought in contact with the SLC-1 containing cell.

(5) A method for screening a compound or its salt that alters the binding property between MCH or its salt and SLC-1 or its salt, which comprises measuring and comparing SLC-1-mediated cell stimulating activities (e.g., activities that accelerate or suppress release of arachidonic acid, release of acetylcholine, release of intracellular $Ca^{2+}$, intracellular cAMP production, intracellular CGMP production, inositol phosphate production, change in cell membrane potential, phosphorylation of intracellular proteins, activation of c-fos, pH reduction, etc.), when a compound for activating SLC-1 (e.g., MCH or its derivative or a salt thereof) is brought in contact with the SLC-1 expressed on a cell membrane by culturing a transformant containing the DNA encoding the SLC-1 and when a compound for activating the SLC-1 and a test compound are brought in contact with the SLC-1 expressed on a cell membrane by culturing a transformant containing a DNA encoding SLC-1; and the like.

The screening method of the present invention is specifically described below.

First, the SLC-1 used for the screening method of the present invention may be any material so long as it contains the aforesaid SLC-1. Preferred SLC-1 includes membrane fractions from the organs of human, warm-blooded animals, fish, etc. Since it is very difficult to obtain human-derived organs, the SLC-1 expressed in large quantities by using recombinants is suitable for use in the screening. Particularly in human SLC-1, use of the SLC-1 containing the amino acid sequence shown by SEQ ID NO:11 can provide screening with good sensitivity, as compared to the SLC-1 represented by the previously reported amino acid sequence (FEBS Letters, 398 (1996) 253–258, etc.).

For manufacturing the SLC-1, the procedure described above may be used.

When the SLC-1-containing cells or cell membrane fractions, etc. are employed in the screening method of the present invention; the cells or cell membrane fractions may be prepared by the method which will be described hereinafter.

Where the SLC-1-containing cells are used, the cells may be fixed using glutaraldehyde, formalin, etc. The fixation can be made by publicly known methods.

The SLC-1-containing cells refer to host cells that have expressed SLC-1. Examples of host cells include *Escherichia coli, Bacillus subtilis*, yeast, insect cells, animal cells, etc., described above.

The membrane fraction refers to a fraction abundant in cell membrane obtained by publicly known methods after cell disruption. Useful cell disruption methods include cell squashing using a Potter-Elvehjem homogenizer, disruption using a Waring blender or a polytron (manufactured by Kinematica Inc.), disruption by ultrasonication, and disruption by spraying cells through thin nozzles under an increased pressure using a French press or the like. Cell membrane fractionation is effected mainly by fractionation using a centrifugal force, such as fractionation centrifugation, density gradient centrifugation, etc. For example, cell disruption fluid is centrifuged at a low speed (500 rpm to 3,000 rpm) for a short period of time (normally about 1 minute to about 10 minutes) and, the resulting supernatant is centrifuged at a higher speed (15,000 rpm to 30,000 rpm) normally for 30 minutes to 2 hours. The precipitate thus obtained is used as the membrane fraction. The membrane fraction is rich in the SLC-1 expressed and membrane components such as cell-derived phospholipids and membrane proteins.

The amount of SLC-1 in the SLC-1-containing cells or in the membrane fractions is preferably $10^3$ to $10_8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of sample fluids can be assayed with the same lot.

To perform the above (1) through (3) for screening the compound that alters the binding property between. MCH or its salt and SLC-1, an appropriate SLC-1 fraction and a labeled ligand or a compound containing a ligand activity (MCH or its derivative) are employed. The SLC-1 fraction is preferably a naturally occurring SLC-1 fraction or a recombinant SLC-1 fraction having an activity equivalent to that of the natural SLC-1 fraction. Herein, the term "equivalent activity" is intended to mean a ligand binding activity or the like, equivalent to that of the natural SLC-1 fraction. As the labeled ligand or the compound having a ligand activity, there are used a labeled ligand and a compound having a ligand activity (MCH or its derivative), etc. For example, a ligand (MCH or its derivative) which is labeled with [$^3$H], [$^{125}$I], [$^{14}$C], [$^{35}$S], etc. can be utilized. In particular, the labeled form of the MCH derivative prepared by a publicly known method using a Bolton-Hunter reagent may also be utilized.

Specific examples of the labeled form of the MCH derivatives are compounds given in (1) through (7) described above.

Specifically, the compound that alters the binding property between MCH or its salt and SLC-1 is screened by the following procedures. First, a standard receptor preparation is prepared by suspending SLC-1-containing cells or membrane fractions of such cells in a buffer appropriate for screening. Any buffer can be used so long as it does not interfere with ligand-receptor binding, such buffers including a phosphate buffer, a Tris-HCl buffer, etc. showing pH of 4 to 10 (desirably pH of 6 to 8). For the purpose of reducing non-specific binding, a surfactant such as CHAPS, Tween-80™ (Kao-Atlas Inc.), digitonin, deoxycholate, etc. may optionally be added to the buffer. Further for the purpose of suppressing the degradation of SLC-1 and MCH or its derivative caused by a protease, a protease inhibitor such as PMSF, leupeptin, E-64 (manufactured by Peptide Institute, Inc.), pepstatin, etc. may also be added. A given amount (5,000 cpm to 500,000 cpm) of the labeled MCH or its derivative is added to 0.01 ml to 10 ml of the receptor solution and at the same time, a test compound of $10^{-4}$ to $10^{-1}$ $\mu$M is allowed to be co-present. To determine the amount of non-specific binding (NSB), a reaction tube added with unlabeled MCH or its derivative in a large excess is also prepared. The reaction is carried out at approximately 0° C. to 50° C., preferably 4° C. to 37° C. for 20 minutes to 24 hours, preferably. 30 minutes to 3 hours. After completion of the reaction, the reaction mixture is filtrated through a glass fiber filter paper, etc. and washed with a suitable volume of the same buffer. The residual radioactivity retained on the glass fiber filter paper is then measured with a liquid scintillation counter or a γ-counter. When a count (B-NSB$_0$) obtained by subtracting non-specific binding (NSB) from a count (B$_0$) in the absence of an antagonistic substance is taken as 100%, the test compound giving a non-specific binding (B-NSB) of, e.g., 50% or less can be selected as a candidate substance having a competitive inhibitory activity.

For assaying the binding between SLC-1 and MCH or its derivative, BIAcore (manufactured by Amersham Pharmacia Biotech Co.) may also be employed. In this technique, the MCH or its derivative is immobilized onto a sensor chip by the amino coupling method following the protocol attached to the device. A buffer such as phosphate buffer, Tris buffer, etc., which contains SLC-1 purified from the SLC-1-containing cells or a transformant containing a DNA encoding SLC-1, or a membrane fraction containing SLC-1 or, the purified SLC-1 or a membrane fraction containing SLC-1 and a test compound, is passed over the sensor chip at a flow rate of 2 to 20 $\mu$l/min. By monitoring that the test compound co-present alters the change in surface plasmon resonance caused by binding of MCH or its derivative on the sensor chip to SLC-1, the compound that alters the binding between SLC-1 and MCH can be screened. According to this technique, the alteration can be likewise measured by the procedure which involves immobilizing SLC-1 onto a sensor chip and passing over the sensor chip a buffer solution such as phosphate buffer, Tris buffer, etc., which contains MCH or its derivative or MCH or its derivative and a test compound. Examples of the test compound are the same as those given above.

The procedure (4) or (5) described above for screening the compound that alters the binding property between MCH or its salt and SLC-1 or its salt can be performed as follows. The SLC-1-mediated cell-stimulating activities (e.g., the activities that promote or suppress release of arachidonic acid, release of acetylcholine, release of intracellular Ca$^{2+}$, intracellular cAMP production, intracellular cGMP production, inositol phosphate production, change in cell membrane potential, phosphorylation of intracellular proteins, activation of c-fos, pH reduction, etc.) may be assayed by a publicly known method, or using an assay kit commercially available. Specifically, the SLC-1-containing cells are first cultivated on a multiwell plate, etc. Prior to screening, the medium is replaced with a fresh medium or with an appropriate non-cytotoxic buffer, followed by incubation for a given period of time in the presence of a test compound, etc. Subsequently, the cells are extracted or the supernatant is recovered. The formed product is quantified by the respective procedures. Where it is difficult to detect the production of the index substance (e.g., arachidonic acid) for the cell-stimulating activities due to degrading enzymes contained in the cells, an inhibitor against such a degradation enzyme may be added prior to the assay. For detecting activities such as the cAMP production inhibitory activity, the baseline production in the cells is increased by forskolin or the like. Then, the suppressing effect on the increased baseline production can be detected.

For screening by assaying the cell-stimulating activities, a suitable cell in which SLC-1 has been expressed is required. Such a cell that the SLC-1 of the present invention has been expressed is desirably the aforesaid recombinant SLC-1-expression cell line, and the like. The SLC-1-expression cell may be either a stably expressed strain or a transiently expressed strain. Also, kind of animal cells is the same as those given above.

Examples of the test compound include a peptide, a protein, a non-peptide compound, a synthetic compound, a fermentation product, a cell extract, a plant extract, an animal tissue extract and the like.

In more detail, the following assay system employed for the ligand-receptor assay system supra is described below.

(1) When a receptor expression cell is stimulated by a receptor agonist, G protein in the cell is activated and GTP is bound thereto. This phenomenon is observed also in a membrane fraction of the receptor expression cell. Usually, GTP is hydrolyzed into GDP. However, when GTPyS is previously added to the reaction solution, GTPyS is bound to G protein as in GTP but is not hydrolyzed so that a state of GTPγS bound to the G protein-containing cell membrane is maintained. When labeled GTPγS is used, the residual radioactivity on the cell membrane is measured, whereby the receptor expression cell stimulating activity of a receptor agonist can be assayed. Using this reaction, the stimulating activity of MCH or its derivative on the SLC-1 expression cells can be assayed. This is an assay method using the SLC-1-containing membrane fraction as described in (1) through (3), not using the SLC-1-containing cells as in (4) and (5) described above. According to this method, however, the cell stimulating activity is assayed as in (4) and (5). In this assay system, the substance showing the GTPγS binding promoting activity to the SLC-1 membrane fraction is an agonist. Specifically, the assay is carried out following the procedures of EXAMPLES 9 and 16, which will be later described, as well as their modifications. Herein, the compound that alters the binding property between MCH and SLC-1 can be screened by adding MCH or its derivative or MCH or its derivative and a test compound and monitoring that the GTPγS binding promoting activity to the SLC-1 membrane fraction alters, when compared to administration of MCH or its derivative alone. In this case, the compound that shows suppression of the GTPγS binding promoting activity of the MCH or its derivative to the SLC-1 membrane fraction can be selected as a candidate substance having a competitive inhibitory activity. On the other hand, an agonist can be screened by administering the test compound alone and monitoring the GTPγS binding promoting activity to the SLC-1 membrane fraction.

An example of the screening method is specifically described below. The cell membrane fraction containing human or rat SLC-1, which is prepared by the procedure described later in EXAMPLE 9 or 16, is diluted with a buffer for membrane dilution (50 mM Tris, 5 mM MgCl$_2$, 150 mM NaCl, 1 µM GDP, 0.1% BSA, pH 7.4). A degree of dilution varies depending upon the amount of a receptor expressed. The dilution is dispensed by 0.2 ml each in Falcon 2053, to which MCH or its derivative or MCH or its derivative and a test compound are added. [$^{35}$S]GTPγS is added to the mixture to a final concentration of 200 pM. After maintaining at 25° C. for an hour, ice-cooled wash buffer (50 mM Tris, 5 mM MgCl$_2$, 150 mM NaCl, 0.1% BSA, 0.05% CHAPS, pH 7.4, 1.5 ml) is added to the mixture followed by filtration through a glass fiber filter paper GF/F. After keeping at 65° C. for 30 minutes, the mixture is dried and the radioactivity of [35S] GTPγS bound to the membrane fraction remaining on the filter paper is measured with a liquid scintillation counter. When the radioactivity in the experimental group added with MCH or its derivative alone is defined as 100% and the radioactivity in the experimental group added with neither MCH nor its derivative is defined as 0%, an effect of the test compound on the GTPγS binding promoting activity by MCH or its derivative is worked out. The test compound showing the GTPγS binding promoting activity of, for example, 50% or less can be selected as a candidate compound having a competitive inhibitory activity.

(2) In the SLC-1 expression cells, an amount of intracellular cAMP decreases by MCH stimulation. Utilizing this reaction, the stimulating activity of MCH on the SLC-1 expression cells can be assayed.

The amount of cAMP production in various animal cells in which SLC-1 has been expressed can be assayed by RIA using an anti-cAMP antibody, whose antibody is obtained from immunized mouse, rat, rabbit, goat, bovine, etc., and $^{125}$I-labeled cAMP (both commercially available) or by other EIA system using an anti-cAMP antibody and labeled cAMP in combination. Quantification by the SPA technique is also possible, in which beads containing scintillants bearing anti-cAMP antibodies immobilized using protein A or antibodies to IgG, etc. of animal used to produce the anti-cAMP antibodies and $^{125}$I-labeled cAMP are used (a kit manufactured by Amersham Pharmacia Biotech is used).

The inhibition of cAMP production is assayed specifically by the procedure of EXAMPLE 14 later described or by its modification. In this system, the compound that alters binding of the MCH to the SLC-1 can be screened by increasing the amount of intracellular cAMP by such a ligand as forskolin or calcitonin capable of increasing the amount of intracellular cAMP and monitoring that suppression of the intracellular cAMP production by administration of MCH or its derivative alone is altered by adding MCH or its derivative or MCH or its derivative and a test compound. In this case, the compound that shows an activity of inhibiting the cAMP production inhibitory activity by MCH or its derivative can be selected as a candidate substance having a competitive inhibitory activity. On the other hand, a compound showing an agonist activity can be screened by monitoring the cAMP production inhibitory activity when a test compound alone is added.

The screening method is described below more specifically. CHO/SLC-1 cells are inoculated on a 24-well plate in 5×10$^4$ cells/well followed by cultivation for 48 hours. The cells are washed with Hanks' balanced salt solution (pH 7.4) containing 0.2 mM 3-isobutylmethylxanthine, 0.05% BSA and 20 mM HEPES (hereinafter Hanks' balanced salt solution (pH 7.4) containing 0.2 mM 3-isobutylmethylxanthine, 0.05% BSA and 20 mM HEPES is referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 nM MCH or its derivative or 1 nM MCH or its derivative and a test compound is/are added to 0.25 ml of the reaction buffer containing 2 μM forskolin. The mixture is added to the cells followed by reacting at 37° C. for 24 minutes. The reaction is terminated by adding 100 μl of 20% perchloric acid. The reaction mixture is then put on ice for an hour to extract intracellular cAMP. The amount of cAMP in the extract is measured using a CAMP EIA kit (Amersham Pharmacia Biotech). Taking the amount of cAMP produced by forskolin stimulation as 100% and the amount of cAMP inhibited by the addition of nM MCH or its derivative as 0%, an effect of the test compound on the cAMP production inhibitory activity by MCH or its derivative is calculated. A test compound that inhibits the activity of the MCH or its derivative to reduce the cAMP production activity, e.g., to 50% or more can be selected as a candidate substance having a competitive inhibitory activity.

To determine the cAMP production promoting activity, the amount of cAMP produced by adding a test compound to CHL/SLC-1 cells without adding forskolin is quantified by the procedure described above.

(3) A DNA containing CRE (CAMP response element) is inserted into a multicloning site upstream a luciferase gene in a PicaGene Basic Vector or a PicaGene Enhancer Vector (Toyo Ink Mfg. Co., Ltd.), which is made a CRE-reporter gene vector. In a CRE-reporter gene vector-transfected cell, stimulation associated with increase cAMP induces expression of CRE-mediated luciferase gene and luciferase protein production subsequent thereto. That is, by assaying the luciferase activity, a change in amount of cAMP in the CRE-reporter gene vector transfected cell can be detected. Utilizing the SLC-1-expression cell to which the CRE-reporter gene vector is transfected, a compound that alters the binding between MCH and SLC-1 can be screened. The screening method is specifically described below.

The CRE-reporter gene transfected SLC-1 expression cells are inoculated on a 24-well plate in $5 \times 10^3$ cells/well followed by cultivation for 48 hours. The cells are washed with Hanks' balanced salt solution (pH 7.4) containing 0.2 mM 3 isobutylmethylxanthine, 0.05% BSA and 20 mM HEPES (hereinafter Hanks' balanced salt solution (pH 7.4) containing 0.2 mM 3-isobutylmethylxanthine, 0.05% BSA and 20 mM HEPES is referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 nM MCH or its derivative or 1 nM MCH or its derivative and a test compound as well as 0.25 ml of the reaction buffer containing 2 μM forskolin are added to the cells followed by reacting at 37° C. for 24 minutes. The cells are dissolved in a cell lysis agent for PicaGene (Toyo Ink Mfg. Co., Ltd.) and a luminescence substrate (Toyo Ink Mfg. Co., Ltd.) is added to the lysate. Luminescence emitted by luciferase is measured by a luminometer, a liquid scintillation counter or a top counter. An effect of the compound that alters the binding between MCH and SLC-1 can be assayed by comparing the luminescence amounts of luciferase with the case where MCH or its derivative is administered solely. In this case, an increase of the luminescence amount by forskolin stimulation is suppressed by administration of MCH or its derivative. The compound that can retrieve the inhibition can be selected as a candidate substance having a competitive inhibitory activity. On the other hand, an agonist can be screened as well by administering a test compound alone and monitoring suppression of the luminescence amount intensified by forskolin stimulation in the same way as in the MCH or its derivative.

In addition to luciferase, alkaline phosphatase, chloramphenicol acetyltransferase or β-galactosidase may be employed as the reporter gene. The enzymatic activity of gene products from these reporter genes can be readily assayed using assay kits commercially available. The alkaline phosphatase activity, the chloramphenicol acetyltransferase activity and the β-galactosidase activity can be assayed, e.g., using Lumi-Phos 530, FAST CAT chloramphenicol acetyltransferase Assay Kit and Aurora Gal-XE, respectively, all manufactured by Wako Pure Chemical Industries.

(4) The SLC-1 expression cells extracellularly release arachidonic acid metabolites as a result of MCH-stimulation. By previously incorporating radioactive arachidonic acid into the cells, the activity can be assayed by measuring the radioactivity released outside the cells. The assay is carried out by the procedure of EXAMPLE 6 later described and its modification. In this case, the compound that affects the arachidonic acid metabolite releasing activity by MCH or its derivative can be screened by adding MCH or its derivative or MCH or its derivative and a test compound and monitoring an effect of the MCH or its derivative on the arachidonic acid metabolite releasing activity. In this case, the compound that inhibits the arachidonic acid metabolite releasing activity by the MCH or its derivative can be selected as a candidate substance having a competitive inhibitory activity. On the other hand, a compound showing an agonist activity can be screened as well by administering a test compound alone and monitoring the arachidonic acid metabolite releasing activity by the SLC-1 expression cells by the procedure modified from EXAMPLE 6 later described. The method for screening a compound that affects the binding between MCH and SLC-1 is described below more specifically.

CHO/SLC-1 cells are inoculated on a 24-well plate in $5 \times 10^4$ cells/well. After cultivation for 24 hours, [$^3$H] arachidonic acid is added to the cells in 0.25 μCi/well. Sixteen hours after the addition of [$^3$H] arachidonic acid, the cells are washed with Hanks' balanced salt solution (pH 7.4) containing 0.05% BSA and 20 mM HEPES. To each well is added 500 μl of a solution obtained by dissolving a 10 nM final concentration of MCH or its derivative or a 10 nM final concentration of MCH or its derivative and a test compound in Hanks' balanced salt solution (pH 7.4) containing 0.05% BSA and 20 mM HEPES. Hereinafter Hanks' balanced salt solution (pH 7.4) containing 0.05% BSA and 20 mM HEPES is referred to as a reaction buffer. After incubating 37° C. for 60 minutes, 400 μl of the reaction solution is charged in a scintillator and the amount of [$^3$H] arachidonic acid metabolites released in the reaction solution is measured using a scintillation counter. When the amount of [$^3$H]arachidonic acid metabolites in the medium of the reaction buffer added with neither MCH nor its derivative is taken as 0% and the amount of [$^3$H] arachidonic acid metabolites in the medium added with 10 nM of MCH or its derivative is taken as 100%, an effect of the test compound on the binding between MCH or its derivative and SLC-1 is calculated. The test compound that reduces the arachidonic acid metabolite producing activity, e.g., to 50% or less can be selected as a candidate substance having a competitive inhibitory activity.

(5) When the SLC-1 expression cells are stimulated by MCH, an intracellular Ca level increases. Utilizing such, an effect of a test compound on the binding between MCH and SLC-1 can be monitored.

The SLC-1 expression cells are inoculated on a sterilized cover glass for microscopy. Two days after, the culture medium is replaced by HBSS in which 4 mM Fura-2 AM (Doj in Kagaku Kenkyusho) is suspended, followed by standing at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when MCH or its derivative or MCH or its derivative and a test compound is/are added. In this case, the compound that affects the binding between MCH and SLC-1 can be screened by measuring a change in fluorescence intensity caused by addition of the test compound, as compared to the case where MCH or its derivative is administered solely. Also, FLIPR (manufactured by Molecular Device Co.) may be used as described below. That is, Fluo-3 AM (manufactured by Dojin Kagaku Kenkyusho) is added to a cell suspension to incorporate Fluo-3 AM into the cells. The supernatant is washed several times through centrifugation and the cells are inoculated on a 96-well plate. After setting in the FLIPR device, MCH or its derivative or MCH or its derivative and a test compound is/are added as in Fura-2. The compound that affects the binding between MCH and SLC-1 can be screened by measuring a change in fluorescence intensity caused by addition of the test compound, as compared to the case where MCH or its derivative is administered solely. In these cases, the compound that inhibits an increase of fluorescence intensity by MCH or its derivative can be selected as a candidate substance having a competitive inhibitory activity. On the other hand, an agonist can be screened by monitoring an increase of fluorescence intensity when adding the test compound alone.

In the SLC-1 expression cells, when a protein gene such as aequorin that emits light in association with an increase of intracellular Ca ions is co-expressed and aequor in changes to Ca-bound aequorin by an increase of intracellular Ca ion level to emit light. Utilizing this light emission, the compound that affects the binding between MCH and SLC-1 can be screened by adding MCH or its derivative or MCH or its derivative and a test compound and, monitoring that light emission observed by addition of the test compound changes, as compared to the case where the MCH or its derivative alone is administered. The method is the same as described above, except that the fluorescent substance is not incorporated into the cells.

(6) It is known that when a receptor agonist is added to a receptor-expressing cell, a level of intracellular inositol triphosphate increases. By monitoring the reaction in the SLC-1 cells caused by MCH, the compound that affects the binding between MCH and SLC-1 can be screened. On one day after inoculation of the cells on a 24-well plate, myo-[2³H]inositol (2.5 microCi/well) is added to each well. In this medium the cells are cultivated for one day. After thoroughly washing, MCH or its derivative or MCH or its derivative and a test compound is/are added to the cells. The reaction is then terminated by adding 10% perchloric acid. The reaction mixture is neutralized with 1.5 M KOH and 60 mM HEPES solution and then passed through a column packed with 0.5 ml of Ag1×8 resin (Bio-Rad). After washing with 5 mM $Na_2BO_3$ and 60 mM $HCOONH_4$, the radioactivity eluted with 1M $HCOONH_4$ and 0.1M HCOOH is measured with a liquid scintillation counter. When the radioactivity in the medium of the reaction buffer without adding MCH or its derivative is made 0% and the radioactivity in the medium added with MCH or its derivative is made 100%, an effect of the test compound on the binding between the MCH or its derivative and SLC-1 is calculated. The test compound that inhibits the inositol triphosphate production activity, e.g., to 50% or less can be selected as a candidate substance having a competitive inhibitory activity. On the other hand, an agonist can be screened as well by monitoring an increase of the inositol triphosphate production activity when adding the test compound alone.

(7) A DNA containing TRE (TPA response element) is inserted into a multicloning site upstream a luciferase gene in a PicaGene Basic vector or a PicaGene Enhancer Vector (Toyo Ink Mfg. Co., Ltd.), which is made a TRE-reporter gene vector. In a TRE-reporter gene vector-transfected cell, stimulation accompanied by an increase of intracellular Ca induces expression of TRE-mediated luciferase gene and the following luciferase protein production. That is, by assaying the luciferase activity, a change in amount of calcium in the TRE-reporter gene vector transfected cell can be detected. Utilizing the TRE-reporter gene vector-transfected SLC-1 expression cells, a compound that alters the binding between MCH and SLC-1 can be screened. The screening method is specifically described below.

The TRE-reporter gene-transfected SLC-1 expression cells are inoculated on a 24-well plate in $5 \times 10^3$ cells/well followed by cultivation for 48 hours. After the cells are washed with Hanks' balanced salt solution (pH7.4) containing 0.05% BSA and 20 mM HEPES, 10 nM of MCH or its derivative or 10 nM of MCH or its derivative and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured by a luminometer, a liquid scintillation counter or a top counter. An effect of the compound that alters the binding between MCH and SLC-1 can be measured by comparing the luminescence amount by luciferase with the case when adding MCH or its derivative alone. In this case, the amount of luminescence increases with an increase in intracellular Ca by administration of MCH or its derivative and the compound that suppresses the increase can be selected as a candidate substance having a competitive inhibitory activity. On the other hand, an agonist can be screened as well by monitoring an increase of luminescence in the same way as in MCH or its derivative, when the test compound alone is administered.

In addition to luciferase, alkaline phosphatase, chloramphenicol acetyltransferase or β-galactosidase may be employed as the reporter gene. The enzymatic activity of gene products from these reporter genes can be easily assayed as described below, using assay kits commercially available. The alkaline phosphatase activity, the chloramphenicol acetyltransferase activity and the β-galactosidase activity can be assayed, e.g., using Lumi-Phos 530, FAST CAT chloramphenicol Acetyltransferase Assay Kit and Aurora Gal-XE, respectively, all manufactured by Wako Pure Chemical Industries Co., Ltd.

(8) In the SLC-1 expression cells in response to MCH, growth is observed by MAP kinase activation. This growth can be assayed by the MAP kinase activity, thymidine uptake or cell counting (MTT, etc.). Utilizing such, the compound that alters the binding between the MCH or its derivative and the SLC-1 can be screened.

The MAP kinase activity can be readily assayed by adding MCH or its derivative or MCH or its derivative and a test compound to the cells, obtaining a MAP kinase fraction from a cell lysate by immuno precipitation using an anti-MAP kinase antibody and then using, e.g., a MAP Kinase Assay Kit manufactured by Wako Pure Chemical Industries Co., Ltd. and $\gamma$-[$^{32}$P]-ATP. The thymidine uptake activity can be assayed by inoculating the SLC-1 expression cells, adding MCH or its derivative or MCH or its derivative and a test compound to the cells, further adding [methyl-$^3$H]-thymidine, causing cell lysis and then counting the radioactivity of the labeled thymidine taken up into the cells with a liquid scintillation counter.

The growth of the SLC-1 expression cells can be determined as well by inoculating the expression cells, adding MCH or its derivative or MCH or its derivative and a test compound, further adding MTT (3-(4,5-dimethyl-2-thiazolyl)-2,5-diphenyl-2H-tetrazoli um bromide), taking MTT up into the cells thereby to convert into MTT formazan, causing cell lysis with isopropanol which is rendered acidic with hydrochloric acid, and then measuring absorption at 570 nm.

The method for screening the compound that alters the binding between MCH and SLC-1 utilizing the labeled thymidine uptake activity is described below specifically.

The SLC-1 expression cells are inoculated on a 24-well plate in 5000 cells/well followed by incubation for one day. Next, the cells are incubated in a serum-free medium for 2 days to bring the cells under starvation. MCH or its derivative or MCH or its derivative and a test compound is/are added to the cells. After incubation for 24 hours, [methyl-3H) thymidine is added in 0.015 MBq/well followed by incubation for 6 hours. After washing the cells with PBS, methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with 0.3N sodium hydroxide solution, the radioactivity in the lysate is measured with a liquid scintillation counter. An effect of the compound that alters the binding between MCH and SLC-1 can be determined by comparing with an increase of the radioactivity by thymidine uptake when MCH or its derivative alone is administered. In this case, the compound that suppresses an increase of the radioactivity by administering MCH or its derivative can be selected as a candidate substance having a competitive inhibitory activity. On the other hand, an agonist can be screened by monitoring an increase of the radioactivity in the same way as in the MCH or its derivative when the test compound alone is administered.

(9) When MCH is added to the SLC-1 expression cells, K channel is activated so that K ions present within the cells are effluxed extracellularly. Since Rb ions in the related elements to K ions flow out of the cells through the K channel without being distinguished from K ions, labeled Rb ([$^{86}$Rb]) is added to the cells to permit intracellular uptake of the isotope. Then, the efflux of [$^{86}$Rb]) that flows out by MCH stimulation is measured to assay the action of MCH. The method for screening the compound that alters the binding between MCH and SLC-1 utilizing [$^{86}$Rb] efflux activity is described below specifically.

Two days after inoculation on 24 wells the SLC-1 expression cells are kept warm for 2 hours in a medium containing 1 mCi/ml of $^{86}$RbC1. The medium is thoroughly washed to completely remove $^{86}$RbC1 in the outer liquid. MCH or its derivative or MCH or its derivative and a test compound are added to the cells. The outer liquid is recovered 30 minutes later and the radioactivity is counted with a γ counter. An effect of the compound that alters the binding between MCH or its derivative and SLC-1 can be assayed by comparing an increase of the radioactivity by [$^{86}$Rb] efflux with the case when MCH or its derivative alone is administered. In this case, the compound that suppresses an increase of the radioactivity by administration of MCH or its derivative can be selected as a candidate substance having a competitive inhibitory activity. On the other hand, an agonist can be screened as well by monitoring an increase of the radioactivity in the same way as in the MCH or its derivative when the test compound alone is administered.

(10) The MCH activity can be assayed by measuring extracellular pH (acidification rate) that the SLC-1 expression cells changes in response to MCH, using a Cytosensor device (Molecular Device Co.). The method for screening the compound that alters the binding between MCH and SLC-1 through the extracellular pH measurement using the Cytosensor device is specifically described below.

The SLC-1 expression cells are incubated overnight in a capsule for the Cytosensor device, which is set in a chamber of the device to reflux 0.1% BSA-containing RPMI 1640 medium (manufactured by Molecular Device Co.) until the extracellular pH becomes stable. After the pH becomes stable, a medium containing MCH or its derivative or MCH or its derivative and a test compound is refluxed on the cells to measure a change in pH caused thereby. An effect of the compound that alters the binding between MCH or its derivative and SLC-1 can be assayed by comparing a change of extracellular pH in the SLC-1 expression cells with the case when the MCH or its derivative is administered solely. In this case, the compound that suppresses a change of extracellular pH in the SLC-1 expression cells by administering MCH or its derivative can be selected as a candidate substance having a competitive inhibitory activity. On the other hand, an agonist can be screened by monitoring a change of extracellular pH in the same way as in the MCH or its derivative when the test compound alone is administered.

(11) In *Saccharomyces Cerevisiae*, sex pheromone receptor STe2 of haploid α-mating type (MATα) is coupled to G protein Gpal to activate MAP kinase in response to sex pheromone α-mating factor, whereby Far1 (cell-cycle arrest) and transcription activator Ste12 are activated. Ste12 stimulates expression of a wide variety of genes, including FUS1 which is associated with mating. On the other hand, regulator Sst2 functions to inhibit the foregoing process. In this system, an attempt has been made on an assay system for the receptor agonist/receptor reaction, which involves producing a receptor gene-integrated yeast, activating the signal transduction system in yeast cells by receptor agonist stimulation and using the resulting growth, etc. as an index (Pausch, M. H., Trends in Biotechnology, vol. 15, pp. 487–494 (1997)). Utilizing such a receptor gene-integrated yeast system, the compound that alters the binding between MCH and SLC-1 can be screened.

Ste2 in MATα yeast and a gene encoding Gpal are removed and instead, SLC-1 gene and a gene encoding Gpa1-Gai2 fused protein are introduced. A gene encoding Far is removed to cause no cell-cycle arrest and a gene encoding Sst is removed to increase the sensitivity in response to MCH. Furthermore, FUS1-HIS3 gene, which is FUS1 ligated with histidine biosynthesis gene HIS3, is introduced. The foregoing genetic recombinant engineering can be easily performed, e.g., by the method reported by Price et al. (Price, L. A. et al., Molecular and Cellular Biology, vol. 15, pp. 6188–6195 (1995)), using SLC-1 in place of somatostatin receptor type 2 (SSTR2) gene. The thus constructed transformant yeast is responsive to MCH as a ligand to SLC-1 in a high sensitivity so that MAP kinase is activated and a histidine biosynthesis enzyme is synthesized. Thus, the transformant becomes capable of growing in a histidine-deficient medium. Utilizing such, response of the SLC-1-expressed yeast by MCH can be monitored using as an index growth of the yeast in a histidine-deficient medium. The method for screening the compound that alters the binding between MCH and SLC-1 is described below.

The thus produced transformant yeast is incubated overnight in complete synthesis liquid medium and added to a histidine-free soft agar medium in $2\times10^4$ cells/ml, followed by inoculation on a square Petri dish of 9×9 cm. After the agar is solidified, a sterilized filter paper impregnated with MCH or its derivative or MCH or its derivative and a test compound is put on the agar surface, followed by incubating at 30° C. for 3 days. An effect of the compound that alters the binding between MCH or its derivative and SLC-1 can be assayed by comparing growth of yeast around the filter paper with the case when the MCH or its derivative is administered solely. In this case, the compound that suppresses the growth of yeast by administration of MCH or its derivative can be selected as a candidate substance having a competitive inhibitory activity. On the other hand, an agonist can be screened as well by monitoring the growth of yeast in the same way as in MCH or its derivative when the test compound alone is administered. Also, the compound that alters the binding between MCH or its derivative and SLC-1 can also be assayed by previously adding the MCH or its derivative to the agar medium, impregnating a sterilized filter paper with a test compound alone, incubating and monitoring that the growth of yeast over the entire surface of the Petri dish is affected at the periphery of the filter paper.

(12) When the SLC-1 gene RNA is injected into *Xenopus laevis* oocytes are stimulated by MCH, an intracellular Ca ion level increases to cause a calcium-activated chloride current, which can be grasped as fluctuation in membrane potential (same as in the case where fluctuation occurs in a K ion level gradient). By monitoring the above reaction in the SLC-1-introduced *Xenopus laevis* oocytes caused by MCH, the compound that affects the binding between MCH and SLC-1 can be screened.

A female individual of *Xenopus laevis* is anesthetized by immersing in ice water and anatomized for taking out oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES, pH 7.4) at 19° C. for 1 to 6 hours at 150 rpm, until the oocytes are separated one from another. Washing is performed 3 times by replacing the outer liquid by the MBS solution followed by microinjection of poly(A)$^+$ SLC-1 cRNA (50 ng/50 nl) with a micro manipulator. SLC-1 mRNA may be prepared from tissues or cells or transcribed from plasmids in vitro. The oocytes are incubated in the MBS solution at 20° C. for 3 days. The oocytes are placed in a hole of a voltage clamp device, which is continuously perfused with Ringer's solution, and impaled with a glass micro electrode for voltage clamp and a glass micro electrodes for recording, in which (−) electrode is placed outside the oocytes. When the holding potential stabilizes, Ringer's solution containing MCH or its derivative or MCH or its derivative and a test compound is perfused to record a change in potential. An effect of the compound that alters the binding between MCH and SLC-1 can be measured by comparing a change in cell membrane potential of the SLC-1-introduced *Xenopus laevis* oocytes with the case when the MCH or its derivative alone is administered. In this case, the compound that suppresses a change in cell membrane potential caused by administration of the MCH or its derivative can be selected as a candidate substance having a competitive inhibitory activity. On the other hand, an agonist can be screened as well by monitoring the change in cell membrane potential in the same way as in the MCH or its derivative where the test compound alone is administered.

In this system, the amount of alteration may be increased by introducing poly(A)$^+$ RNAs of various G protein genes so that it becomes easier to monitor the reaction. Also, the reaction can be assayed by co-injecting poly(A)$^+$ RNAs to a gene of a protein such as aequorin that emits light in the presence of Ca and monitoring the light emission, not a change in membrane potential.

The kits for screening a compound or its salts that alter the binding property between MCH or its salts and SLC-1 or its salts comprises SLC-1 or its salts, SLC-1-containing cells or SLC-1-containing cell membrane fractions and MCH or its derivatives or salts thereof.

The screening kits according to the present invention comprise, for example, the following:

1. Reagents for Screening
(1) Buffers for Assay and Washing

Hanks' Balanced Salt Solution (manufactured by Gibco BRL) supplemented with 0.05% of bovine serum albumin (manufactured by Sigma Co.).

The buffers may be sterilized by filtration through a membrane filter with a 0.45 μm pore size and stored at 4° C., or may be prepared at use.

(2) SLC-1 Preparation

SLC-1-expressed CHO cells are subcultured at $5\times10^5$ cells/well on a 12-well plate followed by culturing at 37° C. under a 5% $CO_2$ and 95% air for 2 days.

(3) Labeled Ligand

MCH labeled with [3H], [$^{125}$I], [$^{14}$C], [$^{35}$S], etc. A solution of the labeled ligand in an appropriate solvent or buffer is stored at 4° C. or at −20° C. and diluted with a buffer for assay to a concentration of 1 μM.

(4) Standard Ligand Solution

MCH is dissolved in PBS containing 0.1% bovine serum albumin (manufactured by Sigma) to yield a concentration of 1 mM, and the solution is stored at −20° C.

2. Method for Assay (1) The SLC-1-expressed cells cultivated on the 2-well culture plate are washed twice with 1 ml of the assay buffer, followed by addition of 490 μl of the assay buffer to each well.

(2) After addition of 5 μl of a $10^{-3}$ to $10^{-10}$ M solution of a test compound, 5 μl of the labeled MCH is added followed by reacting at room temperature for an hour. To determine the amount of the non-specific binding, 5 μl of the ligand (MCH) of $10^{-3}$ M is added in place of the test compound.

(3) The reaction mixture is removed and the cells are washed three times with 1 ml each of the buffer for washing. The labeled ligand (MCH) bound to the cells is dissolved in 0.2N NaOH-1% SDS, and the solution is mixed with 4 ml of a liquid scintillator A (manufactured by Wako Pure Chemical Industries).

(4) The radioactivity is measured by use of a scintillation counter (manufactured by Beckman). The percent of the maximum binding (PMB) is calculated from the following equation [Equation 1].

$$PMB=[(B-NSB)/(B_0-NSB)]\times 100 \qquad \text{[Equation 1]}$$

wherein:

PMB: Percent of the maximum binding

B: Radioactivity when a sample fluid is added

NSB: Non-specific binding $B_0$: Maximum binding

The compound or its salt obtainable by the screening method or by the screening kit of the present invention is the compound that alters (inhibits or promotes) the binding between MCH or its salt and SLC-1 or its salt, specifically a compound or its salts having an SLC-1-mediated cell-stimulating activity (so-called SLC-1 agonists) or a compound having no cell-stimulating activity (so-called SLC-1 antagonists). Examples of the compound include a peptide, a protein, a non-peptide compound, a synthetic compound, a fermentation product, etc. and the compound may be either novel or known compound.

To determine if the compound is SLC-1 agonists or antagonists, the following specific procedure (i) or (ii) is available.

(i) The binding assay described in the screening method of (1) through (3) supra is performed to obtain the compound that alters the binding property between MCH or its salts and SLC-1 or its salts (especially inhibits the binding) followed by assay for the compound to determine if the compound has the SLC-1-mediated cell stimulating activities described above. The compound having the cell stimulating activities or its salts are SLC-1 agonists, whereas the compound having no such activity or its salts are SLC-1 agonists.

(ii) (a) A test compound is brought into contact with SLC-1-containing cells to assay the SLC-1-mediated cell stimulating activities. The compound having the cell stimulating activities or its salts are SLC-1 agonists.

(b) The SLC-1-mediated cell stimulating activities are assayed both when a compound (e.g., the polypeptide of the present invention or an SLC-1 agonist, etc.) that activates the SLC-1 is brought into contact with the SLC-1-containing cells and when the compound that activates SLC-1 and a test compound are brought into contact with the SLC-1-containing cells and comparison is made on the cell stimulating activities between the two cases. The compound or its salts that can reduce the cell stimulating activities by the SLC-1-activating compound are SLC-1 antagonists.

The SLC-1 agonists exhibit activities similar to the physiological activities that MCH or its salts possess and are thus useful as safe and low toxic drugs as in the MCH or its salts.

To the contrary, since the S SLC-1 antagonists can suppress the physiological activities possessed by MCH or its salts, they are useful as safe and low toxic drugs for suppressing the receptor activity.

Since MCH or its salts take part in an appetite (eating) promoting activity, an oxytocin secretion promoting activity, etc., the MCH or its salts can be used as an appetite (eating) promoting agent, an oxytocin secretion promoting agent, etc. Therefore, in the compounds obtainable using the screening method or screening kit described above, the SLC-1 agonists are available not only as an appetite (eating) promoting agent but also as a prophylactic/therapeutic agent for weak pains, atonic bleeding, before and after expulsin, subinvolution of uterus, cesarean section, induced abortion, galactostasis, anorexia such as anorexia nervosa and anemia accompanied thereby, hypoproteinosis, etc., and the SLC-1 agonists are available not only as an antiobestic agent (drug), an appetite (eating) modulator, etc. but also as a prophylactic/therapeutic agent for hyperstimulation, ankylosing uterine contractions, fetal distress, uterine rupture, cervical laceration, preterm delivery, Prader-Willi syndrome, diabetes mellitus and its complications (diabetic nephropathy, diabetic retinopathy, diabetic neuropathy, etc.), hypertension, hyperlipemia, coronary sclerosis, gout, respiratory disease (Pickwick syndrome, sleep apnea), fatty liver, sterility, osteoarthritis deformans, etc. (especially an antiobestic agent, an appetite (eating) modulator, etc.).

Specific examples of the compounds obtained using the screening method or the screening kit of the present invention include compounds (1) through (42) below, which are described in, e.g., Japanese Patent Unexamined Publication (Laid-open) No. 11-35788.

(1)
N-[2-(N,N-Dimethylamino)methyl-6-tetralinyl]-(4'-methoxybiphenyl-4-yl)carboxamide

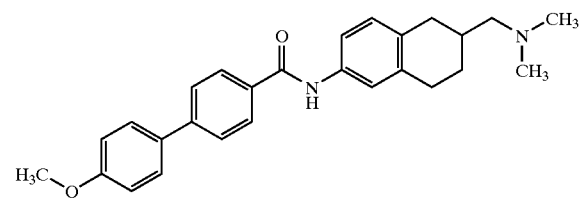

(2)
4-Benzoyl-N-(2-(N,N-dimethylamino)methyl-6-tetralinyl]benzamide

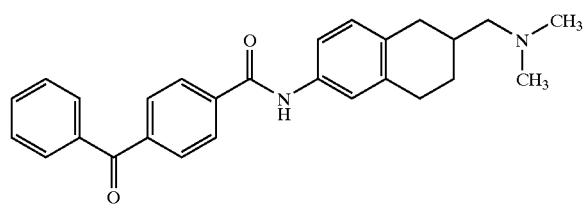

(3)
N-[2-(N,N-Dimethylamino)methyl-6-tetralinyl]-4-(1,3-dioxo-1,3-dihydro-2H-isoindol-2-yl)benzamide

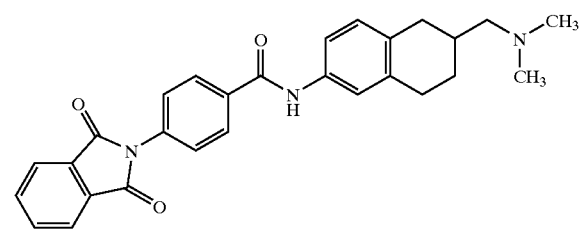

(4)
4-(Benzoylamino)-N-[2-(N,N-dimethylamino)methyl-6-tetra linyl]benzamide

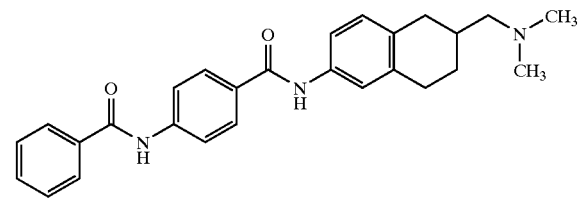

(5)
4-(Benzyloxy)-N-[2-(N,N-dimethylamino)methyl-6-tetralinyl]benzamide

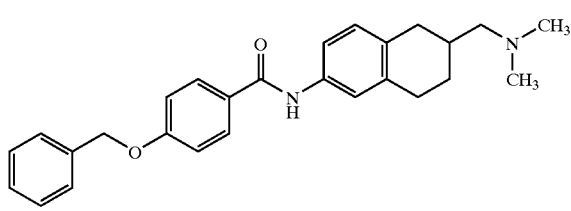

(6)
N-[2-(N,N-Dimethylamino) methyl-6-tetralinyl]-9-oxo-9H-fluorene-2-carboxamide

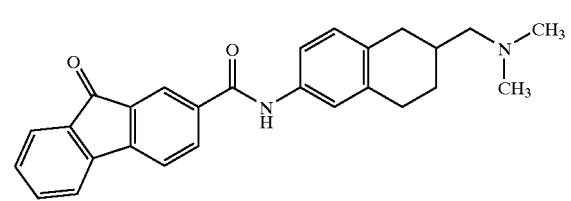

(7)
N-[2-(N,N-Dimethylamino)methyl-6-tetralinyl]-9,10, 10-trioxo-9,10-dihydro-10$1^6$-thioxanthene-3-carboxamide

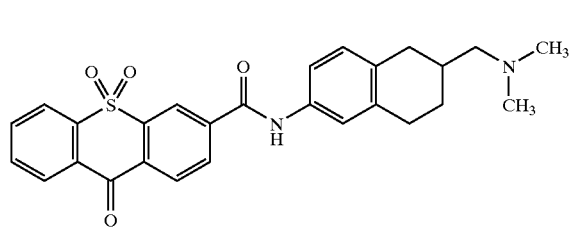

(8)
(4-Anilinocarbonyl)amino-N-[2-(N,N-dimethylamino) methyl -0.6-tetralinyl]benzamide

(9)
N-[2-(N,N-Dimethylamino)methyl-6-tetralinyl]-4-phenoxybenzamide

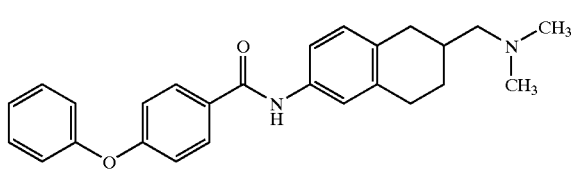

(10)
N$^1$-[2-(N,N-Dimethylamino)methyl-6-tetralinyl]-N$^4$-phenyl terepthalamide

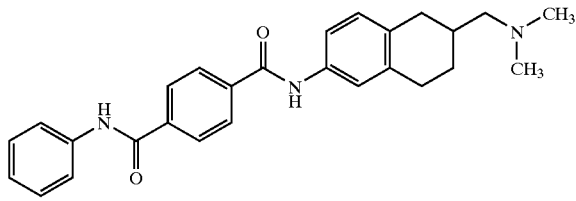

(11)
(4'-Ethylbiphenyl-4-yl)-N-[2-(N,N-dimethylamino)methyl-6-tetralinyl]carboxamide

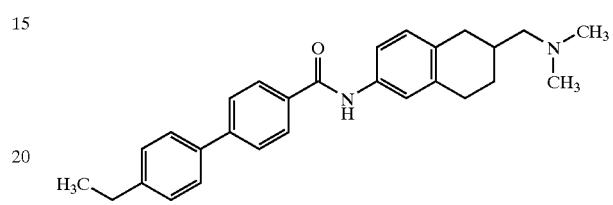

(12)
(4'-Chlorobiphenyl-4-yl)-N-[2-(N,N-dimethylamino)methyl-6-tetralinyl]carboxamide

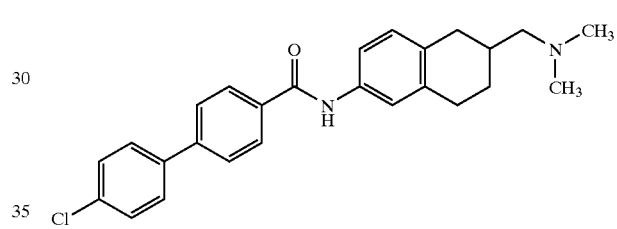

(13)
(4'-Acetylaminobiphenyl-4-yl)-N-[2-(N,N-dimethylamino)methyl-6-tetralinyl]carboxamide

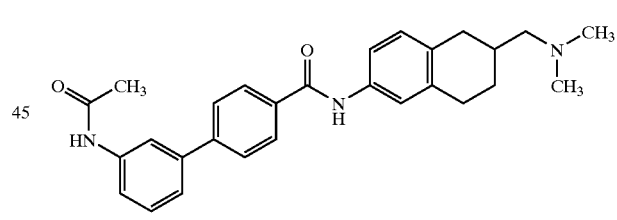

(14)
4-(1,3-Benzodioxol-5-yl)-N-[2-(N,N-dimethylamino) methyl -6-tetralinyl]benzamide

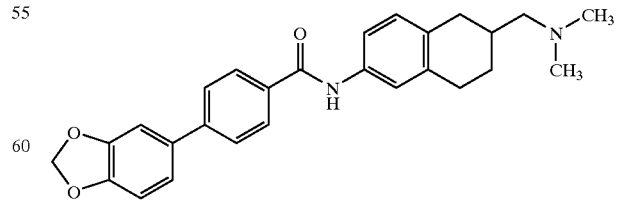

(15)
4-Bromo-N-[6-[(N,N-dimethylamino)methyl]-5,6,7,8-tetrahydro-2-naphthalenyl]benzamide

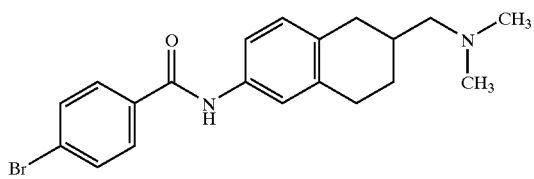

(16)
3',4'-Dichloro-N-[6-[(N,N-dimethylamino)methyl]-5,6,7,8-tetrahydro-2-naphthalenyl][1,1'-biphenyl]-4-carboxamid

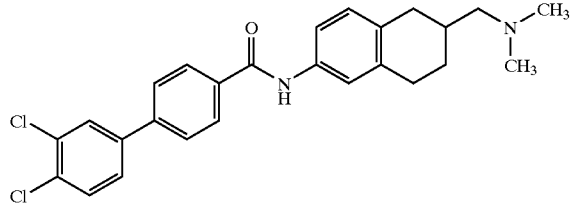

(17)
N-[6-[(N,N-Dimethylamino)methyl]-5,6,7,8-tetrahydro-2-naphthalenyl]-4'-phenyl[1,1'-biphenyl]-4-carboxamide hydrochloride

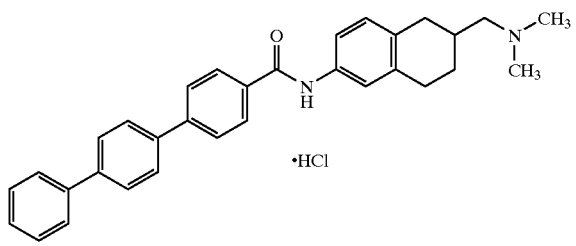

(18)
N-[6-[(N,N-Dimethylamino)methyl]-5,6,7,8-tetrahydro-2-naphthalenyl]-2'-methoxy[1,1'-biphenyl]-4-carboxamide

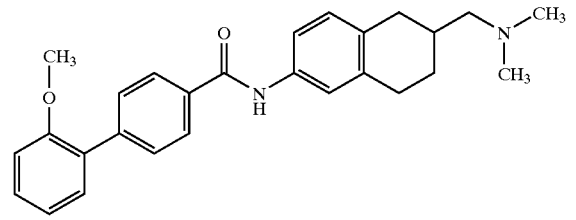

(19)
N-[6-[(N,N-Dimethylamino)methyl]-5,6,7,8-tetrahydro-2-naphthalenyl]-4'-oxy[1,1'-biphenyl]-4-carboxamide sodium salt

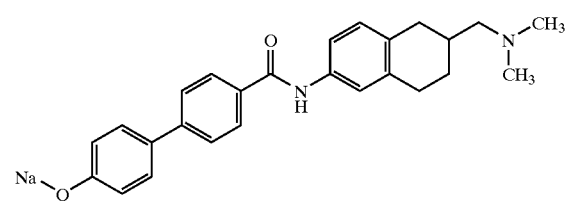

(20)
N-[6-[(N,N-Dimethylamino)methyl]-5,6,7,8-tetrahydro-2-naphthalenyl]-4'-formyl[1,1'-biphenyl]-4-carboxamide

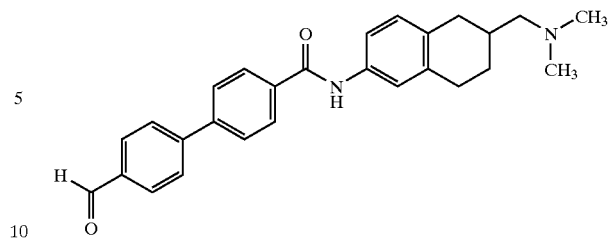

(21)
N-[6-[(N,N-Dimethylamino)methyl]-5,6,7,8-tetrahydro-2-naphthalenyl]-4'-(hydroxymethyl)[1,1'-biphenyl]-4-carboxamide

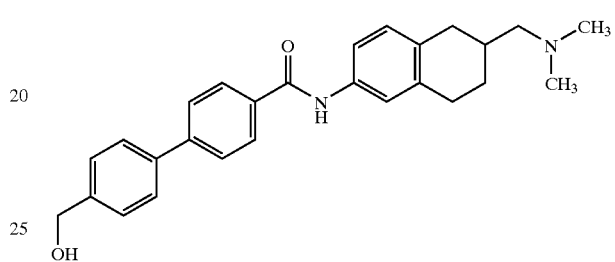

(22)
N-[6-[(N,N-Dimethylamino)methyl]-5,6,7,8-tetrahydro-2-naphthalenyl]-4'-propyl[1,1'-biphenyl]-4-carboxamide

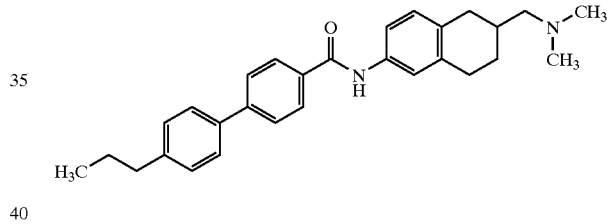

(23)
4-Bromo-2-chloro-N-[6-[(N,N-dimethylamino)methyl]-5,6,7,8-tetrahydro-2-naphthalenyl]benzamide

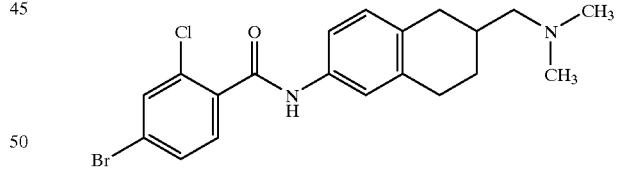

(24)
4-Bromo-N-[6-[(N,N-dimethylamino)methyl]-5,6,7,8-tetrah ydro-2-naphthalenyl]-2-methylbenzamide

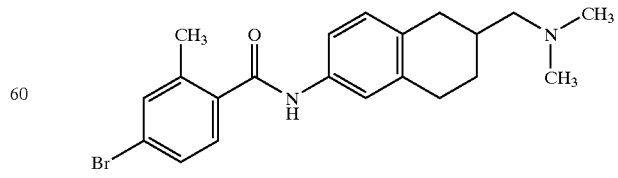

(25)
4-Bromo-N-[6-[(N,N-dimethylamino)methyl]-5,6,7,8-tetrah ydro-2-naphthalenyl]-3-methylbenzamide

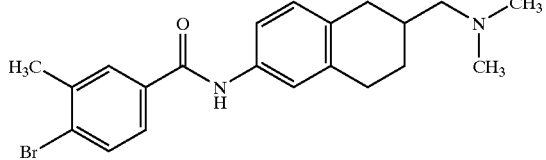

(26) 3,4'-Dichloro-N-[6-[(N,N-dimethylamino)methyl]-5,6,7,8-tetrahydro-2-naphthalenyl][1,1'-biphenyl]-4-carboxamide

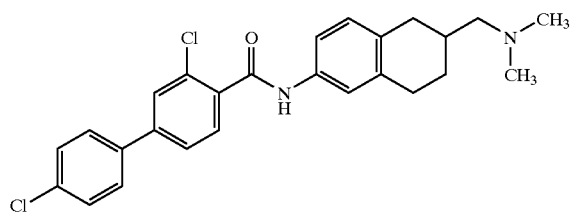

(27) 4'-Chloro-N-[6-[(N,N-dimethylamino)methyl]-5,6,7,8-tetrahydro-2-naphthalenyl]-3-methyl[1,1'-biphenyl]-4-carbox amide

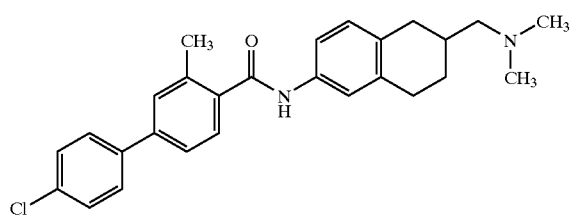

(28) 4'-Chloro-N-[6-[(N,N-dimethylamino)methyl]-5,6,7,8-tetrahydro-2-naphthalenyl]-2-methyl[1,1'-biphenyl]-4-carbox amide

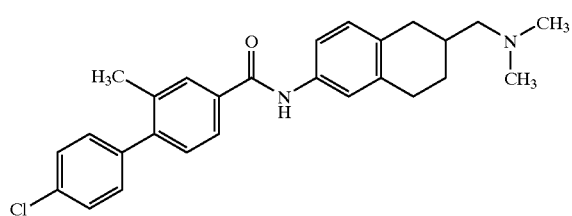

(29) N-[6-[(N,N-Dimethylamino)methyl]-5,6,7,8-tetrahydro-2-naphthalenyl]-4'-(trifluoromethyl)[1,1'-biphenyl]-4-carboxamide

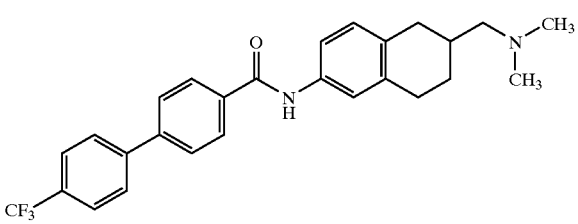

(30) N-[6-[(N,N-Dimethylamino)methyl]-5,6,7,8-tetrahydro-2-naphthalenyl]-4-(3-pyridinyl)benzamide

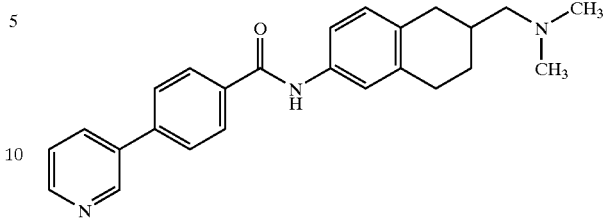

(31) N-[6-[(N,N-Dimethylamino)methyl]-5,6,7,8-tetrahydro-2-naphthalenyl]-4'-[(trifluoroacetyl)amino][1,1'-biphenyl]-4-carboxamide

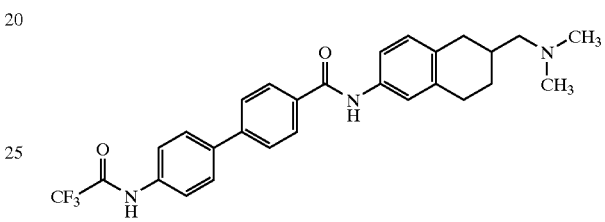

(32) N-[6-[(N,N-Dimethylamino)methyl]-5,6,7,8-tetrahydro-2-naphthalenyl]-4'-(4,4-dimethyl-4,5-dihydro-1,3-oxazol-2-yl)[1,1'-biphenyl]-4-carboxamide

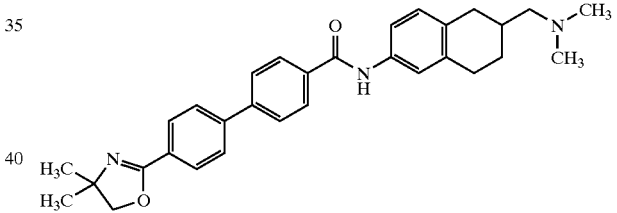

(33) 4'-Amino-N-[6-[(N,N-dimethylamino)methyl]-5,6,7,8-tetrahydro-2-naphthalenyl][1,1'-biphenyl]-4-carboxamide

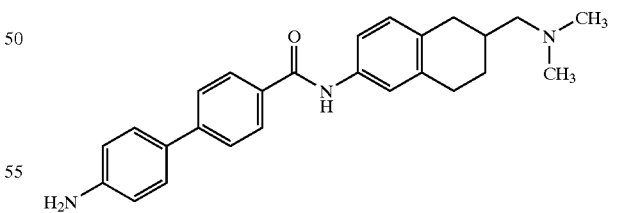

(34) N-[6-[(N,N-Dimethylamino)methyl]-5,6,7,8-tetrahydro-2-naphthalenyl]-4-(2-thienyl)benzamide

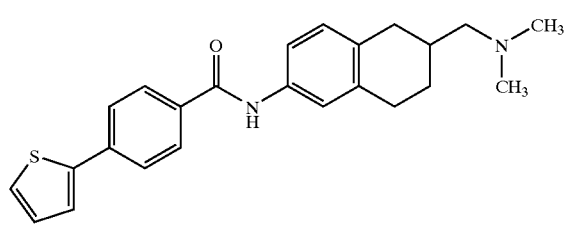

(35) Ethyl 4'-[[[6-[(N,N-dimethylamino)methyl]-5,6,7,8-tetrahydro-2-naphthalenyl]amino]carbonyl][1,1'-biphenyl]-4-carboxylate

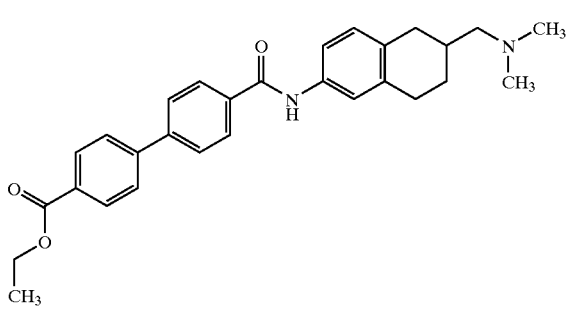

(36) N-[6-[(N,N-Dimethylamino)methyl]-5,6,7,8-tetrahydro-2-naphthalenyl]-4'-(methylsulfanil)[1,1'-biphenyl]-4-carboxamide

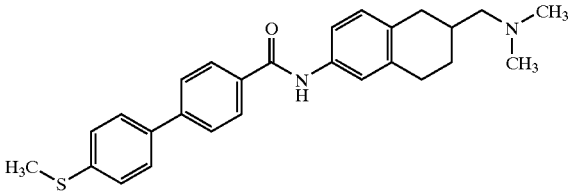

(37) 4'-(N,N-Dimethylamino)-N-[6-[(N,N-dimethylamino)methyl]-5,6,7,8-tetrahydro-2-naphthalenyl][1,1'-biphenyl]-4-carboxamide

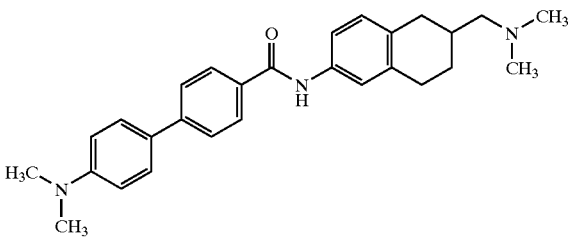

(38) N-[6-[(N,N-Dimethylamino)methyl]-5,6,7,8-tetrahydro-2-naphthalenyl]-4'-(methylamino)[1,1'-biphenyl]-4-carboxamide

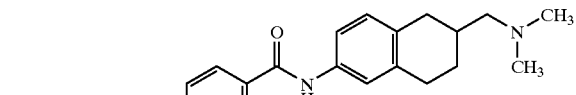

(39) N-[6-[N,N-Dimethylamino)methyl]-5,6,7,8-tetrahydro-2-naphthalenyl]-4-(2-furyl)benzamide

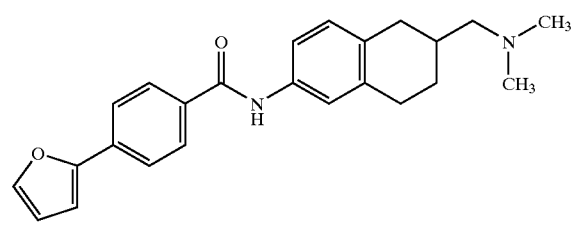

(40) 4'-[[[6-[(N,N-Dimethylamino)methyl]-5,6,7,8-tetrahydro-2-naphthalenyl]amino]carbonyl][1,1'-biphenyl]-4-carboxylic acid

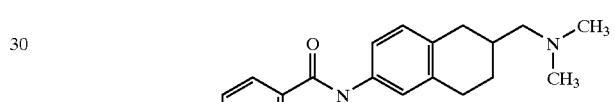

to (41) 4'-Chloro-N-[6-[(N,N-dimethylamino)methyl]-7,8-dihydro-2-naphthalenyl][1,1'-biphenyl]-4-carboxamide

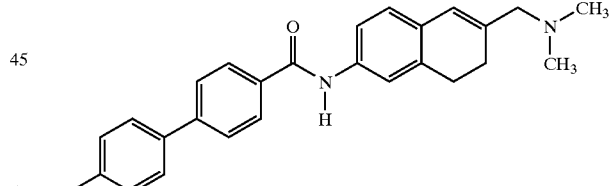

(42) 4'-Fluoro-N-[6-[(N,N-dimethylamino)methyl]-7,8-dihydro-2-naphthalenyl][1,1'-biphenyl]-4-carboxamide

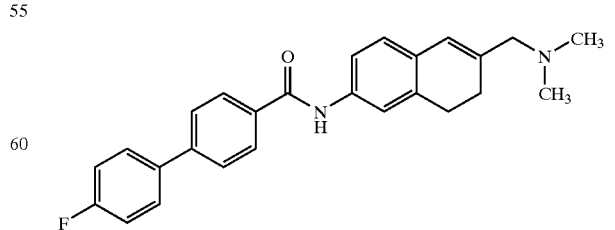

The agonist activity of the above-described compound (1) (N-[2-(N,N-dimethylamino)methyl-6-tetralinyl]-(4'-metho xybiphenyl-4-yl)carboxamide) was measured by the method given in EXAMPLE 21 later described, and the binding inhibition rate (%) was calculated by the equation: (radioactivity when the compound and MCH were added—radioactivity when DMSO solution was added)/ (radioactivity when MCH was added—radioactivity when DMSO solution was added)×100, whereby $IC_{50}$(nM) of the compound was calculated from the binding inhibition rate (%). The $IC_{50}$(nM) of the compound (1) supra (N-[2-(N,N-dimethylamino)methyl-6-tetralinyl]-(4'-methoxybiphenyl-4-yl)carboxamide) was found to be 40. It was thus established that the compound (1) was the compound (antagonist) obtained using the screening method or the screening kit described above.

As the salts of the compounds that are obtainable by the screening method or the screening kit described above, pharmaceutically acceptable salts are employed. Examples of such salts include salts with inorganic bases, salts with organic bases, salts within organic acids, salts with organic acids and salts with basic or acidic amino acids, etc.

Preferred examples of the salts with inorganic bases include alkali metal salts such as sodium salts, potassium salts, etc.; alkaline earth metal salts such as calcium salts, magnesium salts, etc.; aluminum salts, ammonium salts, and the like.

Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc.

Preferred examples of the salts with inorganic acids include salts with hydrochloric acid, hydrobromic acid, sulfuric acid, phosphoric acid, etc.

Preferred examples of the salts with organic acids include salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid, etc.

Preferred examples of the salts with basic amino acids include salts with arginine, lysine, ornithine; etc. Preferred examples of the salts with acidic amino acids include salts with aspartic acid, glutamic acid, etc.

Where the compound or its salts obtainable by the screening methods or kits of the present invention are used as the pharmaceutical compositions described above, they can be formulated as in the case where the aforesaid polypeptide of the present invention are employed.

When the compound or its salts which are obtained by the screening methods or screening kits of the present invention are used as the above-mentioned pharmaceutical compositions, they can be formulated in a conventional manner. For example, they can be administered orally as tablets coated with sugar or with enteric coating if necessary, capsules, elixirs, microcapsules, etc., or parenterally in the form of injections such as sterile solutions or suspensions in water or in pharmaceutically acceptable solutions other than water. For example, the compound or its salts can be mixed with carriers, flavoring agents, excipients, vehicles, preservatives, stabilizers, binders, etc. in a unit dosage form required for generally accepted pharmaceutical practice to prepare pharmaceutical preparations. The amount of active ingredients in these preparations is adjusted so as to obtain appropriate doses within specified ranges.

Additives miscible with tablets, capsules, etc. include a binder such as gelatin, corn starch, tragacanth and gum arabic, an excipient such as crystalline cellulose, a, swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of a capsule, liquid carriers such as oils and fats may further be used together with the additives described above. A sterile composition for injection may be formulated in a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol), a poly alcohol (e.g., propylene glycol and polyethyleneglycol), a nonionic surfactant (e.g., polysorbate 80(™) and HCO-50), etc. Examples of the oily medium include sesame oil and soybean oil, which may also be used in combination with a dissolution aid such as benzyl benzoate and benzyl alcohol.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the pharmaceutical preparation thus obtained is safe and low toxic, it can be administered to human or another mammal (e.g., mouse, rat, guinea pig, rabbit, sheep, swine, bovine, cat, dog, monkey, chimpanzee, etc.).

The dose of the compound or its salts which are obtainable using the screening method or screening kit of the present invention varies depending on conditions, etc.; for example, in oral administration of the compounds, the dose is normally about 0.1 to about 1000 mg, preferably about 1.0 to about 300 mg, more preferably about 3.0 to about 50 mg per day for adult (as 60 kg body weight). In parenteral administration, the single dose varies depending on subject to be administered, target organ, conditions, method for administration, etc.; in the form of an injection, it is advantageous to administer, for example, the SLC-1 antagonist intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

In the specification and drawings, when bases, amino acids, etc. are represented by abbreviations, the codes for bases and amino acids are denoted in accordance with the IUPAC-IUB Commission on Biochemical Nomenclature or by the codes conventionally used in the art, examples of which are shown below. With respect to amino acids that may have their optical isomers, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |

-continued

| | |
|---|---|
| C | cytosine |
| Y | thymine or cytosine |
| N | thymine, cytosine, adenine or guanine |
| R | adenine or guanine |
| M | cytosine or adenine |
| W | thymine or adenine |
| S | cytosine or guanine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| TFA | trifluoroacetic acid |
| EIA | enzyme immunoassay |
| Gly or G | glycine |
| Ala or A | alanine |
| Val or V | valine |
| Leu or L | leucine |
| Ile or I | isoleucine |
| Ser or S | serine |
| Thr or T | threonine |
| Cys or C | cysteine |
| Met or M | methionine |
| Glu or E | glutamic acid |
| Asp or D | aspartic acid |
| Lys or K | lysine |
| Arg or R | arginine |
| His or H | histidine |
| Phe or F | phenylalanine |
| Tyr or Y | tyrosine |
| Trp or W | tryptophan |
| Pro or P | proline |
| Asn or N | asparagine |
| Gln of Q | glutamine |
| pGlu | pyroglutamic acid |
| Me | methyl group |
| Et | ethyl group |
| Bu | butyl group |
| Ph | phenyl group |
| Tc | thiazolidine-4(R)-carboxamide group |
| Bom | benzyloxymethyl |
| NMP | N-methylpyrrolidone |
| PAM | phenylacetamidomethyl |

The substituents, protecting groups and reagents which are frequently used in the present specification are represented by the following symbols.

| | |
|---|---|
| Tos | p-toluenesulfonyl |
| HONB | N-hydroxy-5-norbornene-2,3-dicarboximide |
| Bzl | benzyl |
| Z | benzyloxycarbonyl |
| Br-Z | 2-bromobenzyloxycarbonyl |
| Cl-Z | 2-chlorobenzyloxycarbonyl |
| Boc | t-butoxycarbonyl |
| HOBt | 1-hydroxybenztriazole |
| DCC | N,N'-dichlorohexylcarbodiimide |
| TFA | trifluoroacetic acid |
| Fmoc | N-9-fluorenylmethoxycarbonyl |
| DNP | dinitrophenol |
| Bum | t-butoxymethyl |
| Trt | trityl |
| BSA | bovine serum albumin |
| CHAPS | 3-[(3-cholamidopropyl)dimethylammonio]-1-propanesulfonate |
| PMSF | phenylmethylsulfonyl fluoride |
| E64 | (L-3-trans-carboxirane-2-carbonyl) L-leucyl-agmatine |
| GDP | guanosine-5'-diphosphate |
| MEMα | minimum essential medium alpha |
| Fura-2AM | pentacetoxymethyl 1-[6-amino-2-(5-carboxy-2-oxazolyl)-5-benzofur anyloxy]-2-(2-amino-5-methylphenoxy)ethane-N,N,N',N'-tetraacetate |
| HBSS | Hanks' balanced salt solution |
| Fluo-3AM | pentacetoxymethyl 1-[2-amino-5-(2,7-dichloro-6-hydroxy-3-oxy-9-xanthenyl)phenoxy]-2-(2-amino-5-methylphenoxy) ethane-N,N,N',N'-tetraacetate |
| HEPES | 2-[4-(2-hydroxyethyl)-1-piperazinyl]-ethanesulfonic acid |
| MeBzl | 4-methylbenzyl |
| NMP | N-methylpyrrolidone |

The sequence identification numbers in the sequence listing of the specification indicate the following sequences.

[SEQ ID NO: 1]
This represents an amino acid sequence obtained from N-terminal amino acid sequence analysis of a ligand peptide to the SLC-1 purified from rat brain.

[SEQ ID NO: 2]
This represents an amino acid sequence of a ligand peptide to the SLC-1 purified from rat brain, which is identified to be rat MCH.

[SEQ ID NO: 3]
This represents a synthetic DNA used to screen cDNA encoding rat SLC-1.

[SEQ ID NO: 4]
This represents a synthetic DNA used to screen cDNA encoding rat SLC-1.

[SEQ ID NO: 5]
This represents the full-length amino acid sequence of rat SLC-1.

[SEQ ID NO: 6]
This represents the full-length base sequence of rat SLC-1 cDNA in which Sal I recognition sequence is added at the 5' side and Spe I recognition sequence at the 3' side.

[SEQ ID NO: 7]
This represents a riboprobe used to measure the amount of SLC-1 mRNA expressed in each clone of rat SLC-1-expressed CHO cells.

[SEQ ID NO: 8]
This represents a synthetic DNA used to acquire cDNA encoding human SLC-1

[SEQ ID NO: 9]
This represents a primer used to convert cDNA encoding human SLC-1 into double strands.

[SEQ ID NO: 10]
This represents the full-length base sequence of cDNA encoding human SLC-1.

[SEQ ID NO: 11]
This represents the full-length amino acid sequence of human SLC-1.

[SEQ ID NO: 12]
This represents a synthetic DNA used to screen cDNA encoding human SLC-1(S).

[SEQ ID NO: 13]
This represents a synthetic DNA used to screen cDNA encoding human SLC-1(S).

[SEQ ID NO: 14]
This represents a synthetic DNA used to screen cDNA encoding human SLC-1(L).

[SEQ ID NO: 15]
This represents a synthetic DNA used to screen cDNA encoding human SLC-1(L).

[SEQ ID NO: 16]
This represents the full-length base sequence of human SLC-1(S) cDNA in which Sal I recognition sequence is added at the 5' side and Spe I recognition sequence at the 3' side.

[SEQ ID NO: 17]

This represents the full-length base sequence of human SLC-1(L) cDNA in which Sal I recognition sequence is added at the 5' side and Spe I recognition sequence at the 3' side.

[SEQ ID NO: 18]

This represents a riboprobe used to measure the amount of SLC-1 mRNA expressed in each clone of human SLC-1(S)-expressed CHO cells and human SLC-1(L)-expressed CHO cells.

[SEQ ID NO: 19]

This represents an amino acid sequence of Des-Asp$^1$-MCH (MCH(2-19))

[SEQ ID NO: 20]

This represents an amino acid sequence of Des-[Asp$^1$, Phe$^2$]-MCH (MCH(3-19)).

[SEQ ID NO: 21]

This represents an amino acid sequence of Des-[Asp$^1$, Phe$^2$, Asp$^3$-MCH (MCH(4-19)).

[SEQ ID NO: 22]

This represents an amino acid sequence of Des-[Asp$^1$, Phe$^2$, Asp$^3$, Met$^4$]-MCH (MCH(5-19)).

[SEQ ID NO: 23]

This represents an amino acid sequence of Des-[Asp$^1$, Phe$^2$, Asp$^3$, Met, Leu$^5$]-MCH (MCH(6-19)).

[SEQ ID NO: 24]

This represents an amino acid sequence of Des-[Asp$^1$, Phe$^2$, Asp$^3$, Met$^4$, Leu$^5$, Arg$^6$]-MCH (MCH(7-19)).

Transformant *Escherichia coli* DH10B/phSLC1L8 transformed with plasmid containing a DNA coding for the base sequence shown by SEQ ID NO:11, which was obtained in EXAMPLE 8, was on deposit with the Ministry of International Trade and Industry, Agency of Industrial Science and Technology, National Institute of Bioscience and Human Technology (NIBH) as Accession Number FERM BP-6632 on Feb. 1, 1999 and with Institute for Fermentation, Osaka (IFO) as Accession Number IFO 16254 on Jan. 21, 1999.

EXAMPLES

The present invention is described below in more detail with reference to EXAMPLES and REFERENCE EXAMPLES, but not intended to limit the scope of the present invention thereto.

Reference Example 1

Detection of the activity contained in rat brain extract and specifically inhibiting CAMP synthesis of CHO/SLC-1 cells.

Fractions of the rat brain extract by high performance liquid chromatography (HPLC) were prepared by the method described below. Brains were withdrawn from 100 Wistar rats (male, 8 weeks old) purchased from Charles River Co. and immediately put into 0.8 liter of boiling distilled water followed by boiling for 10 minutes. Immediately after the boiling, the brains were ice-cooled and 48 ml of acetic acid was added thereto to a final concentration of 1.0 M. Using a polytron (20,000 rpm, 6 mins.), the cells were disrupted. The cell disruption fluid was centrifuged (8,000 rpm, 30 mins.). The supernatant was taken out and to the precipitate, 0.8 liter of 1.0 M acetic acid was added. The cells were again disrupted by the polytron followed by centrifugation (8,000 rpm, 30 mins.). The supernatant was thus obtained. After 0.8 liter of 1.0 M acetic acid was added to the precipitate, the mixture was again disrupted by the polytron. After stirring overnight, centrifugation was performed (8.000 rpm, 30 mins.) to obtain the supernatant. After 2-fold volume of chilled acetone was dropwise added slowly to the supernatant at 4° C., the supernatant obtained by the first centrifugation was stirred overnight and, the supernatant obtained by the second centrifugation was stirred for 4 hours. The acetone-added extract was centrifuged (8,000 rpm, 30 mins.) to remove the precipitate. Acetone was evaporated off in vacuum from the supernatant obtained, using an evaporator. After an equal volume of diethyl ether was added to the acetone-free extract, the ethereal layer containing lipids was separated using a separating funnel to recover the aqueous layer. The lipids were removed with ether and the extract was concentrated in vacuum using an evaporator to completely remove the ether. The concentrate was filtrated through a glass fiber filter paper (Advantech, DP70 (90 mmφ)) and the filtrate was charged in a glass-made column (20 mmφ×240 mm) packed with C18 (YMC, YMCgel ODS-AM120-S50). After washing with 300 ml of 1.0 M acetic acid, the column was eluted with 300 ml of 60% acetonitrile containing 0.1% trifluoroacetic acid. The eluate was concentrated in vacuum to distill the solvent off. The concentrate was then lyophilized. About 0.24 g of the lyophilized product was dissolved in 5 ml of DMSO and then, 45 ml of 1.0 M acetic acid was added to the solution to prepare the rat brain extract preparation. The rat brain extract preparation was passed through an SP-Sephadex C-25 column (Amersham Pharmacia Biotech, gel volume: 100 ml) which had been equilibrated with 1.0 M acetic acid. After washing with 50 ml of 1.0 M acetic acid, a fraction eluted with 100 ml of 2.0 M pyridine and a fraction eluted with 100 ml of 2.0 M pyridine/acetic acid were obtained sequentially. The 2.0 M pyridine/acetic acid eluate was concentrated in vacuum to distill the solvent off, the concentrate was lyophilized. About 100 mg of the lyophilized product was dissolved in 10 ml of 10% acetonitrile containing 0.1% trifluoroacetic acid. The solution was applied to HPLC by acetonitrile density gradient elution of 10% to 60% acetonitrile containing 0.1% trifluoroacetic acid, using a C18 column (TOSO, TSKgel ODS-80T$_a$, (21.5 mmφ300 mm)). Each fraction was concentrated and evaporated to dryness in vacuum. The residue was dissolved in 0.2 ml of dimethylsulfoxide (DMSO).

The CHO/SLC-1 cells prepared in EXAMPLE 4 and mock CHO cells were inoculated on a 24-well plate in 5×10$^4$ cells/well. After incubation for 48 hours, the cells were washed with Hanks' balanced salt solution (pH 7.4) supplemented with 0.2 mM 3-isobutylmethylxanthine, 0.05% BSA and 20 mM HEPES (hereinafter Hanks' balanced salt solution (pH. 7.4) supplemented with 0.2 mM 3-isobutylmethylxanthine, 0.05% BSA and 20 mM HEPES is referred to as a reaction buffer). Thereafter, 0.5 ml of the reaction buffer was added to the cells, which was kept warm in the medium for 30 minutes. The reaction buffer was removed and 0.25 ml of a fresh reaction buffer was added to the cells. Then, 0.25 ml of the reaction buffer containing the HPLC fraction and 2 μM for skolin was added to the cells followed by reacting at 37° C. for 24 minutes. By adding 100 μl of 20% perchloric acid, the reaction was terminated. The reaction mixture was then allowed to stand on ice for an hour to extract intracellular cAMP. The amount of cAMP in the extract was measured using a cAMP EIA kit (Amersham Pharmacia Biotech). As a result, the cAMP synthesis inhibitory activity specific to the CHO/SLC-1 cells was detected in fractions #33, #34 and #35 (FIG. 1). In FIG. 1, taking as 100% the amount obtained by subtracting the intracellular cAMP amount when adding the reaction buffer from the intracellular cAMP amount when adding the forskolin-containing reaction buffer, the cAMP synthesis inhibitory activity was expressed by % in terms of the intracellular cAMP amount obtained by subtracting the intracellular cAMP amount when adding the reaction buffer from the intracellular cAMP amount when adding the HPLC fraction (a 1 μl aliquot of each fraction diluted to 100-fold with DMSO was added).

Reference Example 2

Inactivation with Pronase of the Active Substance Showing the cAMP Synthesis Inhibitory Activity Specific to the SLC-1-expressed CHO cells in the rat brain Extract The HPLC fraction #34 found to have the cAMP synthesis inhibitory activity on the CHO/SLC-1 cells in REFERENCE EXAMPLE 1 was treated with a pronase (Sigma, protease Type XIV (P5147)), which is a proteolytic enzyme to examine if the active substance is proteinaceous.

Figure 2:
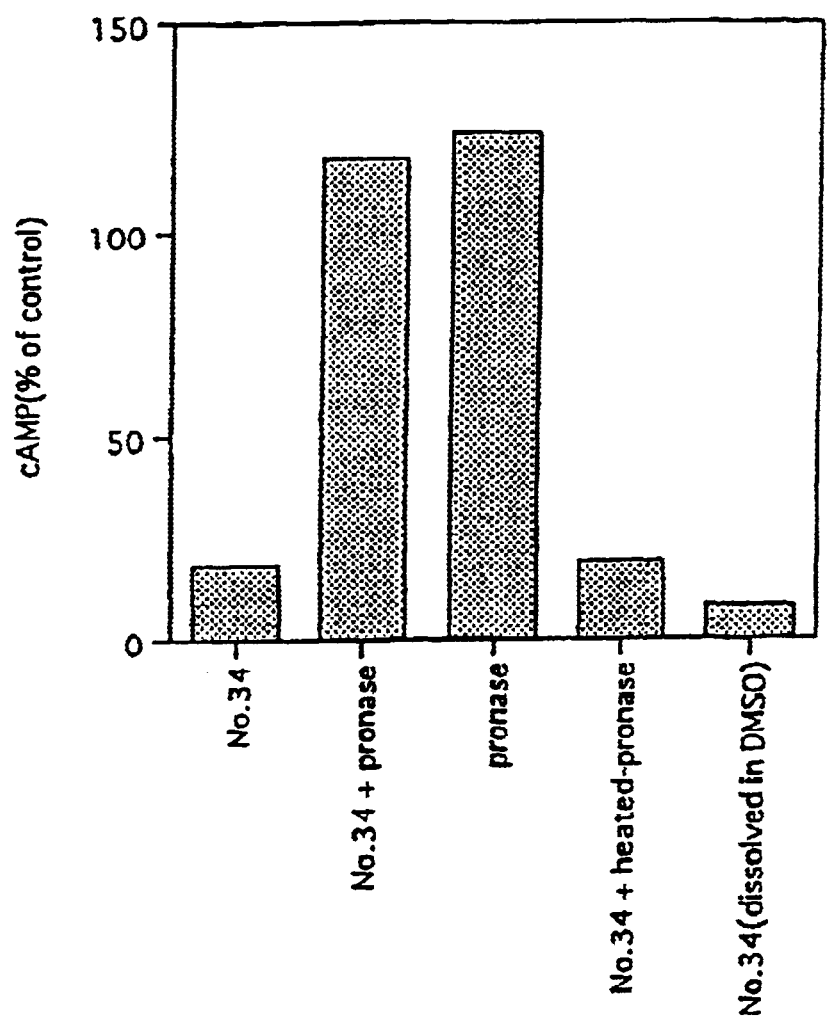
FIG. 2 shows a behavior of the rat brain-derived HPLC fraction #34 in REFERENCE EXAMPLE 1 on the cAMP synthesis inhibitory activity when treated with pronase.

The HPLC fraction (#34), 2 μl, from the rat brain extract described above was added to 100 μl of 0.2 M ammonium acetate and 3 μg of pronase was added to the mixture. After incubating at 37° C. for 2 hours, the reaction mixture was boiled in boiling water for 10 minutes to inactivate the pronase. To the reaction solution was added 2 ml of distilled water containing 0.05 mg of BSA and 0.05 mg of CHAPS, followed by lyophilization. In order to examine if pronase itself, or heating and lyophilization have any effect on the test, pronase alone, the HPLC fraction alone, and a mixture of the HPLC fraction and pronase, which pronase alone was heated, were treated and lyophilized in a similar manner. Each sample fluid thus lyophilized was dissolved in a reaction buffer containing 2 μM forskolin. Each solution was added to the CHO/SLC-1 cells by the procedures described in REFERENCE EXAMPLE 1 and the CAMP synthesis inhibitory activity was assayed. The results are shown in FIG. 2. Since the active substance showing the cAMP synthesis inhibitory activity against the CHO/SLC-1 cells in the rat brain extract were completely inactivated, the substance was found to be a protein or peptide.

Reference Example 3

Purification of the active substance showing the CAMP synthesis inhibitory activity specific to the rat SLC-1/CHO cells from rat brain.

A representative example of purifying from rat brain the active substance showing the cAMP synthesis inhibitory activity specifically to the SLC-1/CHO cells is concretely described below.

Figure 3:
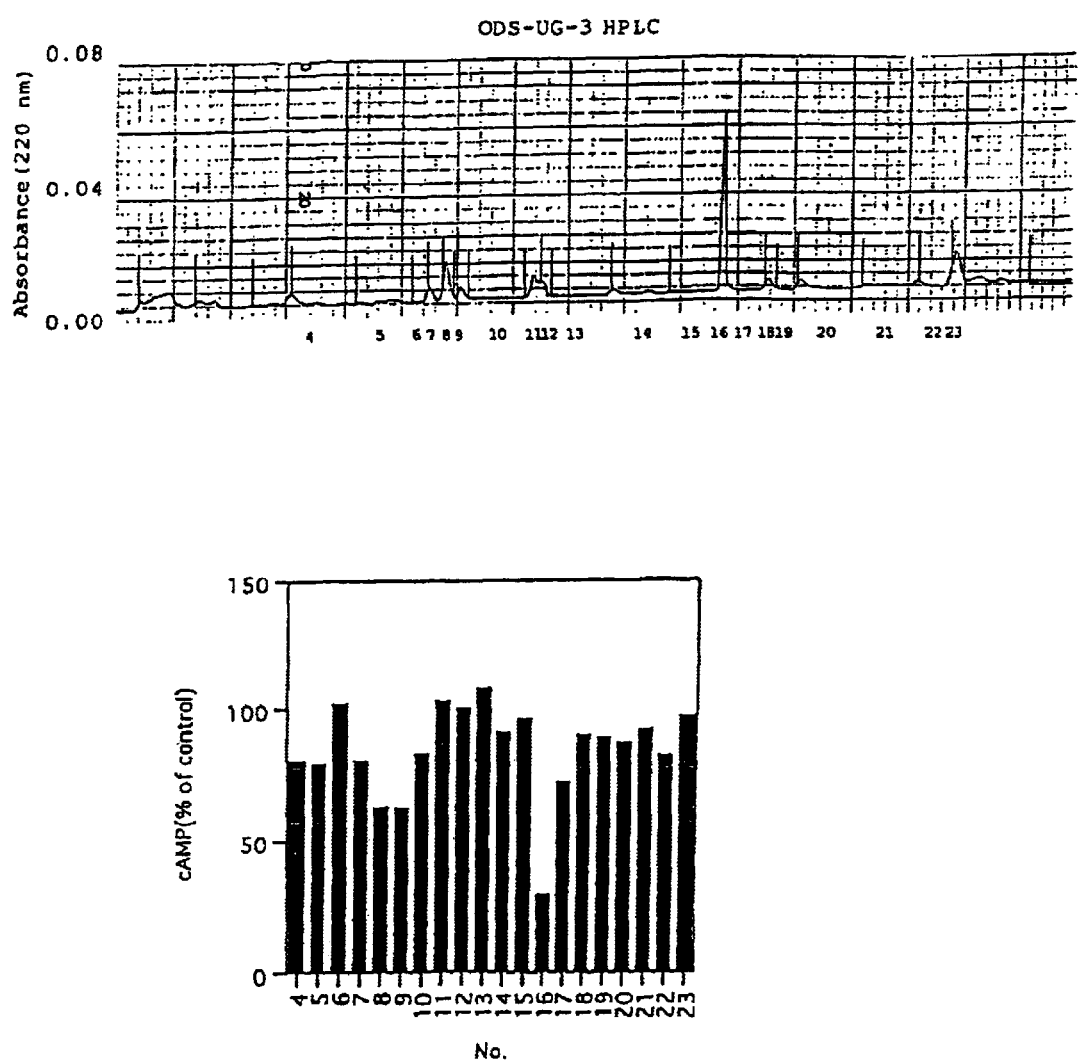
FIG. 3 shows results obtained by assaying the CHO/SLC-1 cell-specific cAMP synthesis inhibitory activity on a fraction purified through an ODS column (Develosil ODS-UG-3) in REFERENCE EXAMPLE 3.

The fraction #33 which was found to be effective in REFERENCE EXAMPLE 1 was purified as follows. After the active fraction was concentrated in vacuum to remove the solvent, the concentrate was lyophilized. The lyophilized active substance was dissolved in 5 ml of 10 mM ammonium formate (pH 5.25) containing 10% acetonitrile. The solution was passed through a cationic exchange column (TOSO, TSKgel CM-2SW (4.6 mmϕ×150 mm)). Subsequently, the column was eluted by density gradient of 10 mM to 500 mM ammonium formate (pH 5.25) containing 10% acetonitrile. The activity was recovered around 320 mM ammonium formate. To 2 ml of the active fraction was added 2.5 ml of 10% acetonitrile containing 0.1% trifluoroacetic acid. After the mixture was passed through a diphenyl column (Separation Group, Vydac 219-TP54), elution was performed by density gradient of 27.5% to 42.5% acetonitrile containing 0.1% trifluoroacetic acid. The activity appeared around 31.3% acetonitrile. After 4.4 ml of 10% acetonitrile containing 0.1% trifluoroacetic acid was added to 0.96 ml of the active fraction, the mixture was passed through an ODS column (Nomura Kagaku, Develosil ODS-UG-3), elution was performed by density gradient of 27.5% to 42.5% acetonitrile containing 0.1% trifluoroacetic acid. The eluate was manually fractionated for every peak. The activity appeared around 36.8% acetonitrile (fraction No. 16) as a single peak (FIG. 3).

Reference Example 4

Identification of the active substances to be a rat MCH, showing the cAMP synthesis inhibitory activity specifically to rat SLC-1-expressed CHO cells purified from rat brain.

The active substance showing the cAMP synthesis inhibitory activity specifically to the rat SLC-1-expressed CHO cells which was purified in REFERENCE EXAMPLE 3 was subjected to structural analysis. Since it was speculated that the active substance would be a protein or peptide as demonstrated in REFERENCE EXAMPLE 2, amino-terminal amino acid sequence analysis was conducted with LF3400 Protein Sequencer of Beckman, using the eluates containing the active peaks. As a result, the sequence shown by SEQ ID NO:1 was obtained. During the sequencing reaction, a PTH derivative of dehydro alanine produced from Cys residue was detected on the 7th and 16th residues, which was identified to be Cys. This sequence was in agreement with the amino acid sequence from the N terminus to the 16th residue of a rat melanin-concentrating hormone (MCH). When this active substance was analyzed on a mass spectrometer JEOL HX110, a signal was observed at m/z 2387.3 which was almost coincident with the molecular weight of rat MCH. Thus, the sequence of rat MCH (SEQ ID NO:2) was determined as a putative amino acid sequence of the active substance. Also, the active fractions #34 and #35 obtained in REFERENCE EXAMPLE 3 were purified to give active substances. It was confirmed that both activities were rat MCHs. Furthermore, according to the cAMP production inhibitory activity assay which was performed following the procedure later described in EXAMPLE 5, the rat MCH purchased from Peninsula Co. showed the inhibitory activity dose-dependently on the rat SLC-1-expressed cells.

Example 1

Amplification of Rat SLC-1 Receptor Cdna by Pcr using rat Brain-derived cDNA

By use of rat brain-derived poly(A)⁺RNA (Clontech Laboratories, Inc.) as a template, reverse transcription was carried out using a random primer. For the reverse transcription, reagents available from Takara RNA PCR ver. 2 kit were used. Next, using the reverse transcription product as a template, amplification by PCR was performed, using the synthetic DNA primers shown by SEQ ID NO:3 and SEQ ID NO:4. The synthetic DNA primers were constructed so as to amplify genes at the region to be translated into receptor proteins. In this case, recognition sequences of the respective restriction enzymes were added at the 5' and 3' sides so that the base sequence recognized by restriction enzyme Sal I was added at the 5' side of the gene and the base sequence recognized by restriction enzyme Spe I at the 3' side. The reaction solution was composed of 5 μl of the cDNA template, 0.4 μM each of the synthetic DNA primers, 0.25 mM dNTPs, 0.5 μl of pfu (Stratagene Co.) DNA polymerase and a buffer attached to the enzyme, which were mixed together to make the total volume 50 μl. Using a Thermal Cycler (Perkin-Elmer Co.) for amplification, heating at 94° C. for 60 seconds was followed by repeating 35 times a cycle set to include 94° C. for 60 seconds, 60 C. for 30 seconds and 72° C. for 150 seconds, and finally reacting at 72° C. for 10 minutes. The amplified product was confirmed by 0.8% agarose gel electrophoresis followed by staining with ethidium bromide.

Example 2

Subcloning of the Pcr Product into a Plasmid Vector and Confirmation of the Amplified Cdna Sequence by Decoding a Base Sequence of the Inserted Cdna Part The PCR product obtained by PCR in EXAMPLE 1 was separated by using a 0.8% low melting point agarose gel. The band part was excised from the gel with a razor blade, cut into small pieces, extracted with phenol and then with phenol/chloroform and precipitated in ethanol to recover DNAs. According to the protocol attached to PCR-Script™ Amp SK(+) Cloning Kit (Stratagene Co.), the recovered DNAs were subcloned to plasmid vector pCR-Script Amp SK(+). The recombinant vector was introduced into Escherichia coli XL-1 Blue (Stratagene Co.) to produce transformants. The clones having a cDNA-inserted fragment were selected in an LB agar medium containing ampicillin and X-gal. Only the clones exhibiting white color were picked up with a sterilized tooth pick to obtain transformant E. coli XL-1 Blue/rat SLC-1. The individual clones were cultured overnight in an LB medium containing ampicillin. Plasmid DNAs were prepared using QIA prep8 mini prep (Qiagen Co.). An aliquot of the DNAs thus prepared was cleaved by restriction enzymes Sal I and Spe I to confirm the size of the receptor cDNA fragment inserted. The reaction for base sequencing was carried out by using a Dye Deoxy Terminator Cycle Sequence Kit (Perkin-Elmer Co.), followed by decoding with a fluorescent automatic sequencer. It was confirmed by sequence analysis that the sequences of 3 clones obtained was in agreement with the gene sequence in the cDNA sequence (Lakaye, B. et al., Biochim. Biophys. Acta, Vol. 1401, pp. 216–220 (1998), accession No. AF08650) encoding rat SLC-1 protein (SEQ ID NO: 5) with the full-length sequence reported, wherein the Sal I recognition sequence was added at the 5' side and the Spe I recognition sequence was added at the 3' side (SEQ ID NO:6).

Example 3

Preparation of Rat SLC-1-Expression Cho Cells

Using Plasmid Midi Kit (Qiagen Co.), plasmid was prepared from clones of E. coli transformed by the plasmid encoding the full-length amino acid sequence of the rat brain-derived SLC-1, which sequence was confirmed in EXAMPLE 2, with the Sal I recognition sequence added at the 5' side and with the Spe I recognition sequence added at the 3' side. The plasmid was cleaved with restriction enzymes Sal I and Spe I to excise the insert part out. After electrophoresis, the inserted DNA was excised from the agarose gel with a razor blade, cut into small pieces and extracted with phenol and then with phenol/chloroform, followed by precipitation in ethanol to recover the inserted DNA. The inserted DNA was added to Sal I- and Spe I-cleaved vector plasmid pAKK01. 111H for animal cell expression (same as the vector plasmid pAKK01. 11H described in Hinuma, S. et al., Biochim. Biophys. Acta, Vol. 1219, pp. 251–259 (1994)) followed by ligation using T4 ligase (Takara Shuzo Co.). Thus, plasmid pAKK0-SLC-1 for protein expression was constructed.

After E. coli DH5 (Toyobo Co.) transformed by pAKK0-SLC-1 was cultured, plasmid DNA of pAKK0-SLC-1 was prepared using Plasmid Midi Kit (Qiagen Co.). Using Cell Phect Transfection Kit-(Amersham Pharmacia Biotech Co.), the plasmid DNA was introduced into CHO dhfr cells, according to the protocol attached to the Kit. DNA, 10 µg, was co-precipitated with calcium phosphate in suspension. The suspension was added to a 10 cm Petri dish on which $5 \times 10^5$ or $1 \times 10^6$ CHO dhfr cells had been inoculated before 24 hours. The cells were cultured in MEMα medium containing 10% calf fetal serum for one day. After passage, the cells were cultured in nucleic acid-free MEMα medium for selection containing 10% dialyzed calf fetal serum and 56 clones of the transformant SLC-1-expression CHO cells were selected as those growing in the selection medium.

Example 4

Figure 4:
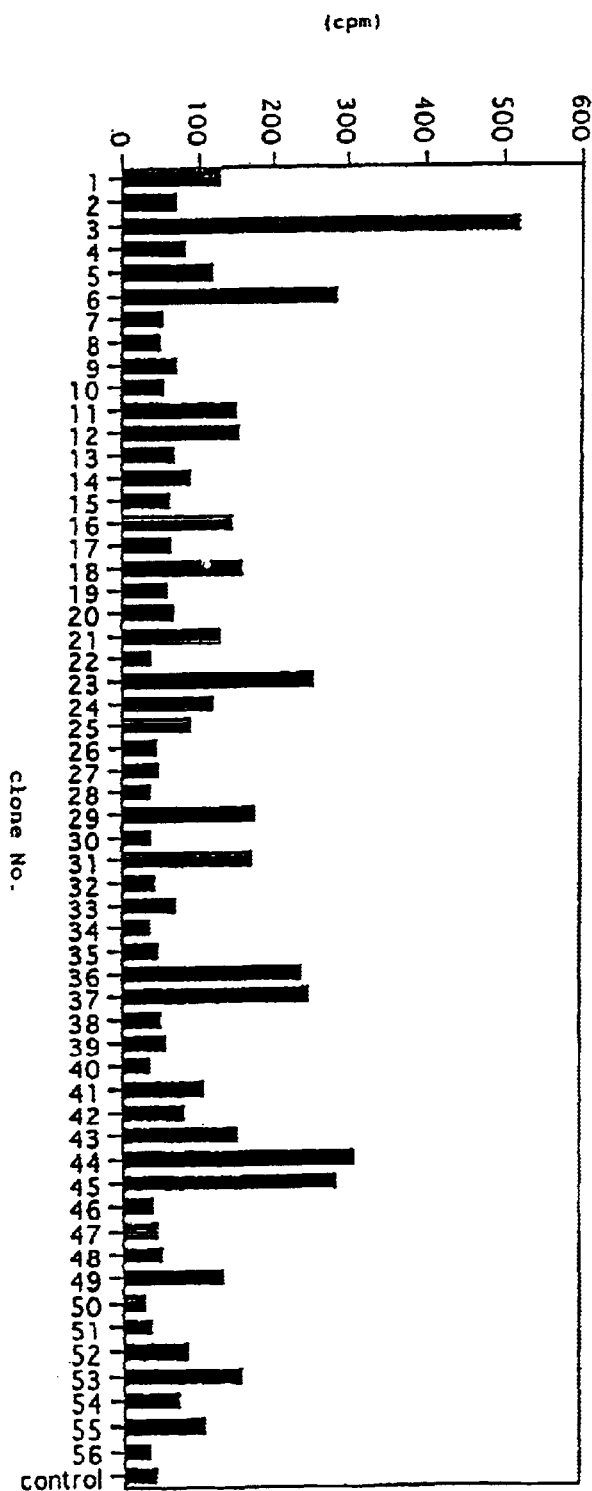
FIG. 4 shows a comparison in an amount of gene expression by in situ hybridization in the rat SLC-1 gene expression CHO cell line.

Selection of the Cho/SLC-1 Cell Line with High Expression of the Full-length Rat SLC-1 Receptor Protein mRNA The expression amounts of the full-length rat SLC-1 receptor protein RNAs of 56 clones from the CHO/SLC-1 strain established in EXAMPLE 3 were measured as follows, using a Cytostar T Plate (Amersham Pharmacia Biotech Co.), in accordance with the protocol attached: Each clone of the CHO/SLC-1 strain was inoculated on a Cytostar T Plate in $2.5 \times 10^4$ cells/well, respectively. After culturing for 24 hours, the cells were fixed with 10% formalin. After 0.25% Triton X-100 was added to each well to increase the cell permeability, $^{35}$S-labeled riboprobe of SEQ ID NO:7 was added to the cells for hybridization. By adding 20 mg/ml of RNaseA to each well, free riboprobe was digested. After the plate was thoroughly washed, radioactivity of the riboprobe hybridized was assayed with a Top counter. The strain with a high radioactivity provides a high expression amount of mRNA. Three clones (#3, #6 and #44) which showed a high expression amount of mRNA were used for the following experiment, especially clone #44 as a main clone (FIG. 4).

Example 5

Camp Synthesis Inhibitory Activity of Mch on Rat SLC-1-Expression Cho Cells

Figure 5:
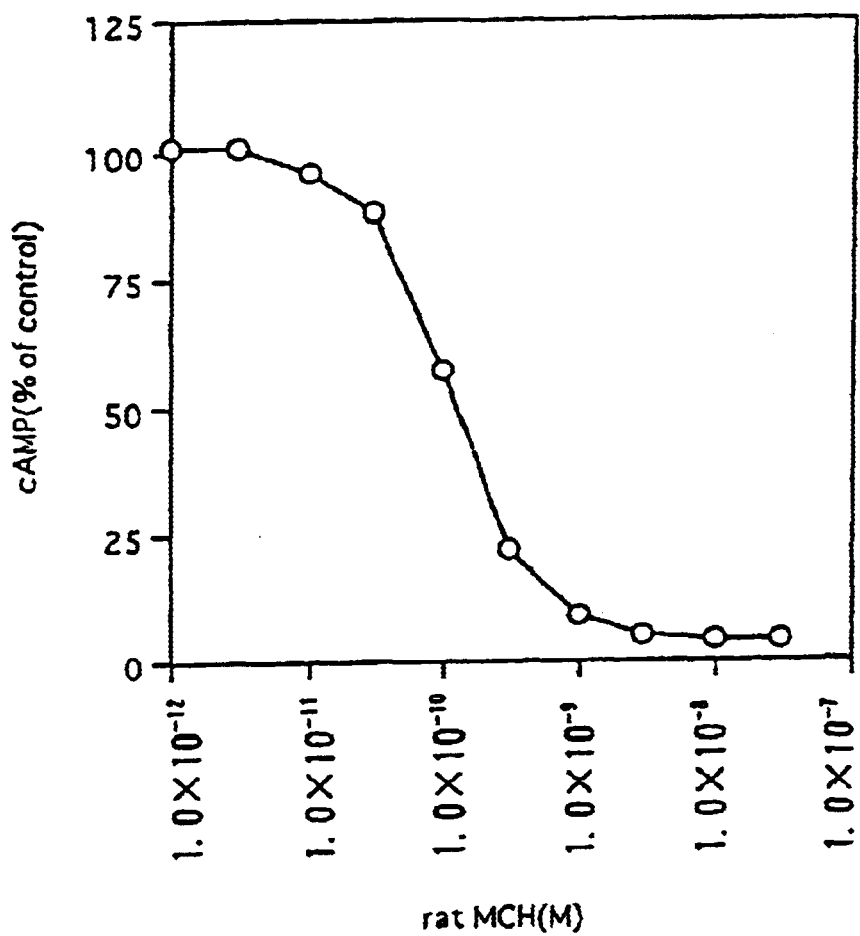
FIG. 5 shows a cAMP synthesis inhibitory activity of MCH in various concentrations on CHO/SLC-1 cells.

The synthetic MCH (Peninsula Co.) was diluted in various concentrations and the cAMP synthesis inhibitory activity was assayed on the rat SLC-1-expression CHO cells by the following method. The CHO/SLC-1 cells selected in EXAMPLE 4 were inoculated on a 24-well plate in $5 \times 10^4$ cells/well followed by cultivation for 48 hours. The cells were then washed with Hanks' balanced salt solution (pH7.4) containing 0.2 mM 3-isobutylmethylxanthine, 0.05% BSA and 20 mM HEPES (hereinafter Hanks' balanced salt solution (pH 7.4) containing 0.2 mM 3-isobutylmethylxanthine, 0.05% BSA and 20 mM HEPES is referred to as a reaction buffer). Subsequently, 0.5 ml of the reaction buffer was added to the cells, which was kept in the medium for 30 minutes. The reaction buffer was removed and 0.25 ml of a fresh reaction buffer was added to the cells. Then, 0.25 ml of the reaction buffer containing various amounts of MCH and 2 µM forskolin was added to the cells followed by reacting at 37° C. for 24 minutes. By adding 100 µl of 20% perchloric acid, the reaction was terminated. The reaction mixture was then allowed to stand on ice for an hour to extract intracellular cAMP. The amount of cAMP in the extract was measured using cAMP EIA kit (Amersham Pharmacia Biotech). The results reveal that MCH obviously reduced the amount of intracellular cAMP in the concentration of 0.1 nM. When the peptide concentration increased, the amount of intracellular cAMP decreased dose-dependently (FIG. 5). In FIG. 5, taking as 100% the amount obtained by subtracting the intracellular cAMP amount when adding the reaction buffer from the intracellular cAMP amount when adding the forskolin-containing reaction buffer, the cAMP synthesis inhibitory activity was expressed by % in terms of the intracellular cAMP amount obtained by subtracting the intracellular cAMP amount when adding the reaction buffer from the intracellular cAMP amount when adding MCH.

Example 6

Figure 6:
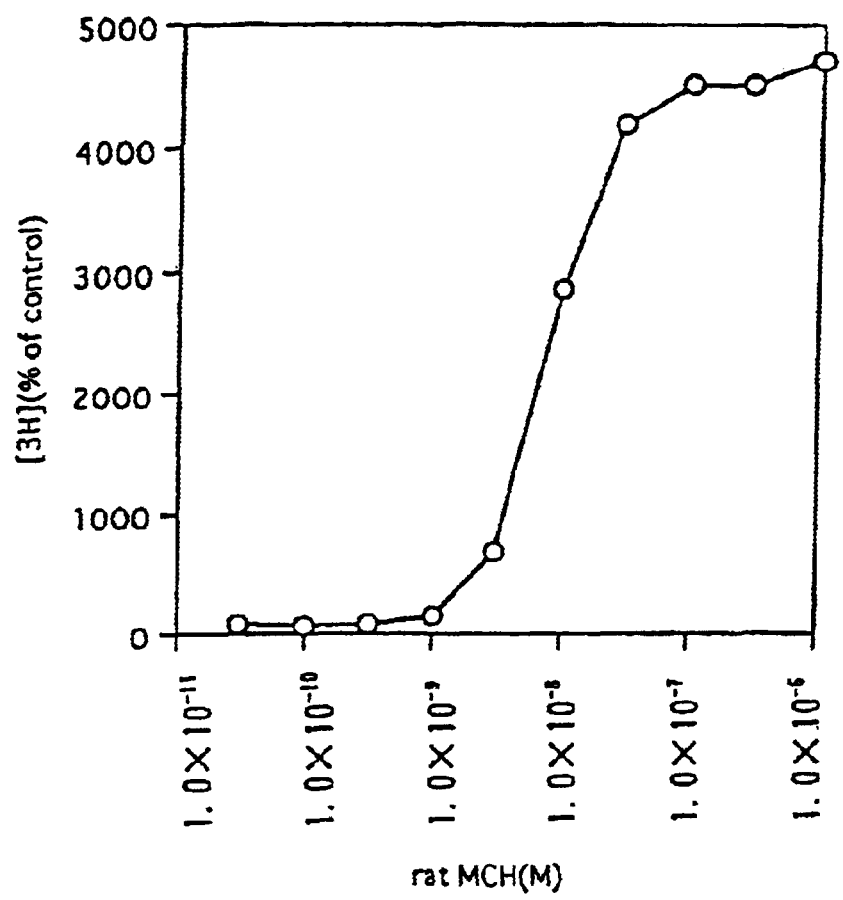
FIG. 6 shows an arachidonic acid metabolite release activity of MCH in various concentrations on CHO/SLC-1 cells.

Arachidonic Acid Metabolite Release Activity Induced by Mch on Rat SLC-1-Expression Cho Cells The arachidonic acid metabolite release activity of the synthetic MCH (Peninsula Co.) in various concentrations on rat SLC-1-expression CHO cells was assayed by the following method. The CHO/SLC-1 cells selected in EXAMPLE 4 were inoculated on a 24-well plate in $5 \times 10^4$ cells/well. After incubation for 24 hours, [$^3$H] arachidonic acid was added to each well in 0.25 µCi/well. Sixteen hours after the addition of [$^3$H] arachidonic acid, the cells were washed with Hanks' balanced salt solution (pH7.4) containing 0.05% BSA and 20 mM HEPES. Then, 500 µl of solutions in various concentrations of the synthetic rat MCH dissolved in Hanks' balanced salt solution (pH 7.4) containing 0.05% BSA and 20 mM HEPES was added to each well. Hereinafter Hanks' balanced salt solution (pH 7.4) containing 0.05% BSA and 20 mM HEPES is referred to as a reaction buffer. After incubating at 37° C. for 60 minutes, 400 µl of the reaction solution was charged in a scintillator and the amount of [$^3$H]arachidonic acid metabolites released into the reaction solution was measured using a scintillation counter. Apparent release of arachidonic acid metabolites occurred with 3 nM of the synthetic rat MCH and when the peptide concentration was further increased, the arachidonic acid metabolites were dose-dependently released into the medium (FIG. 6). In FIG. 6, the arachidonic acid metabolite release activity was expressed in terms of a relative amount of the [$^3$H] arachidonic acid metabolites in the medium when the synthetic rat MCH was added to the reaction buffer, when the amount of the [$^3$H] arachidonic acid metabolites in the reaction buffer added with no synthetic rat MCH was taken as 100%.

Example 7

Isolation of Plasmid Containing Human SLC-1 Cdna

Using a human fetal brain-derived cDNA library (SUPERSCRIPT™ cDNA Library, GIBCO BRL), DNA was nicked using phage F1 endonuclease followed by digesting with *Escherichia coli* exonuclease III, in accordance with the manual of Gene trapper cDNA positive selection system (GIBCO BRL). Thus, a single stranded human fetal brain cDNA library was prepared.

Based on the report by Kolakowski Jr., et al. (Kolakowski Jr., et al. (1996) FEBS Lett. Vol. 398, pp. 253–258), the synthetic oligonucleotide shown by SEQ ID NO:8 (which corresponds to 1434-1451 of accession No. U71092) was prepared. Using a Terminal Deoxynucleotidyl Transferase, biotin-14-dCTP was added to the synthetic oligonucleotide at the 3' end to prepare biotinylated oligonucleotide. The composition of the reaction solution and the reaction time were set as instructed by the manual.

After 4 µg of the single stranded human fetal brain-derived cDNA library was maintained at 95° C. for a minute, the cDNA library was quenched on ice and 20 ng of the biotinylated oligonucleotide was added thereto followed by hybridizing at 37° C. for an hour in a hybridization buffer attached. After adding strepto-avidin beads, the single stranded human fetal brain-derived cDNA hybridized to the biotinylated oligonucleotide was isolated using MAGNA-SEP Magnetic Particle Separator (GIBCO BRL). Using as a primer 50 ng of the synthetic oligonucleotide shown by SEQ ID NO: 9 (which corresponds to 1011–1028 of accession No. U71092) prepared based on the report by Kolakowski Jr. et al. (Kolakowski Jr., et al. (1996) FEBS Lett. Vol. 398, pp. 253–258), the complementary strand was prepared according to the manual, which was made a double stranded plasmid.

Example 8

Determination of a Base Sequence of the Isolated Plasmid Containing the Human SLC-1 Cdna The plasmid obtained in EXAMPLE 7 was introduced into ELECTROMAX™ DH10B™ cells for transformation by electroporation. The clones having a cDNA-inserted fragment were selected in an LB agar medium supplemented with ampicillin and X-gal. Only the clones exhibiting white color were separated from one another by picking at the clones with a sterilized toothpick to obtain transformant *E. coli* DH10B/hSLC-1. The individual clones were cultured overnight in an LB medium containing ampicillin and plasmid DNAs were purified using QIA prep8 mini prep (Qiagen Co.). The reaction for base sequencing was carried out by using a Dye Deoxy Terminator Cycle Sequence Kit (Perkin-Elmer Co.), followed by decoding with a fluorescent automatic sequencer. Thus, the sequence shown by SEQ ID NO:10 was obtained. The amino acid sequence (SEQ ID NO:11) encoded by the base sequence obtained here is different from the putative human SLC-1 amino acid sequence as a sequence deduced from the rat SLC-1 reported by Lakaye et al. (Lakaye, B. et al., (1998) Biochem. Biophys. Acta, Vol. 1401, pp. 216–220), based on the human chromosomal DNA sequence containing the human SLC-1 sequence (accession No. Z86090), indicating that initiation codon ATG is present on mRNA further upstream the 69th and 64th amino acids of the putative sequence. Transformant *Escherichia coli* DH10B/phSLC1L8 by the plasmid bearing a DNA encoding this sequence was on deposit with IFO and NIBH.

Example 9

Assay for Gtpγs Binding Activity to a Rat SLC-1-Expression Cho Cell Membrane Fraction Induced by Mch The binding promoting activity of [$^{35}$S]-guanosine 5'-(γ-thio)triphosphate by MCH to an SLC-1-expression CHO cell membrane fraction was assayed by the following method. First, preparation of the membrane fraction is described. To $1 \times 10^8$ CHO/SLC-1 cells was added 10 ml of a homogenate buffer (10 mM NaHCO$_3$, 5 mM EDTA, 0.5 mM PMSF, 1 µg/ml pepstatin, 4 µg/ml E64, 20 µg/ml leupeptin), followed by cell disruption with a polytron (12,000 rpm, 1 min.). The disrupted cells were then centrifuged (1,000 g, 15 mins.) to give the supernatant. Next, the supernatant was subjected to ultracentrifugation (Beckman type 30 rotor, 30,000 rpm, 1 hour). The resulting precipitate was used as a rat SLC-1-expression CHO cell membrane.

The GTPyS binding activity was assayed as follows. The rat SLC-1-expression CHO cell membrane fraction was diluted with a buffer for membrane dilution (50 mM Tris-hydrochloride buffer (pH 7.4), 5 mM MgCl$_2$, 150 mM NaCl, 1 µM GDP) to make a cell membrane fraction solution for assay having a protein concentration of 30 mg/ml. To 200 µl of the cell membrane fraction solution for assay were added 2 µl of 51.5 nM [$^{35}$S]-guanosine 5-(γ-thio)triphosphate (NEN Co.) and 2 µl of MCH (Peninsula Co.) in various concentrations. The resulting solution mixture was kept at 25° C. for an hour. The mixture was filtrated through a filter. After washing twice with 1.5 ml of a washing buffer (50 mM Tris-hydrochloride buffer (pH 7.4), 5 mM MgCl$_2$, 1 mM EDTA, 0.1% BSA), radioactivity of the filter was measured using a liquid scintillation counter. The MCH dose-dependently increased the amount of ($^{35}$S]-guanosine 5'-(γ-thio) triphosphate bound to the membrane fraction. The MCH in a concentration of about 0.5 nM induced 50% binding which was the total binding.

Example 10

Amplification of Human SLc-1 Cdna by Pcr using Human Fetal Brain-Derived Cdna

Using as a template a plasmid containing human SLC-1 DNA sequence cloned by gene trap, amplification by PCR was performed using the synthetic DNA primers shown by SEQ ID NO:12 and SEQ ID NO:13 and the synthetic DNA primers shown by SEQ ID NO:14 and SEQ ID NO:15, respectively. The former DNA amplified was named human SLC-[(S) and the latter DNA amplified was named human SLC-1 (L). The synthetic DNA primers were constructed to amplify genes in the region to be translated into receptor proteins, whereby recognition sequences of the respective restriction enzymes were added at the 5' and 3' sides so that the base sequence recognized by restriction enzyme Sal I will be added at the 5' side of the gene and the base sequence recognized by restriction enzyme Spe I at the 3' side. The reaction solution for amplifying human SLC-1 (S) was composed of 5 µl of the plasmid template containing the human SLC-1 DNA sequence, 0.4 µM each of the synthetic DNA primers, 0.2 mM dNTPs, 0.5 µl of pfu DNA polymerase and a buffer attached to the enzyme, which were mixed together to make the total volume 50 µl. Using a Thermal Cycler (Perkin-Elmer Co.) for amplification, heating at 94° C. for 60 seconds was followed by repeating 25 times a cycle set to include 94° C. for 60 seconds, 57° C. for 60 seconds and 72° C. for 150 seconds, and finally maintaining at 72° C. for 10 minutes. The reaction solution for amplifying human SLC-1 (L) was composed of 5 µl of the plasmid template containing the human SLC-1 DNA sequence, 0.4 µM each of the synthetic DNA primers, 0.2 mM dNTPs, 0.5 µl of pfu DNA polymerase and a buffer attached to the enzyme, which were mixed together to make the total volume 50 µl. Using a Thermal Cycler (Perkin-Elmer Co.) for amplification, heating at 94° C. for 60 seconds was followed by repeating 25 times a cycle set to include 94° C. for 60 seconds, 60° C. for 60 seconds and 72° C. for 3 minutes, and finally maintaining at 72° C. for 10 minutes. The amplified products were confirmed by 0.8% agarose gel electrophoresis followed by staining with ethidium bromide.

Example 11

Subcloning of the Pcr Products into Plasmid Vectors and Confirmation of the Amplified Cdna Sequences by Decoding Base Sequences of the Inserted Cdna Region The PCR products obtained by PCR in EXAMPLE 10 were separated by using a 0.8% low melting point agarose gel. The band part was excised from the gel with a razor blade, cut into small pieces and extracted with phenol and then with phenol/chloroform. The extract was precipitated in ethanol to recover DNAs. According to the protocol attached to PCR-Script™ Amp SK(⁺) Cloning Kit (Stratagene Co.), the recovered DNAs were subcloned to plasmid vector pCR-Script Amp SK(⁺). The recombinant vector was introduced into *Escherichia coli* DH5α competent cells (Toyobo.) to produce transformants. The clones having a cDNA-inserted fragment were selected in an LB agar medium containing ampicillin and X-gal. Only the clones exhibiting white color were picked up with a sterilized toothpick to obtain transformant *E. coli* DH5α/hSLC-1(S) of human SLC-[(S) and transformant *E. coli* DH5α/hSLC-1(L) of human SLC-1(L). The individual clones were cultured overnight in an LB medium containing ampicillin. Plasmid DNAs were prepared using QIA prep8 mini prep (Qiagen Co.). An aliquot of the DNAs thus prepared was cleaved by restriction enzymes Sal I and Spe I to confirm the size of the receptor cDNA fragment inserted. The reaction for base sequencing was carried out by using a DyeDeoxy Terminator Cycle Sequence Kit (Perkin-Elmer Co.), followed by decoding with a fluorescent automatic sequencer. The sequences of the clones obtained were in agreement, respectively, with the DNA sequence (SEQ ID NO:16) to be amplified by the synthetic DNA primers shown by SEQ ID NO:12 and SEQ ID NO:13 using the human SLC-1 gene as a template, and the DNA sequence (SEQ ID NO:17) to be amplified by the synthetic DNA primers shown by SEQ ID NO:14 and SEQ ID NO:15 using the human SLC-1 gene as a template.

Example 12

Preparation of Human SLc-L(S)-Expression Cho Cells and Human SLC-1(L)-Expression Cho Cells Using Plasmid Midi Kit (Qiagen Co.), plasmids were prepared from clones of *E. coli* transformed by the human SLC-1(S)— and human SLC-1(L)-introduced plasmids, whose sequences were confirmed in EXAMPLE 11. The plasmids were cleaved with restriction enzymes Sal I and Spe I to excise the insert part out. After electrophoresis, the inserted DNA was excised from the agarose gel with a razor blade, cut into small pieces and extracted with phenol and then with phenol/chloroform. The extract was precipitated in ethanol to recover the inserted DNA. The inserted DNA was added to Sal I- and Spe I-cleaved vector plasmid pAKK0-111H for animal cell expression (same as the vector plasmid pAKK01. 11H described in Hinuma, S. et al., Biochim. Biophys. Acta, Vol. 1219, pp. 251–259 (1994)) followed by ligation using T4 ligase (Takara Shuzo Co.). Thus, plasmids pAKK0-hSLC-1(S) and pAKK0-hSLC-1(L) for protein expression were constructed.

After *E. coli* DH5α (Toyobo) transformed by pAKK0-hSLC-1(S) and pAKK0-hSLC-1(L) was cultured, plasmid DNAs of pAKK0-hSLC-1(S) and pAKK0-hSLC-1(L) were prepared using Plasmid Midi Kit (Qiagen Co.). Using Cell Phect Transfection Kit (Amersham Pharmacia Biotech Co.), the plasmid DNAs were introduced into CHO dhfr cells, according to the protocol attached to the Kit. DNA, 10 µg, was co-precipitated with calcium phosphate in suspension. The suspension was added to a 10 cm Petri dish on which $5 \times 10^5$ or $1 \times 10^6$ CHO dhfr cells had been inoculated before 24 hours. The cells were cultured for one day in MEMα medium containing 10% calf fetal serum. After passage, the cells were cultured in nucleic acid-free MEMα medium for selection containing 10% dialyzed calf fetal serum. As clones growing in the selection medium, 56 clones of the transformant human SLC-1(S)-transfected CHO cells and 61 clones of the transformant human SLC-1(L)-transfected CHO cells were selected.

Example 13

Selection of Transfectant Cell Line with High Expression of Human SLC-1(S) and Human SLC-1 (L) mRNAs The expression amounts of the mRNAs of 56 clones from the CHO/hSLC-1(S) strain and 61 clones from the CHO/hSLC-1(L) strain established in EXAMPLE 12, were measured as follows, using a Cytostar T Plate (Amersham Pharmacia Biotech Co.), in accordance with the protocol attached. Each clone of the CHO/hSLC-1(S) strain and CHO/hSLC-1(L) strain was inoculated on each well of the Cytostar T Plate in $2.5 \times 10^4$ cells/well. After culturing for 24 hours, the cells were fixed with 10% formalin. After 0.25% Triton X-100 was added to each well to increase the cell permeability, $^{35}$S-labeled riboprobe of SEQ ID NO: 18 was added to the cells to hybridize them. By adding 20 mg/ml RNaseA to each well, free riboprobe was digested. After the plate was thoroughly washed, radioactivity of the hybridized riboprobe was measured with a Topcounter. The strain with a high radioactivity provides a high expression amount of mRNA.

Example 14 cAMP Synthesis Inhibitory Activity of MCH on Human SLC-1-Expression CHO Cells

The synthetic MCH (Peninsula Co.) was diluted in various concentrations and the cAMP synthesis inhibitory activity was assayed on the human SLC-1-expression CHO cells by the following method. The CHO/hSLC-1(S) strain or the CHO/hSLC-1(L) strain, which was human SLC-1-expression CHO cells selected in EXAMPLE 13, was inoculated on a 24-well plate in $5 \times 10^4$ cells/well followed by cultivation for 48 hours. The cells were then washed with Hanks' balanced salt solution (pH 7.4) containing 0.2 mM 3-isobutylmethylxanthine, 0.05% BSA and 20 mM HEPES (hereinafter Hanks' balanced salt solution (pH 7.4) containing 0.2 mM 3-isobutylmethylxanthine, 0.05% BSA and 20 mM HEPES is referred to as a reaction buffer). Subsequently, 0.5 ml of the reaction buffer was added to the cells, which was maintained in the medium for 30 minutes. The reaction buffer was removed and 0.25 ml of a fresh reaction buffer was added to the cells. Then, 0.25 ml of the reaction buffer containing various amounts of MCH and 2 µM forskolin was added to the cells followed by reacting at 37° C. for 24 minutes. By adding 100 µl of 20% perchloric acid, the reaction was terminated. Next, the reaction mixture was allowed to stand on ice for an hour to extract intracellular cAMP. The amount of cAMP in the extract was measured using cAMP EIA kit (Amersham Pharmacia Biotech). The results reveal that the MCH decreased dose-dependently the amount of intracellular cAMP in the human SLC-1 expression cells.

Example 15

Arachidonic Acid Metabolite Release Activity Induced by MCH on Human SLC-1-expression CHO Cells The arachidonic acid metabolite release activity of the synthetic MCH (Peninsula Co.) in various concentrations on human SLC-1-expression CHO cells was assayed by the following method. The CHO/hSLC-1(S) strain or the CHO/hSLC-1(L) strain, which was human SLC-1-expression CHO cells selected in EXAMPLE 13, were inoculated on a 24-well plate in $5 \times 10^4$ cells/well. After incubation for 24 hours, [$^3$H] arachidonic acid was added in 0.25 µCi/well. Sixteen hours after the addition of [$^3$H] arachidonic acid, the cells were washed with Hanks' balanced salt solution (pH 7.4) containing 0.05% BSA and 20 mM HEPES. Then, 500 µl of solutions in various concentrations of the synthetic MCH dissolved in Hanks' balanced salt solution (pH 7.4) containing 0.05% BSA and 20 mM HEPES was added to each well. Hereinafter, Hanks' balanced salt solution (pH7.4) containing 0.05% BSA and 20 mM HEPES is referred to as a reaction buffer. After incubating at 37° C. for 60 minutes, 400 µl of the reaction solution was charged in a scintillator and the amount of [$^3$H] arachidonic acid metabolites released into the reaction solution was measured using a scintillation counter. The results reveal that the synthetic MCH showed the arachidonic acid metabolite release activity dose-dependently on the human SLC-1 expression cells.

Example 16

Assay for GTPγS Binding Activity Using a Human Slc-1-Expression Cho Cell Membrane Fraction A human SLC-1-expression CHO cell membrane fraction was prepared by the following procedure. Human SLC-1-expression CHO cells ($1 \times 10^8$ cells) were suspended in phosphate buffered saline (pH 7.4) supplemented with 5 mM EDTA (ethylene diamine tetra acetic acid) followed by centrifugation. after 10 ml of a homogenate buffer (10 mM NaHCO$_3$, 5 mM EDTA, pH 7.5) was added to the cell pellets, the mixture was homogenized with a polytron homogenizer. the homogenate was then centrifuged at 400×g for 15 minutes. the resulting supernatant was further centrifuged at 100,000×g for an hour to give membrane fraction precipitates. the precipitates were suspended in 2 ml of an assay buffer (50 mM Tris-HCl (pH 7.5), 1 mM EDTA, 0.1% BSA (bovine serum albumin), 10 mM MgCl$_2$, 100 mM NaCl, 1 mM GDP (guanosine 5'-diphosphate), 0.25 mM PMSF (phenylmethylsulfonyl fluoride), 1 µg/ml pepstatin, 20 µg/ml leupeptin, 10 µg/ml phosphoramidon] and the suspension was centrifuged at 100,000×g for an hour. the cell membrane recovered as precipitates was resuspended in 20 ml of the assay buffer. after dispensing, the suspension was stored at −80° C., which may be thawed every time at use.

The GTPγS binding activity was assayed as follows. the human SLC-1-expression CHO cell membrane fraction was diluted with the assay buffer. after dispensing 173 µl each of the dilution in a polypropylene-made 96-well plate, 2 µl of a DMSO solution of MCH (manufactured by Bachem Co.) in various concentrations and 25 µl of [$^{35}$S]-guanosine 5'-(γ-thio) triphosphate (manufactured by Daiichi Kagaku Yakuhin K. K.) were added to each well at the same time (final concentration of the cell membrane: 20 μg/ml, final concentration of [$^{35}$S]-guanosine 5'-(γ-thio) triphosphate: 0.33 nM). after reacting at 25° C. for an hour while stirring, the reaction solution was subjected to suction filtration through a glass filter (GF-C). the filtrate was further washed 3 times with 300 μl of washing liquid (50 mM Tris-HCl buffer, pH 7.5). after adding 50 μl of a liquid scintillator to the glass filter, the residual radioactivity was measured using a liquid scintillation counter.

The MCH increased dose-dependently the amount of [$^{35}$]-guanosine 5'-(γ-thio) triphosphate bound to the human SLC-1-expression CHO cell membrane fraction. Also, $ED_{50}$ value of the MCH to the human SLC-1-expression CHO cell membrane fraction was 0.2 nM.

Example 17

Preparation of MCH (2-19), MCH(3-19), MCH(4-19), MCH(5-19), MCH(6-19) and MCH(7-19) (SEQ ID NO:19-NO:24) by Manually Operated Edman Degradation In 30 μl of 50% pyridine 0.1 mg of MCH (Sigma Co.) was dissolved and 1 μl of phenyl isothiocyanate (Wako Pure Chemical Industries) was added to the solution for nitrogen substitution. the mixture was then kept at 45° C. and stirring was made every 10 minutes. an hour later, the mixture was ceased to keep warm and evaporated to dryness in a nitrogen flow. the residue was again dissolved in 20 μl of ethanol. the solution was evaporated to dryness by distilling the solvent off in vacuum. the reaction product or phenyl thiocarbamoyl derivative was dissolved in 20 μl of trifluoroacetic acid (Wako Pure Chemical Industries) followed by nitrogen substitution. by keeping warm at 45° C. for 20 minutes, the amino terminal amino acid of the peptide was cleaved into the anilinothiazolinone derivative. after removing trifluoroacetic acid in a nitrogen flow, 30 μl of water and 100 μl of n-butyl acetate were added to the solution. the mixture was extracted with n-butyl acetate to remove an excess of reagents and the anilinothiazolinone derivative. the extraction with n-butyl acetate was repeated 3 times. Subsequently, the aqueous phase containing MCH(2-19) with the amino terminus shortened by one residue was evaporated to dryness in vacuum in a nitrogen flow.

This degradation process was performed only once so that MCH(2-19) with only one residue deleted at the N terminus was obtained. the same degradation process was repeated 2. 3, 4, 5 or 6 times to give MCH(3-19). MCH(4-19). MCH (5-19), MCH(6-19) and MCH(7-19) with only one residue each of the N-terminal amino groups being deleted, respectively.

MCH(2-19), MCH(3-19), MCH(4-19), MCH(5-19), MCH(6-19) and MCH(7-19) obtained by the degradation described above were purified as follows and, their structures were confirmed by mass spectrometry and amino acid analysis. Though the details are focused on MCH(4-19) below, other derivatives were treated in almost the same way. the thus obtained analytical data on MCH(2-19), MCH (3-19), MCH(4-19), MCH(5-19), MCH(6-19) and MCH(7-19) are shown in TABLE 1.

TABLE 1

Data on MCH(2-19), MCH(3-19), MCH(4-19), MCH(5-19), MCH(6-19) and MCH(7-19) by mass spectrometry and amino acid analysis

| Structure | Mass spectrum (M + H$^+$) found (calcd.) Formula | Amino acid analysis (No. of residues) |
| --- | --- | --- |
| MCH(2-19) | (2272.1) $C_{101}H_{156}N_{29}O_{23}S_4$ | D 1.90 (1), E 2.28 (1), P 1.32 (1), G 2.33 (1), V 1.76 (2), C n. d. (1), M 0.46 (2), L 2.0 (2), Y 0.50 (1), F 0.93 (1), R 1.98 (3) |
| MCH(3-19) | (2125.0) $C_{92}H_{147}N_{28}O_{22}S_4$ | D 1.01 (1), E 1.05 (1), P 1.25 (1), G 1.02 (1), V 1.9 (2), C 0.30 (1), M 1.37 (2), L 2.0 (2), Y 0.20 (1), R 2.94 (3) |
| MCH(4-19) | (2010.0) $C_{88}H_{142}N_{27}O_{19}S_4$ | E 1.04 (1), P 1.12 (1), G 1.02 (1), V 1.88 (2), C 0.34 (1), M 1.42 (2), L 2.0 (2), Y 0.23 (1), R 2.93 (3) |
| MCH(5-19) | (1878.9) $C_{83}H_{133}N_{26}O_{18}S_3$ | E 1.51 (1), P 0.69 (1), G 2.16 (1), V 1.27 (2), C n. d. (1), M 0.38 (1), L 2.0 (2), Y 0.18 (1), R 1.80 (3) |
| MCH(6-19) | (1765.9) $C_{77}H_{122}N_{25}O_{17}S_3$ | E 0.69 (1), P 0.79 (1), G 0.70 (1), V 1.21 (2), C 0.15 (1), M 0.50 (1), L 1.0 (1), Y 0.20 (1), R 1.84 (3) |
| MCH(7-19) | 1609.2(1608.8) $C_{71}H_{110}N_{21}O_{16}S_3$ | E 0.90 (1), P 0.62 (1), G 1.03 (1), V 1.05 (2), C 0.07 (1), M 0.33 (1), L 1.0 (1), Y 0.15 (1), R 1.04 (2) |

Using HPLC, MCH(4-19) was purified as follows. Eluant a (0.1% trifluoroacetic acid) was previously passed through a Spheri-5RP-18 column for reverse phase high performance liquid chromatography (Brown-Lee Inc., 2.1 mm×30 mm) at a flow rate of 300 μl/min, to equilibrate the column at 25° C. the reaction product was dissolved in 270 μl of 0.1% trifluoroacetic acid. after pouring a 50 μl aliquot onto the column, the concentration of eluant B (0.1% trifluoro acetic acid/70% acetonitrile) was increased to 70% over 30 minutes while maintaining the flow rate at 300 μl/min. the eluate was monitored at 210 nm in absorbance and the peaks were manually fractionated. MCH(4-19) was eluted in 17.1 minutes. MCH(4-19) collected in one test tube was concentrated to dryness and the residue was dissolved in 100 μl of DMSO.

Mass spectrometry was performed by the LSIMS method using JEOL JMS-HX110. that is, 1 μl of a matrix of 3-nitrobenzyl alcohol and glycerol in 3:2 was mixed with 1 μl of a sample fluid on a probe chip. the mixture was introduced into an ion source. Cesium ions accelerated to 15 kV were irradiated and positive secondary ions formed were accelerated to 10 kV, which was led to a detector.

For amino acid analysis, hydrolysis was carried out by taking 5 μl of a sample fluid in a glass tube, drying to solid in vacuum, putting the residue in a vial, charging 200 μl of 6N azeotropic hydrochloric acid (Pierce Co., Sequenal Grade) at the bottom of the vial, deaerating in accordance with the protocol recommended by Waters, Co. using Pico-Tag Work Station by Waters, Co., and then maintaining at 110° C., for 24 hours.

The hydrochloric acid in the reaction vial was removed in vacuum through a vacuum pump, and the sample fluid was diluted with 150 μl of 20 mM hydrochloric acid. the dilution was charged in a vial for analysis, which was set in an amino acid analyzer and a 100 μl aliquot was provided for the analysis. Using a Hitachi L-8500 high speed amino acid analyzer, the amino acid analysis was performed by fluorometry using ortho-phthalaldehyde reagent (Wako Pure Chemical Industries) for derivatization. Preparation of a buffer for fluorometry, preparation of the reaction solution and conditions for analysis were followed in the manual of the L-8500 amino acid analyzer. a molar ratio of the measurement data based on leucine is given in TABLE 1.

Also, MCH or MCH(2-19), MCH(3-19), MCH(4-19) and MCH(5-19) can also be prepared by the solid phase synthesis described in EXAMPLES 24 through 28.

Example 18

Derivatization of MCH, MCH(2-19), MCH(3-19). MCH(4-19) and MCH(5-19) with a non-isotope Bolton-Hunter Reagent MCH and, MCH(2-19), MCH(3-19), MCH(4-19), MCH (5-19) and MCH(6-19) obtained in EXAMPLE 17 were derivatized with anon-isotope Bolton-Hunter reagent. Taking derivatization of MCH(4-19) as an example, its procedure is described below.

After 1 nmol of MCH(4-19) was dissolved in 50 μl of dimethylformamide, 100 nmols of N-succinimidyl 3-(4-hydroxy-3-iodophenyl)propionate (Wako Pure Chemical Industries) as a non-isotope Bolton-Hunter reagent and 100 nmols of N, N-diisopropylethylamine (Wako Pure Chemical Industries) were added to the solution. the mixture was reacted at 37° C. for 4 hours.

After 450 μl of 10% acetonitrile containing 0.1% trifluoroacetic acid was added to the reaction mixture, the mixture was purified by HPLC. Conditions for the chromatography are given below. Wakosil-II 5C18HG (4.6×150 mm) was used as a column at a flow rate of 1.0 ml/min. Using asqueous acetonitrile solution containing 0.1% trifluoroacetic acid, elution was performed by maintaining the acetonitrile concentration at 10% for 2 minutes, then increasing up to 20% over 5 minutes and then increasing up to 50% over 20 minutes. [N-(3-(4-Hydroxy-3-iodophenyl)propionyl)-Met$^4$]-MCH(4-19) derivatized from MCH(4-19) with the non-isotope Bolton-Hunter reagent was eluted in 22.9 minutes, which was manually fractionated. MCH or MCH (2-19), MCH(3-19). MCH(5-19) and MCH(6-19) were derivatized in substantially the same way by introducing 3-(4-hydroxy-3-iodophenyl)propionyl group at the amino group of the N-terminal amino acid. the derivatives were fractionated by HPLC. Acidic hydrolysis of these derivatives in a manner similar to the procedure described in EXAMPLE 17 was followed by amino acid analysis. the results are shown in TABLE 2.

TABLE 2

| Amino acid analysis data on derivatized MCH(2-19), MCH(3-19), MCH(4-19), MCH(5-19) and MCH(6-19) | |
|---|---|
| Structure | Amino Acid Analysis Data (No. of residues) |
| Derivatized MCH(2-19) | D 1.01 (1), E 1.05 (1), P 0.86 (1), G 1.09 (1), V 1.69 (2), C n. d. (1), M 1.01 (2), L 2.0 (2), Y 0.27 (1), F 0.90 (1), R 2.59 (3) |
| Derivatized | D 1.20 (1), E 1.58 (1), P 1.12 (1), G 2.07 |

TABLE 2-continued

| Amino acid analysis data on derivatized MCH(2-19), MCH(3-19), MCH(4-19), MCH(5-19) and MCH(6-19) | |
|---|---|
| Structure | Amino Acid Analysis Data (No. of residues) |
| MCH(3-19) | (1), V 1.60 (2), C n. d. (1), M 0.94 (2), L 2.0 (2), Y 0.19 (1), R 2.24 (3) |
| Derivatized MCH(4-19) | E 1.09 (1), P 1.46 (1), G 1.09 (1), V 1.83 (2), C n. d. (1), M 1.14 (2), L 2.0 (2), Y 0.27 (1), R 2.78 (3) |
| Derivatized MCH(5-19) | E 1.10 (1), P 0.90 (1), G 1.34 (1), V 1.55 (2), C n. d. (1), M 0.32 (1), L 2.0 (2), Y 0.32 (1), R 2.28 (3) |

Example 19

Preparation of radioisotope-labeled MCH(4-19)

MCH(4-19) prepared in EXAMPLE 17, in which 3 residues of the N-terminal amino acid were deleted from MCH, was labeled with a radioisotope according to the Bolton-Hunter method. in a tube, dry nitrogen gas was blown into a solution of 9.25 MBq (0.11 nmol) of [$^{125}$I]-Bolton-Hunter reagent (N-succinimidyl 3-(4-hydroxy-3-iodophenyl) propionate) (NEN Life Science Products Co., 81.4 TBq/mmol) in benzene to remove the benzene by distillation. in the tube were added 18 μl of 50 mM phosphate buffer (pH7.5), 2.3 nmols of MCH(4-19) dissolved in 1.5 μl of dimethylsulfoxide and 0.5 μl of dimethylsulfoxide. the mixture was thoroughly mixed. after keeping the liquid mixture at 37° C. for 2 hours, [$^{125}$I]-[N-(3-(4-hydroxy-3-iodophenyl) propionyl)-Met$^4$]-MC H(4-19) (structural formula is described in (4) supra), which is a radioactive derivative of MCH(4-19) with the a Bolton-Hunter reagent, was fractionated by reverse phase HPLC. [$^{125}$I]-[N-(3-(4-Hydroxy-3-iodophenyl)propionyl)-Met$^4$]-MC H(4-19) was eluted at about 43.6% acetonitrile concentration through an ODS column (TOSO, ODS-80TM (4.6 mm×150 mm)).

In a similar manner, radioisotope-labeled derivatives of MCH, MCH(2-19), MCH(3-19), MCH(5-19), MCH(6-19) and MCH(7-19) ((1) through (3) and (5) through (7) supra) can be prepared by introducing. [$^{125}$I]-(3-(4-hydroxy-3-iodophenyl)propionyl group into the amino group of the N-terminal amino acid, using [$^{125}$I]-Bolton-Hunter reagent.

Example 20

Preparation of Radioactive iodine-labeled MCH, MCH(2-19), MCH(3-19), MCH(4-19), MCH(5-19), MCH(6-19) and MCH(7-19)

Isotope-labeled MCH, MCH(2-19), MCH(3-19), MCH(4-19), MCH(5-19), MCH(6-19) and MCH(7-19) may also be prepared as follows, by converting Tyr$^{13}$ in the amino acid sequence into radioactive iodine. Taking MCH(4-19) as an example, its procedure will be described below but radioactive iodine derivatives of MCH, MCH(2-19), MCH(3-19), MCH(5-19), MCH(6-19) and MCH(7-19) can be prepared as in MCH(4-19).

In 25 μl of 0.4 M sodium acetate (pH 5.6) was dissolved 5 μg of MCH(4-19). after 200 ng of lacto-peroxidase (manufactured by Wako Pure Chemical Industries) was added to the solution, 1 mCi of [$^{125}$I]-sodium iodide (Amersham Pharmacia Biotech Co.) and 200 ng of hydrogen peroxide (10 μl) were added to the mixture. after allowing to stand for 10 minutes at room temperature, 200 ng of hydrogen peroxide (10 μl) was further added to the mixture. the resulting mixture was then allowed to stand for 10 minutes. the mixture was purified by HPLC using a TSKgel ODS-80Ts column (4.6 mm×25 cm, TOSO) gave [$^{125}$I]-labeled MCH(4-19).

Example 21

Assay for the Agonist Activity of MCH, MCH(2-19), MCH(3-19), MCH(4-19), MCH(5-19), MCH (6-19) and MCH(7-19) using the GTPγS Binding Assay A rat SLC-1-expression CHO cell membrane fraction was prepared by the following procedure. Rat SLC-1-expression CHO cells (1×10$^8$ cells) were suspended in phosphate buffered saline (pH 7.4) supplemented with 5 mM EDTA (ethylene diamine tetra acetic acid) followed by centrifugation. after 10 ml of a homogenate buffer (10 mM NaHCO$_3$, 5 mM EDTA, pH 7.5) was added to the cell pellets, the mixture was homogenized with a polytron homogenizer. the homogenate was then centrifuged at 400×g for 15 minutes. the resulting supernatant was further centrifuged at 100,000×g for an hour to give membrane fraction precipitates. the precipitates were suspended in 2 ml of an assay buffer (50 mM Tris-HCl (pH 7.5), 1 mM EDTA, 0.1% BSA (bovine serum albumin), 10 mM MgCl$_2$, 100 mM NaCl, 1 μM GDP (guanosine 5'-diphosphate), 0.25 mM PMSF (phenylmethylsulfonyl fluoride), 1 μg/ml pepstatin, 20 μg/ml leupeptin, 10 μg/ml phosphoramidon). the suspension was centrifuged at 100,000×g for an hour. the cell membrane recovered as precipitates was resuspended in 20 ml of the assay buffer. after dispensing, the suspension was stored at −80° C., which maybe thawed every time upon use.

The agonist activity of MCH, MCH(2-19), MCH(3-19), MCH(4-19), MCH(5-19), MCH(6-19) and MCH(7-19) was assayed as follows. the rat SLC-1-expression CHO cell membrane fraction was diluted with the assay buffer. after dispensing 173 μl each of the dilution in a polypropylene-made 96-well plate, 2 μl of solutions of MCH, MCH(2-19), MCH(3-19), MCH(4-19), MCH(5-19), MCH(6-19) and MCH(7-19) diluted with DMSO solution in various concentrations and 25 μl of [$^{35}$S]-guanosine 5'-(γ-thio) triphosphate (manufactured by Daiichi Kagaku Yakuhin K. K.) were charged in each well at the same time (the final concentration of cell membrane: 20 μg/ml, the final concentration of [$^{35}$S]-guanosine 5'-(γ-thio)triphosphate: 0.33 nM). the reaction solution was reacted at 25° C. for an hour while stirring. the mixture was then subjected to suction filtration through a glass filter (GF-C). the filtrate was further washed 3 times with 300 μl of washing liquid (50 mM Tris-HCl buffer, pH 7.5). after adding 50 μl of a liquid scintillator to the glass filter, the residual radioactivity was measured using a liquid scintillation counter.

Figure 7:
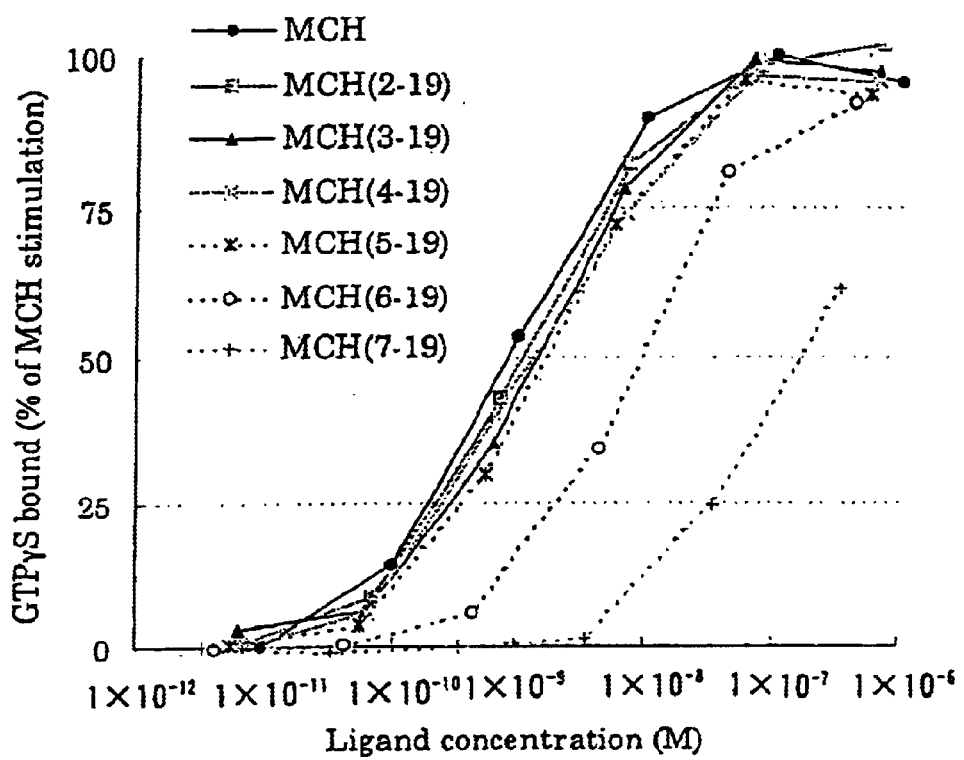
FIG. 7 shows results obtained by assaying an agonist activity of MCH, MCH(2-19), MCH(3-19), MCH(4-19), MCH(5-19), MCH(6-19) and MCH(7-19), using GTPyS-binding assay.

The agonist activity of MCH(6-19) and MCH(7-19) decreased by approximately 10 times and 200 times, respectively, as compared to that of MCH, whereas MCH) 2-19), MCH)$_3$-19), MCH(4-19) and MCH(5-19) showed almost the same agonist activity (FIG. 7).

Example 22

Assay for the Agonist Activity of Mch, Mch(2-19), MCH(3-19), MCH(4-19) and MCH(5-19) Derivatized with a non-isotope Bolton-Hunter Reagent, using the GTPγS Binding Assay The agonist activity of the non-isotope Bolton-Hunter reagent-derivatized MCH, MCH(2-19), MCH(3-19), MCH (4-19) and MCH(5-19) obtained in EXAMPLE 18 was assayed using the GTPγS binding assay in the same way as in EXAMPLE 21.

Figure 8:
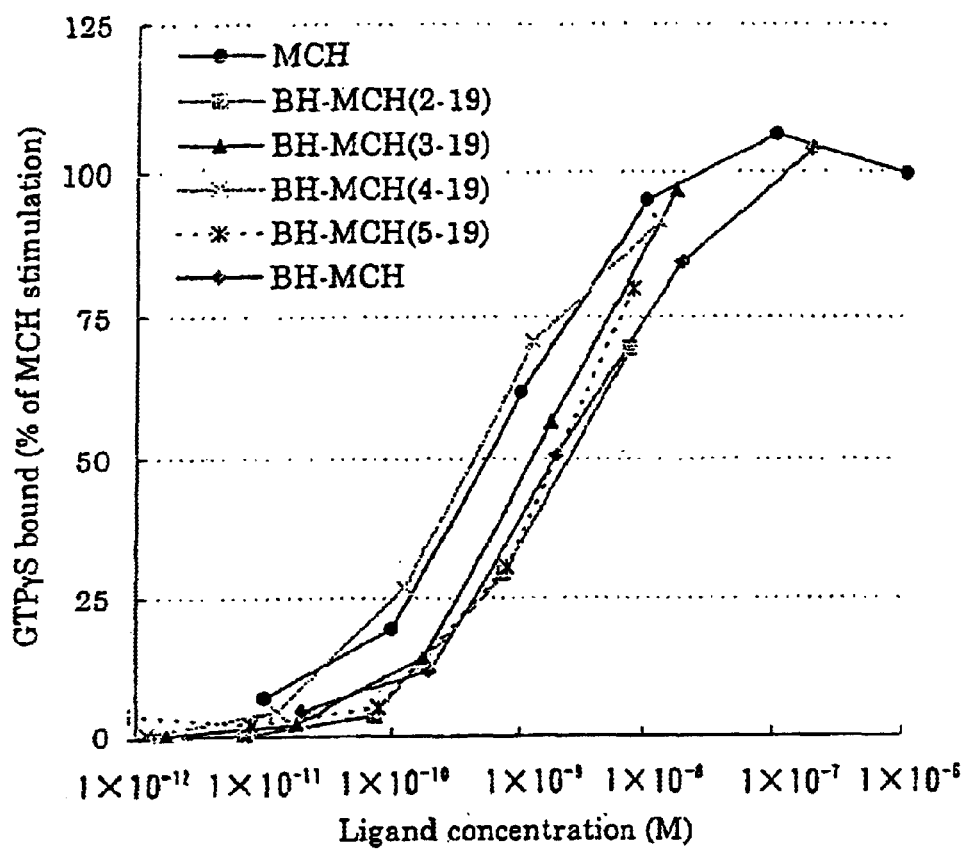
FIG. 8 shows results obtained by assaying an agonist activity of MCH, MCH(2-19), MCH(3-19), MCH(4-19) and MCH(5-19) derivatized with a non-isotope Bolton-Hunter reagent, using GTPyS-binding assay.

The derivatized MCH, MCH(2-19), MCH(3-19), MCH (4-19) and MCH(5-19) increased dose-dependently the amount of [$^{35}$S]-guanosine 5'-(γ-thio) triphosphate bound to the human SLC-1-expression CHO cell membrane fraction, confirming that various MCHs derivatized with a non-isotope Bolton-Hunter reagent exhibit the agonist activity (FIG. 8). in the figure, BH-MCH, BH-MCH(2-19), BH-MCH(3-19), BH-MCH(4-19) and BH-MCH(5-19) designate MCH, MCH(2-19), MCH(3-19), MCH(4-19) and MCH(5-19) derivatized with a non-isotope Bolton-Hunter reagent, respectively.

Example 23

Receptor Binding Test Using [$^{125}$I]-Labeled MCH (4-19) Prepared using a Bolton-Hunter Reagent A receptor binding test was carried out using the [$^{125}$I]-labeled MCH (4-19) (whose structure is described in (4) supra) prepared in EXAMPLE 19 using a Bolton-Hunter reagent and the cell membrane fraction prepared from the human SLC-1-expression CHO cells.

Figure 9:
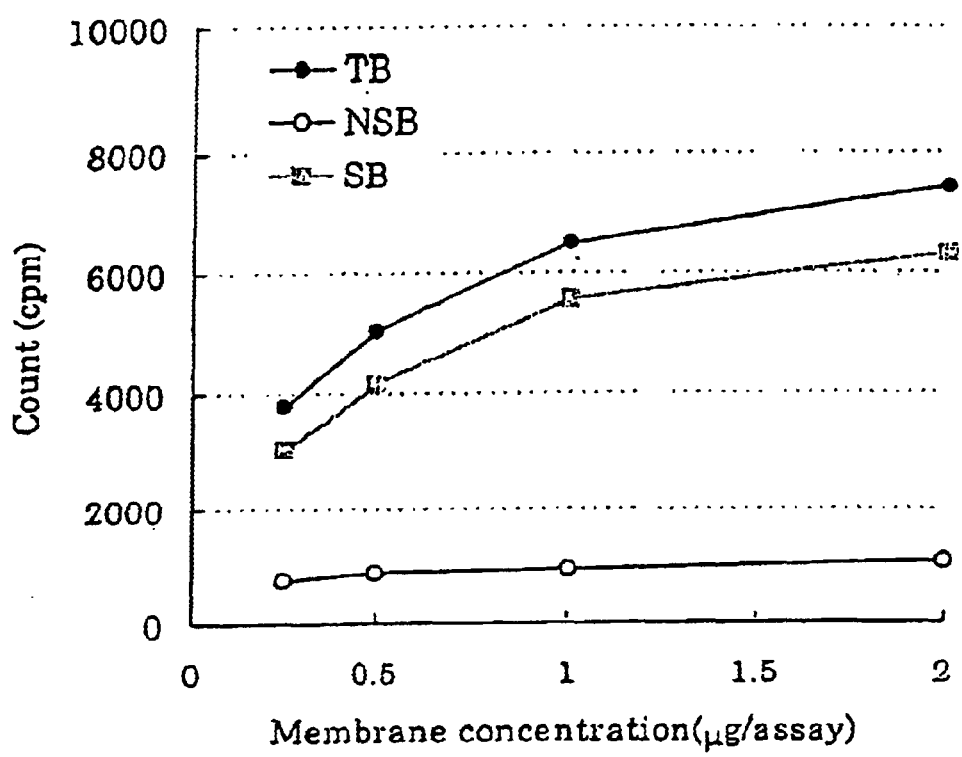
FIG. 9 shows specific binding of [$^{125}$I]-labeled MCH(4-19) prepared using a Bolton-Hunter reagent to a cell membrane fraction prepared from human SLC-1-expression CHO cells.

The cell membrane fraction prepared from human SLC-1-expression CHO cells according to EXAMPLE 16 was diluted with an assay buffer (25 mM Tris-HCl, 1 mM EDTA (ethylene diamine tetra acetic acid), 0.1% BSA (bovine serum albumin), 0.25 mM PMSF (phenylmethylsulfonyl fluoride), 1 μg/ml pepstatin, 20 μg/ml leupeptin, 10 μg/ml phosphoramidon, pH 7.5) in various concentration. Subsequently, 173 μl each of the dilution was dispensed in a 96-well plate. to assay for the total binding (TB), 2 μl of DMSO and 25 μl of 100 μM [$^{125}$I]-labeled MCH (4-19) were added and to assay for non-specific binding (NSB), 2 μl of a solution of 100 μM MCH in DMSO and 25 μl of 100 pM [$^{125}$I]-labeled MCH(4-19) were added, respectively, to the membrane fraction solution. after reacting at 25° C. for 60 minutes, the reaction solution was suction-filtrated through a polyethyleneimine-treated Whatman glass filter (GF-C). after filtration, the residual radioactivity of [$^{125}$I]-labeled MCH(4-19) remained on the filter paper was measured with a γ-counter. as shown in FIG. 9, specific binding (SB) of [$^{125}$I]-labeled MCH(4-19) was recognized dependent on the concentration of the membrane fraction.

Figure 10:
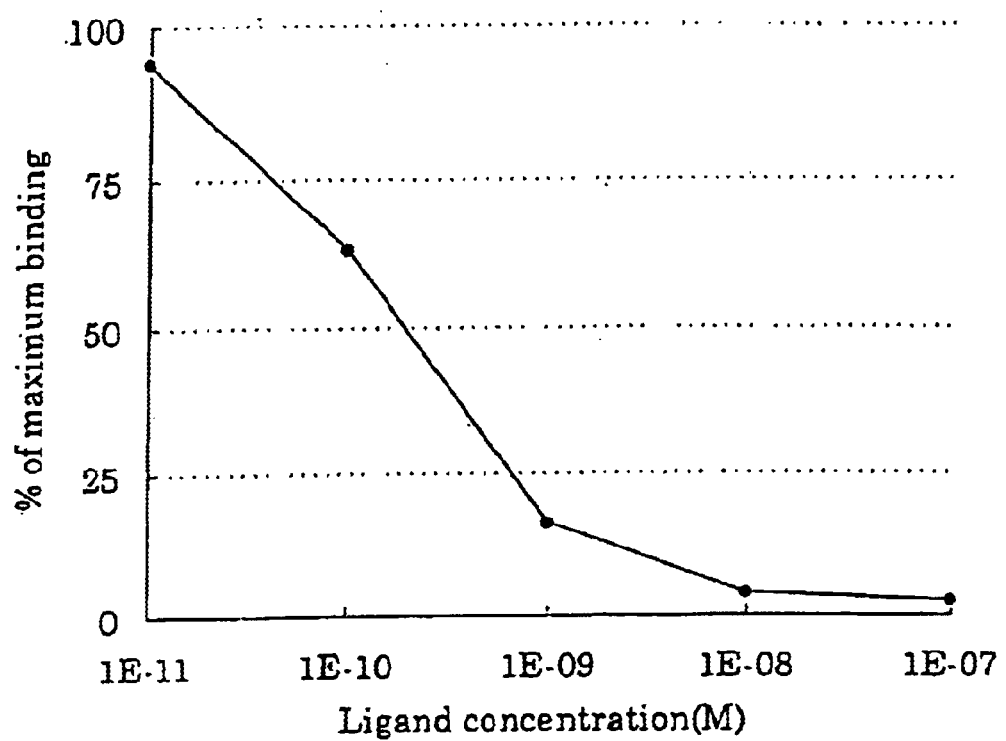
FIG. 10 shows a binding inhibition activity of MCH against [$^{125}$I]labeled MCH(4-19) prepared using a Bolton-Hunter reagent.

Also, by setting the membrane fraction concentration at 2.5 μg/ml, 50% inhibitory concentration (IC$_{50}$ value) of MCH was calculated from the inhibition rate (%). the IC$_{50}$ value was found to be 0.2 nM (FIG. 10).

A similar binding test can be carried out using a membrane fraction prepared from the rat SLC-1-expression CHO cells and [$^{125}$I]-labeled MCH(4-19).

Example 24

Preparation of MCH (Asp-Phe-Asp-Met-Leu-Arg-Cys-Met-Leu-Gly-Arg-Val-Tyr-Ar g-Pro-Cys-Trp-Gln-Val)

In a reaction tank of peptide synthesizer ABI 430a, 0.5 mmol of commercially available Boc-Val-OCH$_2$-PAM resin (0.77 mmol/g resin) was charged. in accordance with the Boc-strategy (NMP-HOBt) peptide synthesis, Boc-Gln, Boc-Trp(CHO), Boc-Cys(MeBzl), Boc-Pro, Boc-Arg(Tos), Boc-Tyr(Br-Z), Boc-Val. Boc-Arg(Tos), Boc-Gly, Boc-Leu. Boc-Met, Boc-Cys(MeBzl), Boc-Arg(Tos), Boc-Leu, Boc-Met, Boc-Asp (OcHex), Boc-Phe and Boc-Asp (OcHex)

were introduced into the resin in this order to give the desired protected peptide resin. the resulting resin, 0.6 g, was stirred at 0° C. for 60 minutes in 10 ml of anhydrous hydrogen fluoride together with 2 g of p-cresol and 1.2 ml of 1,4-butanedithiol. the hydrogen fluoride was then distilled off in vacuum. Diethyl ether was added to the residue and the precipitate was filtrated. Aqueous 50% acetic acid solution was added to the precipitate for extraction and insoluble matters were removed. after the extract was sufficiently concentrated, the concentrate was applied to Sephadex (trade name) G-25 column (2.0×80 cm) filled with 50% acetic acid aqueous solution followed by development with the same solvent. the main fractions were collected and applied to reverse phase chromatography column (2.6×60 cm) packed with LiChroprep (trade name) RP-18 followed by washing with 200 ml of water containing 0.1% TFA. Linear density gradient elution was performed with 300 ml of water containing 0.1% TFA and 300 ml of 40% aqueous acetonitrile solution containing 0.1% TFA. the main fractions were collected and concentrated. the concentrate was dissolved in approximately 4 ml of acetic acid. after diluting the solution with distilled water to a volume of 240 ml, pH was adjusted to 7.5 with ammonia water. the dilution was stirred while mildly blowing air therein. the reaction-was traced by HPLC. after it was confirmed that the peaks of the SH form peptide were all converted into the SS form, acetic acid was added to adjust pH of the solution to 3. then the solution was adsorbed onto the LiChroprep (trade name) RP-18 column supra. after washing the column with 200 ml of water containing 0.1% TFA, linear density gradient elution was carried out using 300 ml of water containing 0.1% TFA and 300 ml of 50% acetonitrile aqueous solution containing 0.1% TFA. the main fractions were collected and lyophilized to give the desired peptide.

Mass spectrum (M+H) 2387.3 (calcd. 2387.9)
Elution time on HPLC: 20.9 mins.
Column conditions:
　　Column: Wakosil-II 5C18HG (4.6×150 mm)
　　　　Eluant: linear density gradient elution with eluants a/B=20/80-80/20, using 10% acetonitrile aqueous solution containing 0.1% TFA as eluant a and 60% acetonitrile aqueous solution containing 0.1% TFA (20 mins.)
　　Flow rate: 1.0 ml/min.

Example 25

Preparation of Des-Asp$^1$-MCH (MCH(2-19), Phe-Asp-Met-Leu-Arg-Cys-Met-Leu-Gly-Arg-Val-Tyr-Arg-Pro -Cys-Trp-Gln-Val)

In a reaction tank of peptide synthesizer ABI 430a, 0.5 mmol of commercially available Boc-Val-OCH$_2$—PAM resin (0.77 mmol/g resin) was charged. According to the Boc-strategy (NMP-HOBt) peptide synthesis, Boc-Gln, Boc-Trp(CHO), Boc-Cys(MeBzl), Boc-Pro, Boc-Arg(Tos), Boc-Tyr(Br-Z), Boc-Val, Boc-Arg(Tos), Boc-Gly, Boc-Leu, Boc-Met, Boc-Cys(MeBzl), Boc-Arg(Tos), Boc-Leu. Boc-Met. Boc-Asp(OcHex) and Boc-Phe were introduced into the resin in this order to give the desired protected peptide resin. the resulting resin was treated as in EXAMPLE 25 by removal of the protecting groups, cyclization and purification to give the desired peptide.

Mass spectrum (M+H)$^+$ 2272.3 (calcd. 2272.1)
Elution time on HPLC: 20.6 mins.
Column conditions:
　　Column: Wakosil-II 5C18HG (4.6×150 mm)
　　　　Eluant: linear density gradient elution with eluants a/B=20/80-80/20, using 10% acetonitrile aqueous solution containing 0.1% TFA as eluant a and 60% acetonitrile aqueous solution containing 0.1% TFA (20 mins.)
　　Flow rate: 1.0 ml/min.

Example 26

Preparation of Des-[Asp$^1$,Phe$^2$]-MCH (MCH(3-19), Asp-Met-Leu-Arg-Cys-Met-Leu-Gly-Arg-Val-Tyr-Arg-Pro-Cys -Trp-Gln-Val)

In a reaction tank of peptide synthesizer ABI 430a, 0.5 mmol of commercially available Boc-Val-OCH$_2$-PAM resin (0.77 mmol/g resin) was charged. According to the Boc-strategy (NMP-HOBt) peptide synthesis, Boc-Gln, Boc-Trp (CHO), Boc-Cys(MeBzl), Boc-Pro, Boc-Arg(Tos), Boc-Tyr (Br-Z), Boc-Val, Boc-Arg(Tos), Boc-Gly, Boc-Leu, Boc-Met, Boc-Cys(MeBzl), Boc-Arg(Tos), Boc-Leu, Boc-Met and Boc-Asp(OcHex) were introduced into the resin in this order to give the desired protected peptide resin. the resulting resin was treated as in EXAMPLE 24 by removal of the protecting groups, cyclization and purification to give the desired peptide.

Mass spectrum (M+H)$^+$ 2124.8 (calcd. 2125.0)
Elution time on HPLC: 19.2 mins.
Column conditions:
　　Column: Wakosil-II 5C18HG (4.6×150 mm)
　　　　Eluant: linear density gradient elution with eluants a/B=20/80-80/20, using 10% acetonitrile aqueous solution containing 0.1% TFA as eluant a and 60% acetonitrile aqueous solution containing 0.1% TFA (20 mins.)
　　Flow rate: 1.0 ml/min.

Example 27

Preparation of Des-[Asp$^1$,Phe$^2$,Asp$^3$]-MCH (MCH (4-19), Met-Leu-Arg-Cys-Met-Leu-Gly-Arg-Val-Tyr-Arg-Pro-Cys-Trp -Gln-Val)

In a reaction tank of peptide synthesizer ABI 430a, 0.5 mmol of commercially available Boc-Val-OCH$_2$—PAM resin (0.77 mmol/g resin) was charged. According to the Boc-strategy (NMP-HOBt) peptide synthesis, Boc-Gln, Boc-Trp(CHO), Boc-Cys(MeBzl), Boc-Pro, Boc-Arg(Tos), Boc-Tyr(Br-Z), Boc-Val, Boc-Arg(Tos), Boc-Gly, Boc-Leu, Boc-Met, Boc-Cys(MeBzl), Boc-Arg(Tos), Boc-Leu and Boc-Met were introduced into the resin in this order to give the desired protected peptide resin. the resulting resin was treated as in EXAMPLE 24 by removal of the protecting groups, cyclization and purification to give the desired peptide.

Mass spectrum (M+H)$^+$ 2009.9 (calcd. 2010.0)
Elution time on HPLC: 17.9 mins.
Column conditions:
　　Column: Wakosil-II 5C18HG (4.6×150 mm)
　　　　Eluant: linear density gradient elution with eluants a/B=20/80-80/20, using 10% acetonitrile aqueous solution containing 0.1% TFA as eluant a and 60% acetonitrile aqueous solution containing 0.1% TFA (20 mins.)
　　Flow rate: 1.0 ml/min.

Example 28

Preparation of Des-[Asp$^1$, Phe$^2$, Asp$^3$, Met$^4$]-MCH (MCH(5-19), Leu-Arg-Cys-Met-Leu-Gly-Arg-Val-Tyr-Arg-Pro-Cys-Trp-Gln -Val-OH)

In a reaction tank of peptide synthesizer ABI 430a, 0.5 mmol of commercially available Boc-Val-OCH$_2$-PAM resin (0.77 mmol/g resin) was charged. According to the Boc-strategy (NMP-HOBt) peptide synthesis, Boc-Gln, Boc-Trp (CHO), Boc-Cys(MeBzl), Boc-Pro, Boc-Arg(Tos), Boc-Tyr (Br-Z), Boc-Val, Boc-Arg(Tos), Boc-Gly, Boc-Leu, Boc-Met, Boc-Cys(MeBzl), Boc-Arg(Tos) and Boc-Leu were introduced into the resin in this order to give the desired protected peptide resin. the resulting resin was treated as in 24 by removal of the protecting groups, cyclization and purification to give the desired peptide.

Mass spectrum (M+H)$^+$ 1878.9 (calcd. 1878.9)
Elution time on HPLC: 17.4 mins.
Column conditions:
   Column: Wakosil-II 5C18HG (4.6×150 mm)
      Eluant: linear density gradient elution with eluants a/B=20/80-80/20, using 10% acetonitrile aqueous solution containing 0.1% TFA as eluant a and 60% acetonitrile aqueous solution containing 0.1% TFA (20 mins.)
   Flow rate: 1.0 ml/min.

(Sequence Listing Free Text)
SEQ ID NO: 1
   Other information on the sequence: the two Cys residues at the 7th and 16th form intramolecular disulfide bond.
SEQ ID NO: 2
   Other information on the sequence: the two Cys residues at the 7th and 16th form intramolecular disulfide bond.
SEQ ID NO: 19
   Other information on the sequence: the two Cys residues at the 6th and 15th form intramolecular disulfide bond.
SEQ ID NO: 20
   Other information on the sequence: the two Cys residues at the 5th and 14th form intramolecular disulfide bond.
SEQ ID NO: 21
   Other information on the sequence: the two Cys residues at the 4th and 13th form intramolecular disulfide bond.
SEQ ID NO: 22
   Other information on the sequence: the two Cys residues at the 3rd and 12th form intramolecular disulfide bond.
SEQ ID NO: 23
   Other information on the sequence: the two Cys residues at the 2nd and 11th form intramolecular disulfide bond.
SEQ ID NO: 24
   Other information on the sequence: the two Cys residues at the 1st and 10th form intramolecular disulfide bond.

INDUSTRIAL APPLICABILITY

The method for screening a compound or its salts that alter the binding property between MCH or its derivative or a salt thereof and the SLC-1 or its salt, characterized by using the MCH of the present invention or its derivative or a salt thereof and the SLC-1 or its salt is useful for screening SLC-1 agonists which can be used not only as appetite (eating) promoting agents but also as prophylactic/therapeutic agents for weak pains, atonic bleeding, before and after expulsion, subinvolution of uterus, cesarean section, induced abortion, galactostasis, etc., and SLC-1 antagonists which can be used not only as antiobestic agents (drugs), appetite (eating) modulators, etc. but also as prophylactic/therapeutic agents for hyperstimulation, ankylosing uterine contractions, fetal distress, uterine rupture, cervical laceration, preterm delivery, Prader-Willi syndrome, etc.

What is claimed is:

1. A method for screening a compound or its salt that alters the binding property between [$^{125}$I][N-(3-(4-hydroxy-3-iodophenyl)propionyl)-Met$^4$]-MCH(4-19) and SLC-1 or its salt, which comprises:

measuring the amount of the [$^{125}$I][N-(3-(4-hydroxy-3-iodophenyl)propionyl)-$^4$Met$^4$]-MCH(4-19) bound to the SLC-1, (i) when the [$^{125}$I][N-(3-(4-hydroxy-3-iodophenyl)propionyl)$^4$Met$^4$]-MCH(4-19) is brought into contact with the SLC-1 or a salt thereof, and (ii) when a test compound and the [$^{125}$I][N-(3-(4-hydroxy-3-iodophenyl)propionyl)$^4$Met$^4$]-MCH(4-19) are brought into contact with the SLC-1 or a salt thereof; and comparing (i) and (ii).

2. The method according to claim 1, wherein the [$^{125}$I][N-(3-(4-hydroxy-3-iodophenyl)propionyl)$^4$Met$^4$]-MCH(4-19) is represented by the following formula:

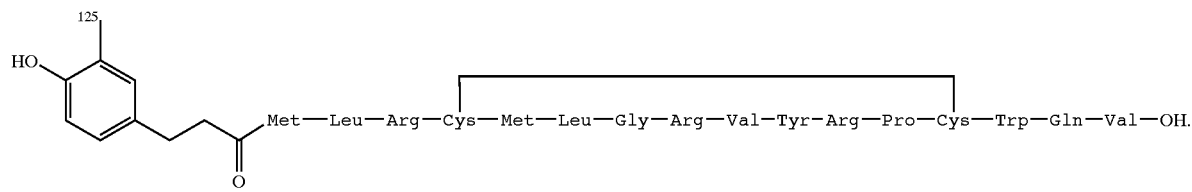

3. [$^{125}$I][N-(3-(4-hydroxy-3-iodophenyl)propionyl)-$^4$Met$^4$]-MCH(4-19) which is represented by the following formula:

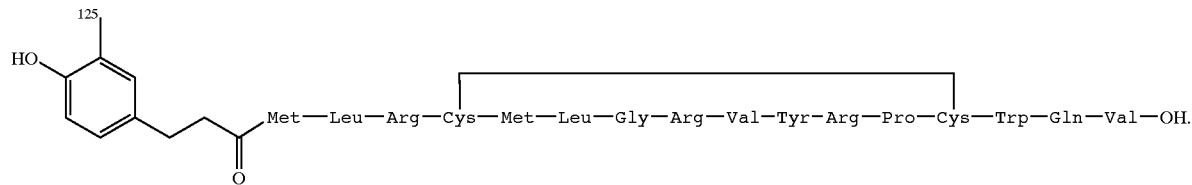

4. A kit for screening a compound or its salt that alters the binding property between [$^{125}$I][N-(3-(4-hydroxy-3-iodophenyl)$^4$Met$^4$]-MCH(4-19) and SLC-1 or its salt, which comprises a solution comprising (a) [$^{125}$I][N-(3-(4-hydroxy-3-iodophenyl)propionyl)$^4$Met$^4$]-MCH(4-19) and (b) a buffer.

5. The kit according to claim 4, wherein the [$^{125}$I][N-(3-(4-hydroxy-3-iodophenyl)propionyl)$^4$Met$^4$]-MCH(4-19) is represented by the following formula:

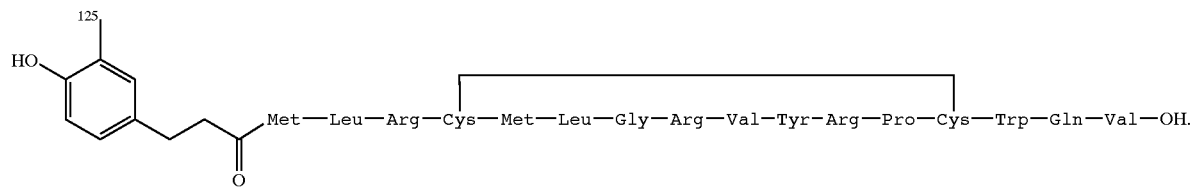

* * * * *

SEQUENCE LISTING

```
<160> NUMBER OF SEQ ID NOS: 24

<210> SEQ ID NO 1
<211> LENGTH: 16
<212> TYPE: PRT
<213> ORGANISM: Rattus sp.
<220> FEATURE:
<223> OTHER INFORMATION: The 7th cysteine residue binds with the 16th
      cysteine residue to form a intra-molecular disulfide-bond

<400> SEQUENCE: 1

Asp Phe Asp Met Leu Arg Cys Met Leu Gly Arg Val Tyr Arg Pro Cys
 1               5                  10                  15

<210> SEQ ID NO 2
<211> LENGTH: 19
<212> TYPE: PRT
<213> ORGANISM: Rattus sp.
<220> FEATURE:
<223> OTHER INFORMATION: The 7th cysteine residue binds with the 16th
      cysteine residue to form a intra-molecular disulfide-bond

<400> SEQUENCE: 2

Asp Phe Asp Met Leu Arg Cys Met Leu Gly Arg Val Tyr Arg Pro Cys
 1               5                  10                  15

Trp Gln Val

<210> SEQ ID NO 3
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcgacatgg atctgcaaac ctcgttgctg tg                                    32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actagttcag gtgcctttgc tttctgtcct ct                                    32

<210> SEQ ID NO 5
<211> LENGTH: 353
<212> TYPE: PRT
<213> ORGANISM: Rattus sp.

<400> SEQUENCE: 5
```

Met Asp Leu Gln Thr Ser Leu Leu Ser Thr Gly Pro Asn Ala Ser Asn
 1               5                  10                  15

Ile Ser Asp Gly Gln Asp Asn Leu Thr Leu Pro Gly Ser Pro Pro Arg
                20                  25                  30

Thr Gly Ser Val Ser Tyr Ile Asn Ile Ile Met Pro Ser Val Phe Gly
            35                  40                  45

Thr Ile Cys Leu Leu Gly Ile Val Gly Asn Ser Thr Val Ile Phe Ala
        50                  55                  60

Val Val Lys Lys Ser Lys Leu His Trp Cys Ser Asn Val Pro Asp Ile
 65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
               100                 105                 110

Glu Thr Met Cys Thr Leu Ile Thr Ala Met Asp Ala Asn Ser Gln Phe
           115                 120                 125

Thr Ser Thr Tyr Ile Leu Thr Ala Met Thr Ile Asp Arg Tyr Leu Ala
       130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
               165                 170                 175

Pro Val Trp Leu Tyr Ala Arg Leu Ile Pro Phe Pro Gly Gly Ala Val
           180                 185                 190

Gly Cys Gly Ile Arg Leu Pro Asn Pro Asp Thr Asp Leu Tyr Trp Phe
       195                 200                 205

Thr Leu Tyr Gln Phe Phe Leu Ala Phe Ala Leu Pro Phe Val Val Ile
   210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
               245                 250                 255

```
Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr
```

<210> SEQ ID NO 6
<211> LENGTH: 1074
<212> TYPE: DNA
<213> ORGANISM: Rattus sp.

<400> SEQUENCE: 6

| | | | | | |
|---|---|---|---|---|---|
| gtcgacatgg | atctgcaaac | ctcgttgctg | tccactggcc | ccaatgccag | caacatctcc | 60 |
| gatggccagg | ataatctcac | attgccgggg | tcacctcctc | gcacagggag | tgtctcctac | 120 |
| atcaacatca | ttatgccttc | cgtgtttggt | accatctgtc | tcctgggcat | cgtgggaaac | 180 |
| tccacggtca | tctttgctgt | ggtgaagaag | tccaagctac | actggtgcag | caacgtcccc | 240 |
| gacatcttca | tcatcaacct | ctctgtggtg | gatctgctct | tcctgctggg | catgcctttc | 300 |
| atgatccacc | agctcatggg | gaacggcgtc | tggcactttg | ggaaaccat | gtgcaccctc | 360 |
| atcacagcca | tggacgccaa | cagtcagttc | actagcacct | acatcctgac | tgccatgacc | 420 |
| attgaccgct | acttggccac | cgtccacccc | atctcctcca | ccaagttccg | gaagccctcc | 480 |
| atggccaccc | tggtgatctg | cctcctgtgg | gcgctctcct | tcatcagtat | caccccctgtg | 540 |
| tggctctacg | ccaggctcat | tcccttccca | gggggtgctg | tgggctgtgg | catccgcctg | 600 |
| ccaaacccgg | acactgacct | ctactggttc | actctgtacc | agttttttcct | ggcctttgcc | 660 |
| cttccgtttg | tggtcattac | cgccgcatac | gtgaaaatac | tacagcgcat | gacgtcttcg | 720 |
| gtggccccag | cctcccaacg | cagcatccgg | cttcggacaa | agagggtgac | ccgcacggcc | 780 |
| attgccatct | gtctggtctt | ctttgtgtgc | tgggcaccct | actatgtgct | gcagctgacc | 840 |
| cagctgtcca | tcagccgccc | gaccctcacg | tttgtctact | tgtacaacgc | ggccatcagc | 900 |
| ttgggctatg | ctaacagctg | cctgaacccc | tttgtgtaca | tagtgctctg | tgagaccttt | 960 |
| cgaaaacgct | tggtgttgtc | agtgaagcct | gcagcccagg | ggcagctccg | cacggtcagc | 1020 |
| aacgctcaga | cagctgatga | ggagaggaca | gaaagcaaag | gcacctgaac | tagt | 1074 |

<210> SEQ ID NO 7
<211> LENGTH: 262
<212> TYPE: RNA
<213> ORGANISM: Rattus sp.

<400> SEQUENCE: 7

| | | | | | |
|---|---|---|---|---|---|
| gcgaauuggg | uaccgggccc | ccccucgagg | ucgacgguau | cgauaagcuu | gauaucgaau | 60 |
| uccugcagcc | cggggaucc | gcccacuagu | ucaggugccu | uugcuuucug | uccucuccuc | 120 |
| aucagcuguc | ugagcguugc | ugaccgugcg | gagcugcccc | ugggcugcag | gcuucacuga | 180 |
| caacaccaag | cguuuucgaa | aggucucaca | gagcacuaug | uacacaaagg | gguucaggca | 240 |

```
gcuguuagca uagcccaagc ug                                              262

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caacagctgc ctcaaccc                                                    18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cctggtgatc tgcctcct                                                    18

<210> SEQ ID NO 10
<211> LENGTH: 1275
<212> TYPE: DNA
<213> ORGANISM: Homo sapiens

<400> SEQUENCE: 10
taggtgatgt cagtgggagc catgaagaag ggagtgggga gggcagttgg gcttggaggc      60
ggcagcggct gccaggctac ggaggaagac ccccttccca actgcgggc ttgcgctccg      120 ggacaaggtg gcaggcgctg gaggctgccg cagcctgcgt gggtggaggg gagctcagct     180
cggttgtggg agcaggcgac cggcactggc tgatggacc tggaagcctc gctgctgccc     240
actggtccca acgccagcaa cacctctgat ggccccgata acctcacttc ggcaggatca     300
cctcctcgca cggggagcat ctcctacatc aacatcatca tgccttcggt gttcggcacc     360
atctgcctcc tgggcatcat cgggaactcc acggtcatct tcgcggtcgt gaagaagtcc     420
aagctgcact ggtgcaacaa cgtccccgac atcttcatca tcaacctctc ggtagtagat     480
ctcctctttc tcctgggcat gccctttcatg atccaccagc tcatgggcaa tggggtgtgg     540
cactttgggg agaccatgtg caccctcatc acggccatga tgccaatag tcagttcacc     600 agcacctaca tcctgaccgc catggccatt gaccgctacc tggccactgt ccaccccatc     660
tcttccacga agttccggaa gccctctgtg gccaccctgt tgatctgcct cctgtgggcc     720
ctctccttca tcagcatcac ccctgtgtgg ctgtatgcca gactcatccc cttcccagga     780
ggtgcagtgg gctgcggcat acgcctgccc aacccagaca ctgacctcta ctggttcacc     840
ctgtaccagt ttttcctggc ctttgccctg cctttttgtgg tcatcacagc cgcatacgtg     900
aggatcctgc agcgcatgac gtcctcagtg gcccccgcct cccagcgcag catccggctg     960
cggacaaaga gggtgacccg cacagccatc gccatctgtc tggtcttctt tgtgtgctgg    1020
gcaccctact atgtgctaca gctgacccag ttgtccatca gccgcccgac cctcaccttt    1080
gtctacttat acaatgcggc catcagcttg ggctatgcca acagctgcct caaccccttt    1140
gtgtacatcg tgctctgtga gacgttccgc aaacgcttgg tcctgtcggt gaagcctgca    1200 gcccagggc agcttcgcgc tgtcagcaac gctcagacgg ctgacgagga gaggacagaa    1260
```
agcaaaggca cctga    1275

<210> SEQ ID NO 11
<211> LENGTH: 422
<212> TYPE: PRT
<213> ORGANISM: Homo sapiens

<400> SEQUENCE: 11

Met Ser Val Gly Ala Met Lys Lys Gly Val Gly Arg Ala Val Gly Leu
 1               5                  10                  15
Gly Gly Gly Ser Gly Cys Gln Ala Thr Glu Glu Asp Pro Leu Pro Asn
            20                  25                  30
Cys Gly Ala Cys Ala Pro Gly Gln Gly Gly Arg Arg Trp Arg Leu Pro
        35                  40                  45
Gln Pro Ala Trp Val Glu Gly Ser Ser Ala Arg Leu Trp Glu Gln Ala
    50                  55                  60
Thr Gly Thr Gly Trp Met Asp Leu Glu Ala Ser Leu Leu Pro Thr Gly
65                  70                  75                  80
Pro Asn Ala Ser Asn Thr Ser Asp Gly Pro Asp Asn Leu Thr Ser Ala
                85                  90                  95
Gly Ser Pro Pro Arg Thr Gly Ser Ile Ser Tyr Ile Asn Ile Ile Met
            100                 105                 110
Pro Ser Val Phe Gly Thr Ile Cys Leu Leu Gly Ile Ile Gly Asn Ser
        115                 120                 125
Thr Val Ile Phe Ala Val Val Lys Lys Ser Lys Leu His Trp Cys Asn
    130                 135                 140
Asn Val Pro Asp Ile Phe Ile Ile Asn Leu Ser Val Val Asp Leu Leu
145                 150                 155                 160
Phe Leu Leu Gly Met Pro Phe Met Ile His Gln Leu Met Gly Asn Gly
                165                 170                 175
Val Trp His Phe Gly Glu Thr Met Cys Thr Leu Ile Thr Ala Met Asp
            180                 185                 190
Ala Asn Ser Gln Phe Thr Ser Thr Tyr Ile Leu Thr Ala Met Ala Ile
        195                 200                 205
Asp Arg Tyr Leu Ala Thr Val His Pro Ile Ser Ser Thr Lys Phe Arg
    210                 215                 220
Lys Pro Ser Val Ala Thr Leu Val Ile Cys Leu Leu Trp Ala Leu Ser
225                 230                 235                 240
Phe Ile Ser Ile Thr Pro Val Trp Leu Tyr Ala Arg Leu Ile Pro Phe
                245                 250                 255
Pro Gly Gly Ala Val Gly Cys Gly Ile Arg Leu Pro Asn Pro Asp Thr
            260                 265                 270
Asp Leu Tyr Trp Phe Thr Leu Tyr Gln Phe Leu Ala Phe Ala Leu
    275                 280                 285
Pro Phe Val Val Ile Thr Ala Ala Tyr Val Arg Ile Leu Gln Arg Met
    290                 295                 300
Thr Ser Ser Val Ala Pro Ala Ser Gln Arg Ser Ile Arg Leu Arg Thr
305                 310                 315                 320
Lys Arg Val Thr Arg Thr Ala Ile Ala Ile Cys Leu Val Phe Phe Val
                325                 330                 335
Cys Trp Ala Pro Tyr Tyr Val Leu Gln Leu Thr Gln Leu Ser Ile Ser
            340                 345                 350
Arg Pro Thr Leu Thr Phe Val Tyr Leu Tyr Asn Ala Ala Ile Ser Leu
        355                 360                 365

```
Gly Tyr Ala Asn Ser Cys Leu Asn Pro Phe Val Tyr Ile Val Leu Cys
        370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
            420

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtcgacatgg acctggaagc ctcgctgctg c                              31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actagttcag gtgcctttgc tttctgtcct c                              31

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agtcgacatg tcagtgggag ccatgaagaa ggg                            33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aactagttca ggtgcctttg ctttctgtcc tct                            33

<210> SEQ ID NO 16
<211> LENGTH: 1074
<212> TYPE: DNA
<213> ORGANISM: Homo sapiens

<400> SEQUENCE: 16
gtcgacatgg acctggaagc ctcgctgctg ccactggtc ccaacgccag caacacctct    60
gatggccccg ataacctcac ttcggcagga tcacctcctc gcacggggag catctcctac   120
atcaacatca tcatgccttc ggtgttcggc accatctgcc tcctgggcat catcgggaac   180
tccacggtca tcttcgcggt cgtgaagaag tccaagctgc actggtgcaa caacgtcccc   240
```

```
gacatcttca tcatcaacct ctcggtagta gatctcctct ttctcctggg catgcccttc      300
atgatccacc agctcatggg caatggggtg tggcactttg gggagaccat gtgcaccctc      360
atcacggcca tggatgccaa tagtcagttc accagcacct catcctgac cgccatggcc       420 attgaccgct acctggccac tgtccacccc atctcttcca cgaagttccg gaagccctct      480
gtggccaccc tggtgatctg cctcctgtgg gccctctcct tcatcagcat cacccctgtg      540
tggctgtatg ccagactcat ccccttccca ggaggtgcag tgggctgcgg catacgcctg      600
cccaacccag acactgacct ctactggttc accctgtacc agttttttcct ggcctttgcc     660 ctgccttttg tggtcatcac agccgcatac gtgaggatcc tgcagcgcat gacgtcctca     720
gtggcccccg cctcccagcg cagcatccgg ctgcggacaa agagggtgac ccgcacagcc     780
atcgccatct gtctggtctt ctttgtgtgc tgggcaccct actatgtgct acagctgacc     840
cagttgtcca tcagccgccc gaccctcacc tttgtctact tatacaatgc ggccatcagc     900
ttgggctatg ccaacagctg cctcaacccc tttgtgtaca tcgtgctctg tgagacgttc     960
cgcaaacgct tggtcctgtc ggtgaagcct gcagcccagg ggcagcttcg cgctgtcagc    1020
aacgctcaga cggctgacga ggagaggaca gaaagcaaag gcacctgaac tagt          1074
```

<210> SEQ ID NO 17
<211> LENGTH: 1283
<212> TYPE: DNA
<213> ORGANISM: Homo sapiens

<400> SEQUENCE: 17

```
agtcgacatg tcagtgggag ccatgaagaa gggagtgggg agggcagttg ggcttggagg      60
cggcagcggc tgccaggcta cggaggaaga ccccttccc aactgcgggg cttgcgctcc      120
gggacaaggt ggcaggcgct ggaggctgcc gcagcctgcg tgggtggagg ggagctcagc      180
tcggttgtgg gagcaggcga ccggcactgg ctggatggac ctggaagcct cgctgctgcc      240
cactggtccc aacgccagca acacctctga tggccccgat aacctcactt cggcaggatc      300
acctcctcgc acgggagca tctcctacat caacatcatc atgccttcgg tgttcggcac      360
catctgcctc ctgggcatca tcgggaactc cacggtcatc ttcgcggtcg tgaagaagtc      420
caagctgcac tggtgcaaca acgtccccga catcttcatc atcaacctct cggtagtaga     480
tctcctcttt ctcctgggca tgcccttcat gatccaccag ctcatgggca atgggggtgtg    540 gcactttggg gagaccatgt gcaccctcat cacggccatg gatgccaata gtcagttcac     600
cagcacctac atcctgaccg ccatggccat tgaccgctac ctggccactg tccacccat     660 ctcttccacg aagttccgga agccctctgt ggccaccctg gtgatctgcc tcctgtgggc     720
cctctccttc atcagcatca cccctgtgtg gctgtatgcc agactcatcc ccttcccagg     780
aggtgcagtg ggctgcggca tacgcctgcc caacccagac actgacctct actggttcac     840
cctgtaccag ttttttcctgg cctttgccct gccttttgtg gtcatcacag ccgcatacgt     900
gaggatcctg cagcgcatga cgtcctcagt ggcccccgcc tcccagcgca gcatccggct     960
gcggacaaag agggtgaccc gcacagccat cgccatcgt ctggtcttct ttgtgtgctg    1020
ggcaccctac tatgtgctac agctgaccca gttgtccatc agccgcccga ccctcacctt    1080
tgtctactta tacaatgcgg ccatcagctt gggctatgcc aacagctgcc tcaacccctt    1140
tgtgtacatc gtgctctgtg agacgttccg caaacgcttg gtcctgtcgg tgaagcctgc    1200
agcccagggg cagcttcgcg ctgtcagcaa cgctcagacg gctgacgagg agaggacaga    1260
```

```
                                                     aagcaaaggc acctgaacta gtt                              1283

<210> SEQ ID NO 18
<211> LENGTH: 420
<212> TYPE: RNA
<213> ORGANISM: Homo sapiens

<400> SEQUENCE: 18
caaaagcugg agcuccaccg cgguggcggc cgcucuagcc cacuaguuca ggugccuuug     60
cuuucugucc ucccucguc agccgucuga gcguugcuga cagcgcgaag cugccccugg    120
gcugcaggcu ucaccgacag gaccaagcgu uugcggaacu cucacagag cacgauguac     180 acaaggggu ugaggcagcu guuggcauag cccaagcuga uggccgcauu guauaaguag     240 acaagguga gggucgggcg gcugauggac aacuggguca gcuguagcac auaguagggu    300
gcccagcaca caaagaagac cagacagaug gcgauggcug ugcgggucac ccucuuuguc    360
cgcagccgga ugcugcgcug ggaggcgggg gccacugagg acgucaugcg cugcaggauc    420

<210> SEQ ID NO 19
<211> LENGTH: 18
<212> TYPE: PRT
<213> ORGANISM: Rattus sp.
<220> FEATURE:
<223> OTHER INFORMATION: The 6th cysteine residue binds with the 15th
      cysteine residue to form a intra-molecular disulfide-bond

<400> SEQUENCE: 19

Phe Asp Met Leu Arg Cys Met Leu Gly Arg Val Tyr Arg Pro Cys Trp
  1               5                  10                  15

Gln Val

<210> SEQ ID NO 20
<211> LENGTH: 17
<212> TYPE: PRT
<213> ORGANISM: Rattus sp.
<220> FEATURE:
<223> OTHER INFORMATION: The 5th cysteine residue binds with the 14th
      cysteine residue to form a intra-molecular disulfide-bond

<400> SEQUENCE: 20

Asp Met Leu Arg Cys Met Leu Gly Arg Val Tyr Arg Pro Cys Trp Gln
  1               5                  10                  15

Val

<210> SEQ ID NO 21
<211> LENGTH: 16
<212> TYPE: PRT
<213> ORGANISM: Rattus sp.
<220> FEATURE:
<223> OTHER INFORMATION: The 4th cysteine residue binds with the 13th
      cysteine residue to form a intra-molecular disulfide-bond

<400> SEQUENCE: 21

Met Leu Arg Cys Met Leu Gly Arg Val Tyr Arg Pro Cys Trp Gln Val
  1               5                  10                  15

<210> SEQ ID NO 22
<211> LENGTH: 15
<212> TYPE: PRT
<213> ORGANISM: Rattus sp.
<220> FEATURE:
<223> OTHER INFORMATION: The 3rd cysteine residue binds with the 12th
      cysteine residue to form a intra-molecular disulfide-bond
```

-continued

```
<400> SEQUENCE: 22

Leu Arg Cys Met Leu Gly Arg Val Tyr Arg Pro Cys Trp Gln Val
  1               5                  10                  15

<210> SEQ ID NO 23
<211> LENGTH: 14
<212> TYPE: PRT
<213> ORGANISM: Rattus sp.
<220> FEATURE:
<223> OTHER INFORMATION: The 2nd cysteine residue binds with the 11th
      cysteine residue to form a intra-molecular disulfide-bond

<400> SEQUENCE: 23

Arg Cys Met Leu Gly Arg Val Tyr Arg Pro Cys Trp Gln Val
  1               5                  10

<210> SEQ ID NO 24
<211> LENGTH: 13
<212> TYPE: PRT
<213> ORGANISM: Rattus sp.
<220> FEATURE:
<223> OTHER INFORMATION: The 1st cysteine residue binds with the 10th
      cysteine residue to form a intra-molecular disulfide-bond

<400> SEQUENCE: 24

Cys Met Leu Gly Arg Val Tyr Arg Pro Cys Trp Gln Val
  1               5                  10
```